United States Patent [19]

Misono et al.

[11] Patent Number: 5,125,410
[45] Date of Patent: Jun. 30, 1992

[54] INTEGRATED ULTRASONIC DIAGNOSIS DEVICE UTILIZING INTRA-BLOOD-VESSEL PROBE

[75] Inventors: Kazuhiro Misono; Hiroshi Fujimoto, both of Hachioji; Katsuyuki Yamamoto, Sapporo, all of Japan

[73] Assignee: Olympus Optical Co., Ltd., Tokyo, Japan

[21] Appl. No.: 570,764

[22] Filed: Aug. 22, 1990

[30] Foreign Application Priority Data

| Oct. 13, 1989 | [JP] | Japan | 1-120204[U] |
| Oct. 13, 1989 | [JP] | Japan | 1-266800 |
| Oct. 26, 1989 | [JP] | Japan | 1-279092 |
| May 10, 1990 | [JP] | Japan | 2-122706 |
| May 10, 1990 | [JP] | Japan | 2-122713 |

[51] Int. Cl.⁵ .............................. A61B 8/14
[52] U.S. Cl. .................. 128/662.06; 128/908; 128/4
[58] Field of Search ............ 128/662.06, 637, 692, 128/4–6, 660.03, 303.15, 908

[56] References Cited

U.S. PATENT DOCUMENTS

| 4,237,729 | 12/1980 | McLeod et al. | 128/662.06 |
| 4,383,086 | 6/1989 | Bender et al. | 73/597 |
| 4,637,401 | 1/1987 | Johnston | 128/662.06 |
| 4,794,931 | 1/1989 | Yock | 128/662.06 |
| 4,917,097 | 4/1990 | Proudian et al. | 128/662.06 |
| 4,928,693 | 5/1990 | Goodin et al. | 128/637 |
| 4,947,852 | 8/1990 | Nassi et al. | 128/662.06 |
| 4,947,854 | 8/1990 | Rabinovitz et al. | 128/662.06 |
| 4,957,110 | 9/1990 | Vogel et al. | 128/692 |

FOREIGN PATENT DOCUMENTS 63-317130 12/1988 Japan.

Primary Examiner—Francis Jaworski
Assistant Examiner—George Manuel
Attorney, Agent, or Firm—Armstrong & Kubovcik

[57] ABSTRACT

An ultrasonic diagnosis device includes an ultrasonic oscillator, contained in a probe which can be inserted into a blood vessel, which can vary direction of transmission and reception of ultrasonic waves to receive an echo signal from the wall of the blood vessel thereby calculating information about the inner and outer walls of a blood vessel and obtaining cross-sectional and three-dimensional images of a blood vessel and the like.

54 Claims, 39 Drawing Sheets

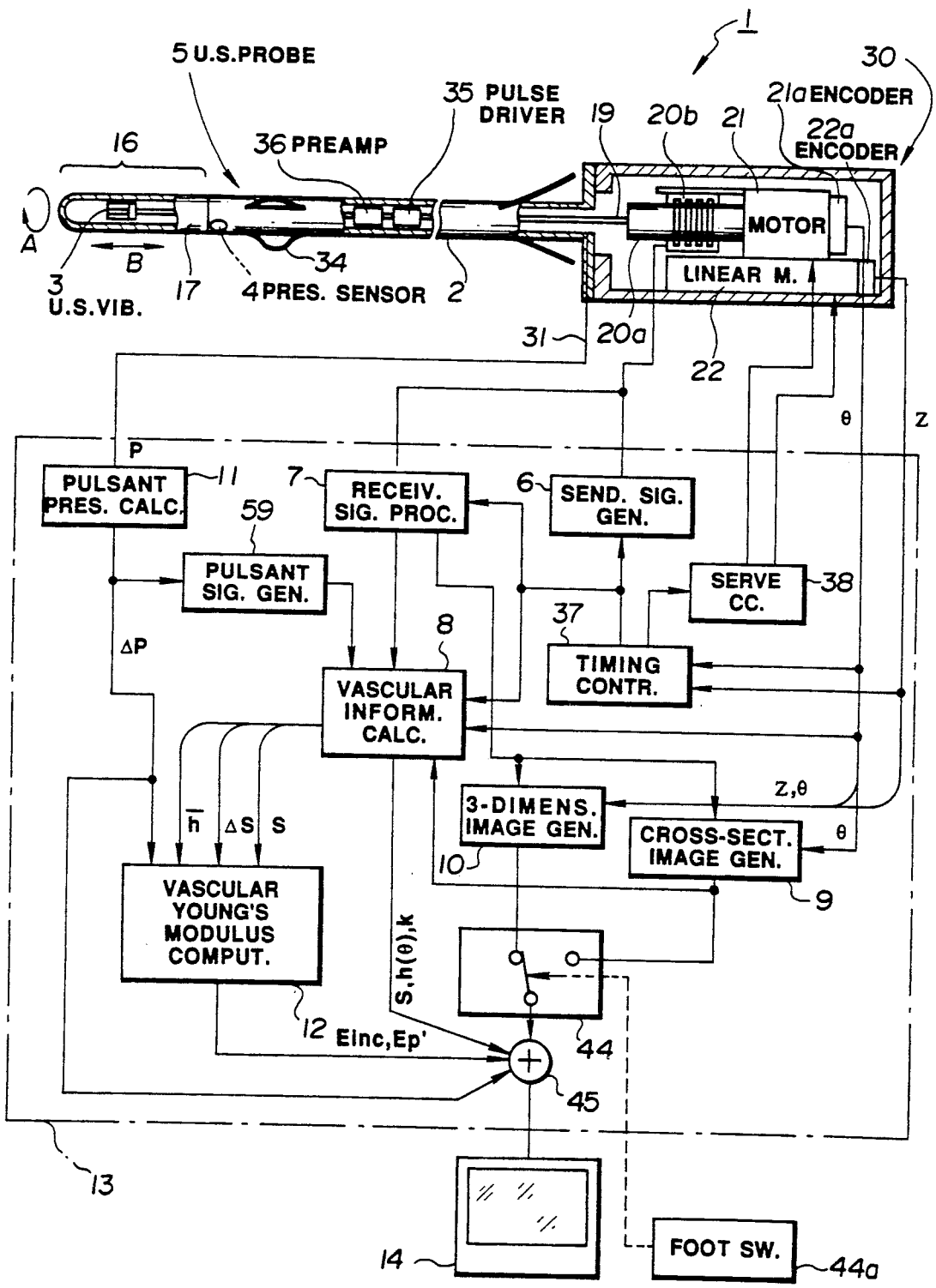

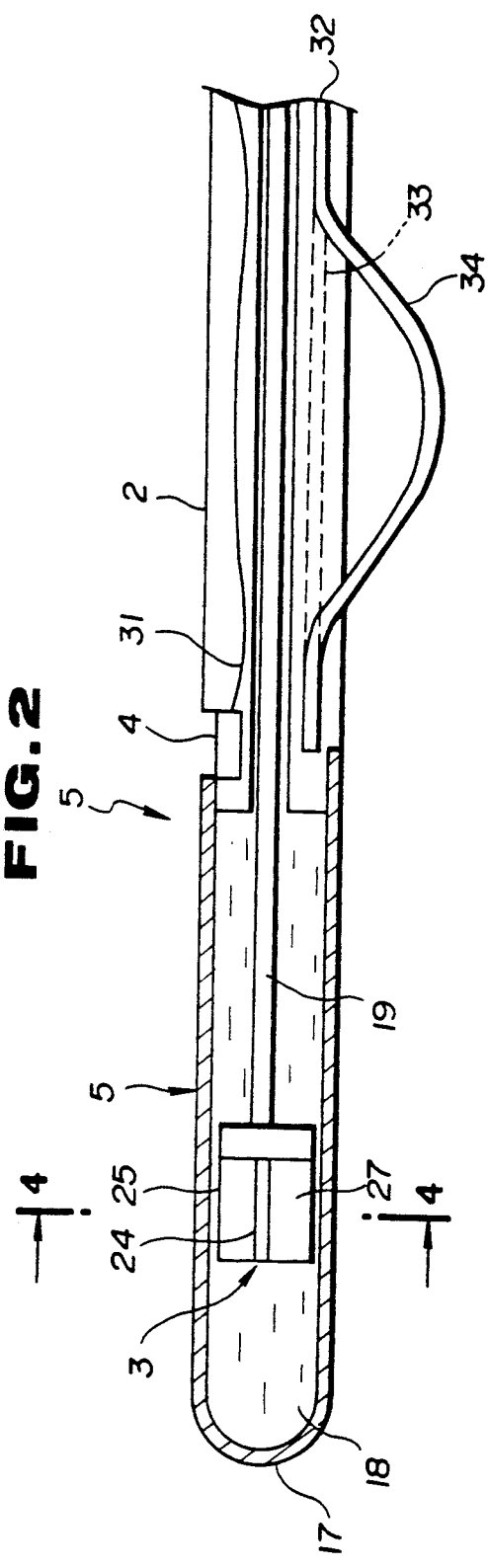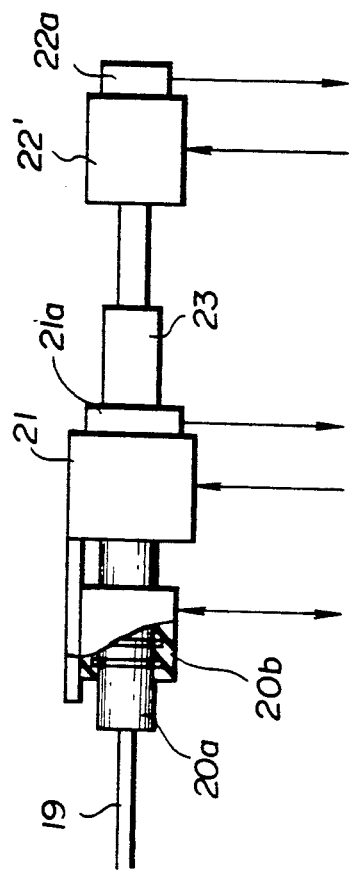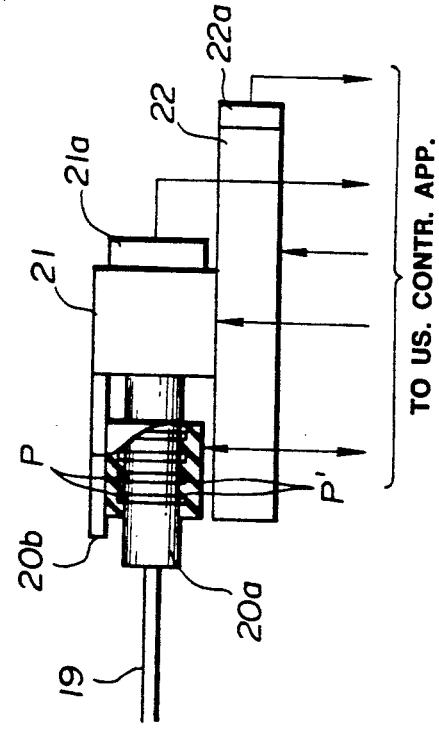

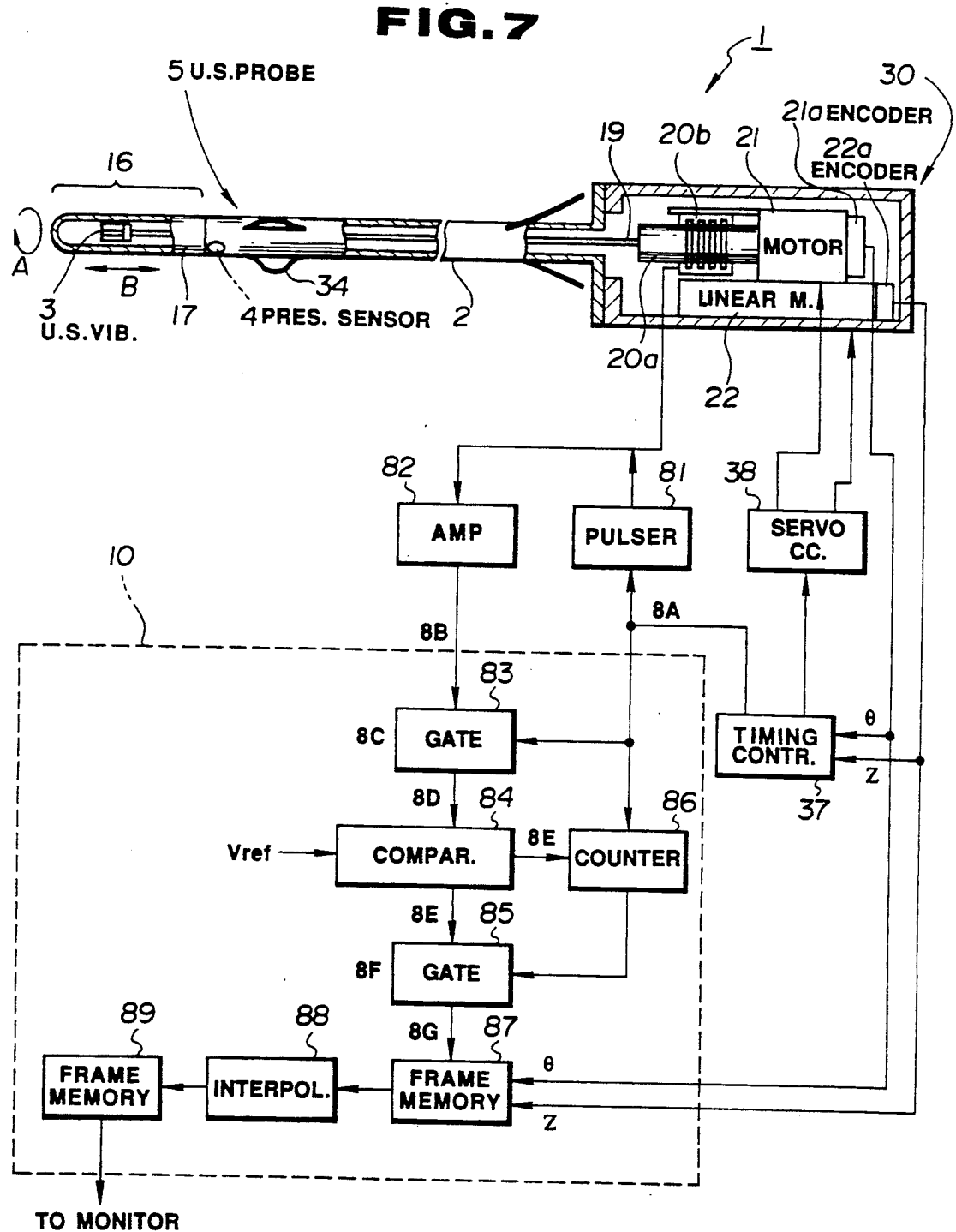

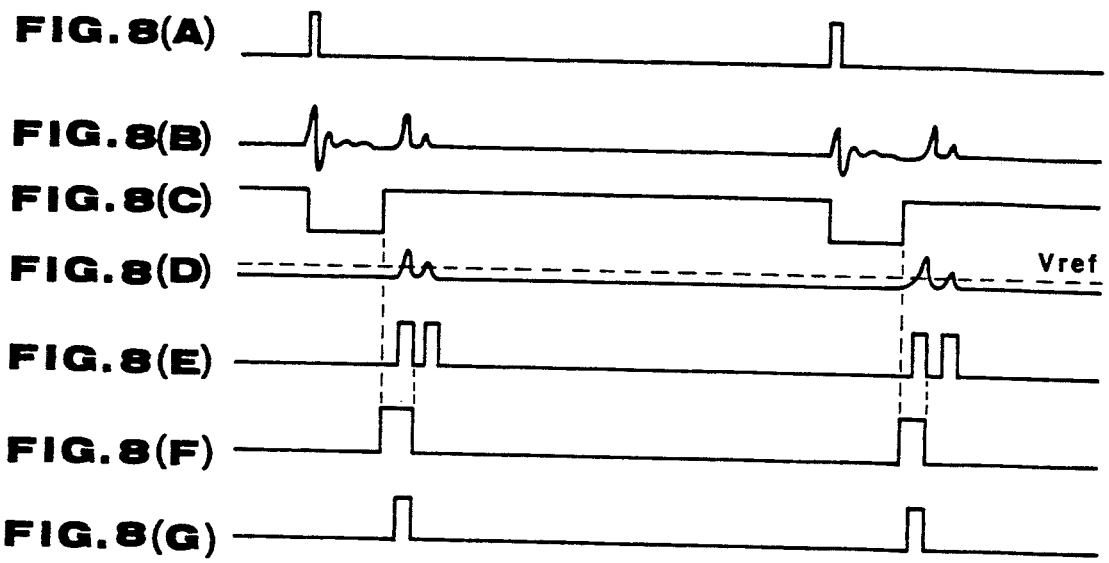
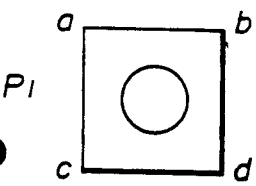
FIG. 9
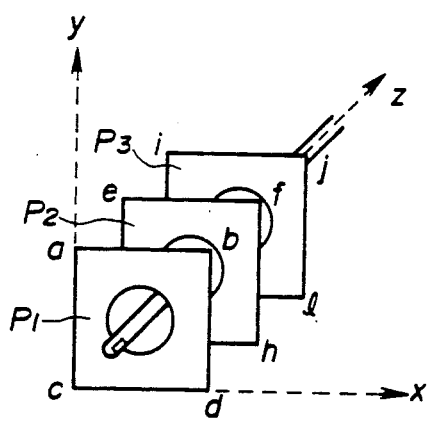
FIG. 10
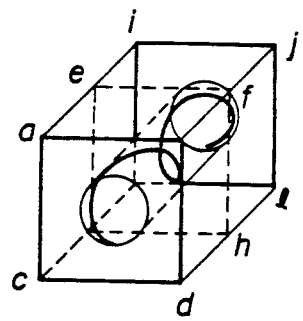
FIG. 11

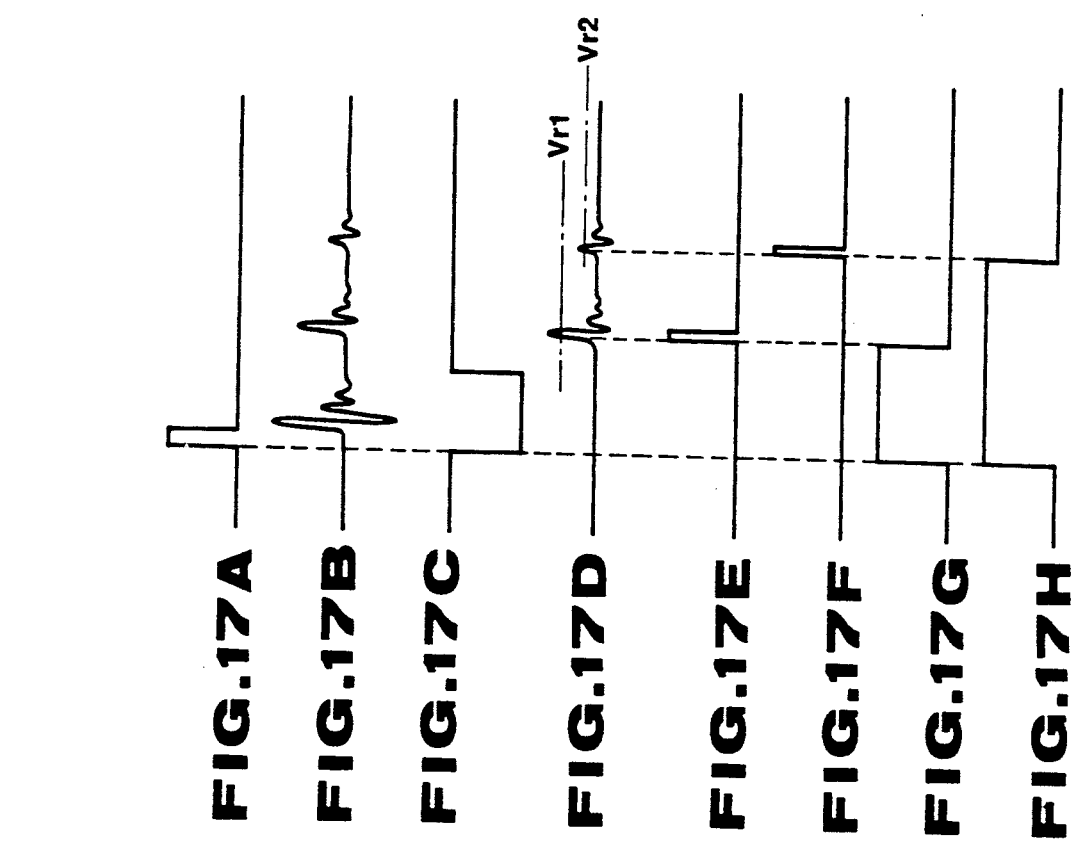
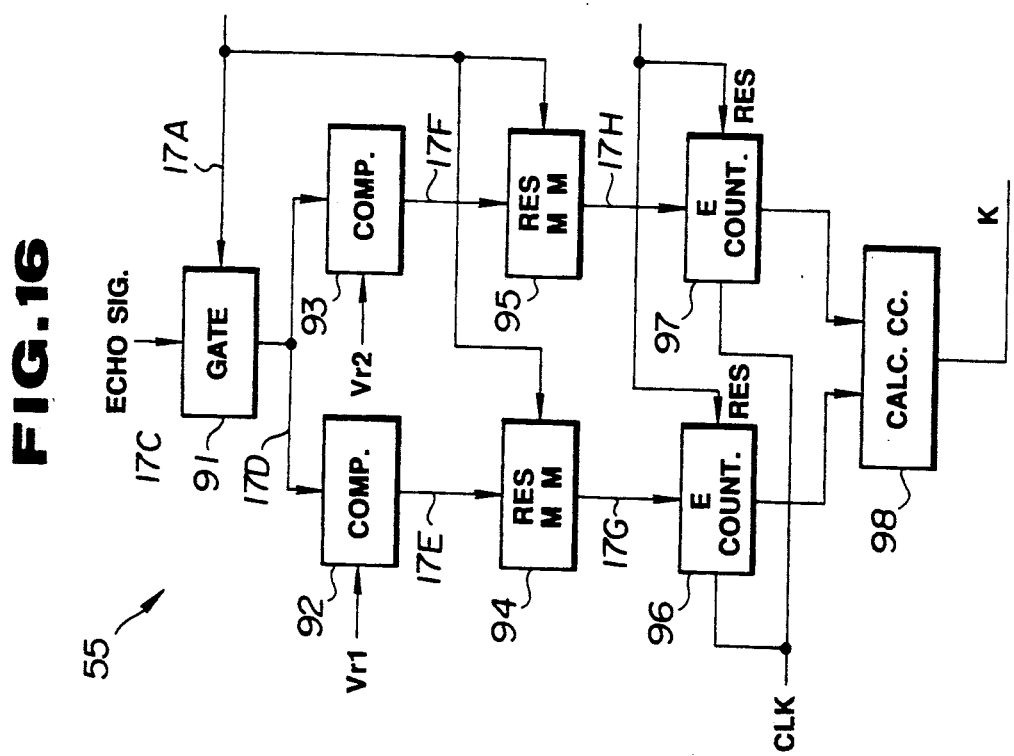

FIG.18 a
FIG.18 b
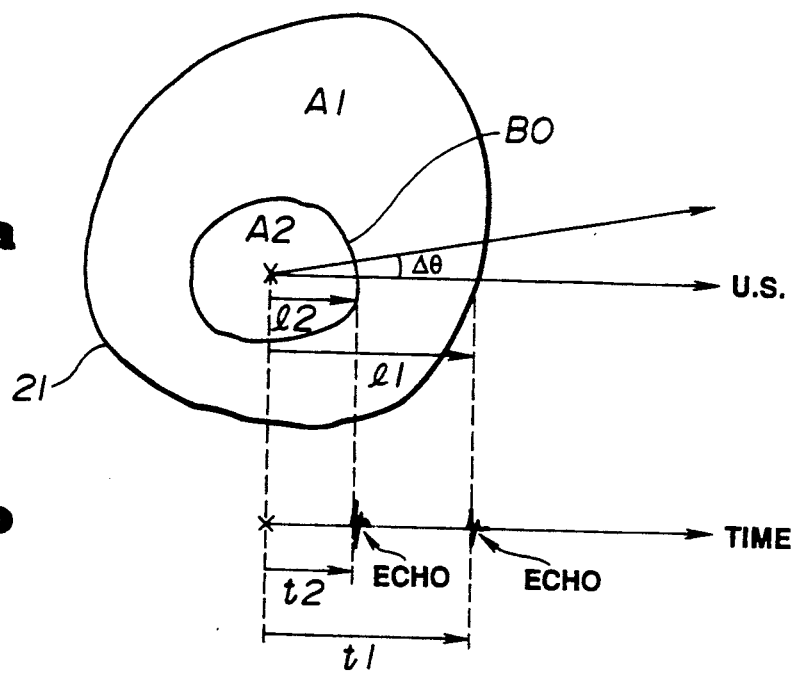
FIG.20
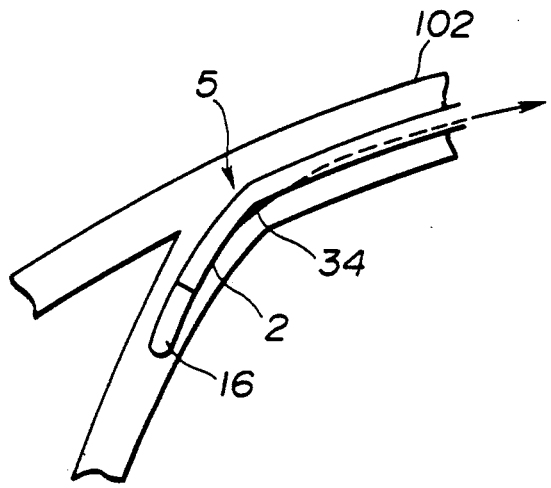
FIG.21
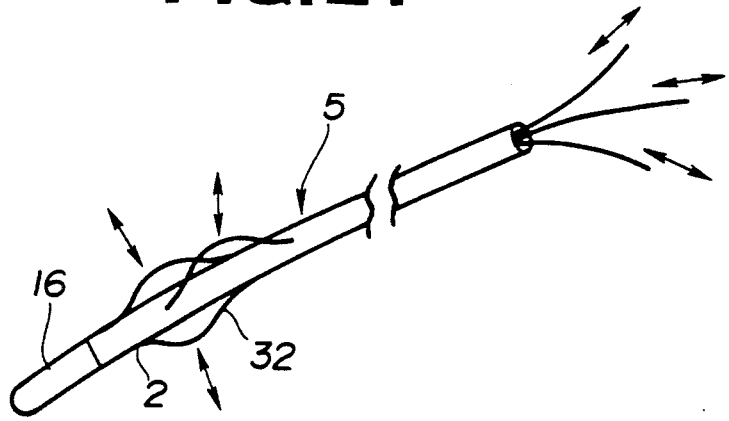

FIG. 42
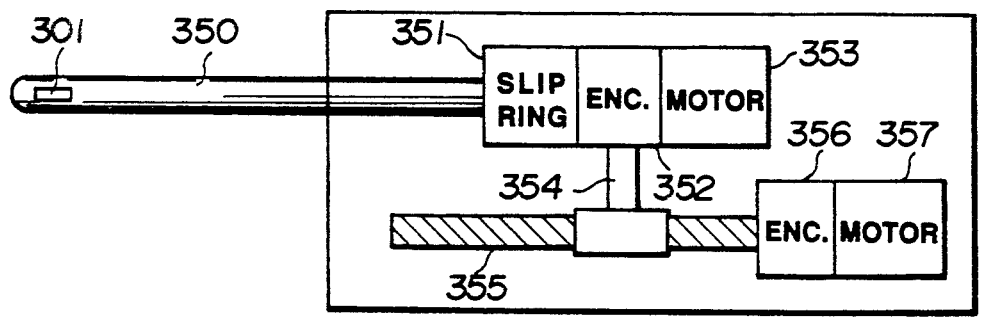
FIG. 43
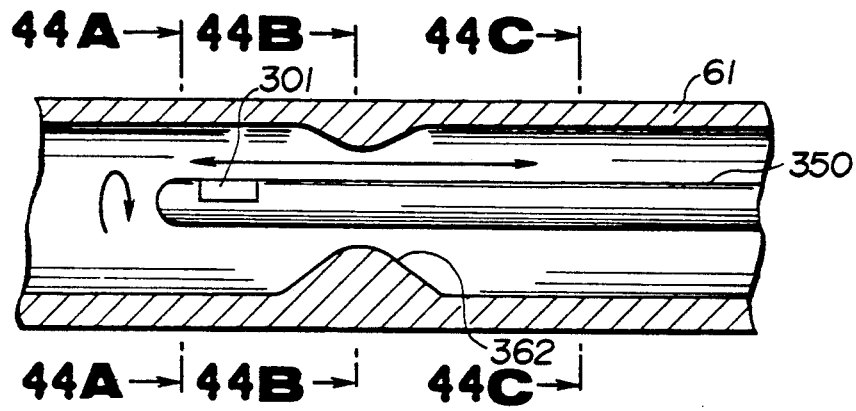
FIG. 44(a)     FIG. 44(b)     FIG. 44(c)
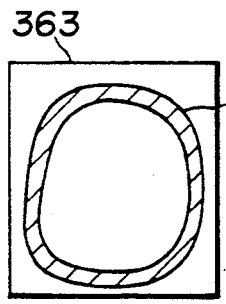 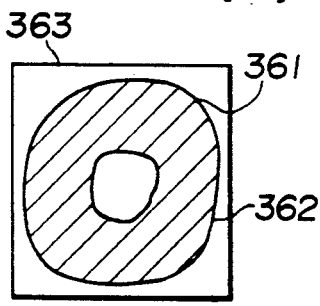 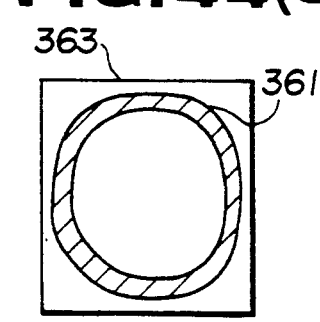
FIG. 45
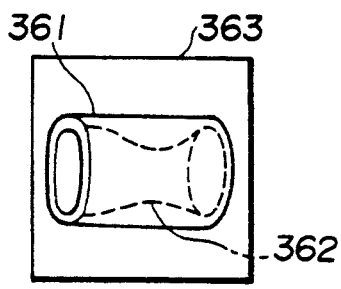

Vs

INTEGRATED ULTRASONIC DIAGNOSIS DEVICE UTILIZING INTRA-BLOOD-VESSEL PROBE

BACKGROUND OF THE INVENTION

The present invention relates to an ultrasonic diagnosis device which can diagnose various diseases of blood vessels using an ultrasonic probe which can be inserted into blood vessels.

A technique for imaging the status of blood vessels has become indispensable for diagnosis and operation of various diseases of blood vessels such as arterial sclerosis and aneurysm. In addition to the observation of blood vessel images using the imaging techniques, quantitative measurement of the cross-section of blood vessels and the thickness of blood vessel walls will provide objective standards for evaluating the shape of blood vessels which enables very effective diagnosis and post-operative evaluation of artificial blood vessels. Also, since the blood vessels having a disease are greatly different from healthy blood vessels in dynamical characteristics, the measurement of the dynamical characteristics in addition to the imaging and quantitative measurement will enable more effective diagnosis.

Conventional devices for imaging the shape of blood vessels include X-ray devices, X-ray CT devices and MRI (Magnetic Resonance Imaging) devices for angiography, ultrasonic diagnosis devices for laminagraphy and angioscopes utilizing a fiberscope.

In angiography using a X-ray device, contrast medium are injected into blood vessels in order to facilitate X-ray diagnosis. Though this method is widely used in clinical medicine, it has shortcomings that it is very uncomfortable for patients to whom the contrast medium is injected and that the blood vessel shape information available with this method is two-dimensional observation limited to the periphery of blood vessel caves. With X-ray CT devices or MRI devices, the cross-sectional images of blood vessels can be obtained without the contrast medium. However, the cross-sectional images obtained by these devices are of relatively low resolution and insufficient for the observation of blood vessel shape.

Ultrasonic diagnosis devices enable non-invasive and real-time observation of blood vessels. However, the observation is limited to the blood vessels which can receive the ultrasonic wave coming from the surface of the body. In addition, the resolution of these devices is low. In angioscopes which is inserted into blood vessels for shape observation, transparent liquid is rapidly injected to enable observation and recording of the surface of blood vessel caves. However, this method has shortcomings in that the period during which the injected liquid is sufficiently transparent, i.e. the period for observation is short, and that the observation is limited to the surface of blood vessel caves.

Thus, the devices described above are employed only for the detection of the extreme abnormality of blood vessel shape such as hemadostenosis, for the reasons that the shape information they provide is two-dimensional, that their observation range and resolution are insufficient and that continuous observation is not possible.

Ultrasonic diagnosis technologies which obtain ultrasonic images of the cross-sectional shape of blood vessels using an ultrasonic probe have been developed recently. For example, Japan Pat. No. 62-270,140 (U.S. Pat. No. 4,794,931) discloses a device to obtain ultrasonic images of the cross-sectional shape of blood vessels wherein, an ultrasonic oscillator is provided on the end of an ultrasonic probe (catheter) which is inserted into blood vessels. The ultrasonic oscillator generates ultrasonic waves for diagnosis and receives echoes from the location to be observed. The ultrasonic waves are transmitted or received in an axial direction of the probe using the ultrasonic oscillator or an ultrasonic mirror.

However, though this device provides two-dimensional cross-sectional images of blood vessels, it does not provide longitudinal images in the axial direction or three-dimensional images.

Also, this device does not enable quantitative measurement of the cross-sectional area of blood vessels, the thickness and smoothness of blood vessel walls. It does not serve sufficient diagnosis because its measurement is only qualitative measurement to observe significant changes in blood vessel shape such as hemadostenosis by imaging blood vessels.

It is very much effective in blood vessel diagnosis, especially in the diagnosis of arteriosclerosis, to measure the dynamical characteristics of blood vessels that is the elasticity of blood vessels. The reason for this is that the elasticity of blood vessels is closely related to the shape of blood vessels and therefore the change in the quality of blood vessel organ is reflected in the elasticity of blood vessels prior to the change in blood vessel shape, and that the elasticity of blood vessels is the most quantitative parameter to be used for evaluation of the hardness of blood vessels.

An ultrasonic method has been used to obtain the elasticity of blood vessels. In the ultrasonic method, the elasticity of blood vessels is obtained by calculation based on the diameter or cross-sectional area of blood vessel walls, the change in them in response to pulsation and the thickness of blood vessels which are measured by non-invasively directing ultrasonic waves to blood vessels from the surface of the body.

The principle of measurement is the same for all of the various methods to obtain the elasticity of blood vessels which have been proposed. It is to measure the change in the internal pressure of blood vessels caused by pulsation, that is the rate of blood vessel deformation against the pulse pressure. For example, when blood vessels have been hardened by arteriosclerosis, the change in blood vessel hardness can be identified because there is less deformation of blood vessels compared to the normal deformation against the same pulse pressure. Among the various kinds of blood vessel elasticity, the blood vessel elasticity Ep given by equation (1) below is frequently used to evaluate the degree of the arteriosclerosis of the blood vessels which are not extracted.

$$Ep = \Delta P / (\Delta D / D) \qquad (1)$$

where $\Delta P$ is pulse pressure, $\Delta D$ is the diameter of blood vessels and $\Delta D$ is the change in diameter in response to pulsation.

The blood vessel elasticity Ep given by the above equation (1) is applicable only when the cross-sectional shape of the blood vessels is considered to be circular. Therefore, true evaluation is not available in case of blood vessels with a changed shape On the contrary, the blood vessel elasticity Ep' obtained from the cross-sectional area of blood vessels is a useful standard which serve the evaluation of blood vessel hardness almost independently of the change in shape. The blood vessel elasticity Ep' can be expressed by equation (2) below where S is the cross-sectional area of blood vessels and ΔS is the change in the cross-sectional area of blood vessels in response to pulsation.

$$EP' = 2\Delta p/(\Delta S/S) \qquad (2)$$

Note that $Ep' = Ep/2$ in case of a cross-section which can be regarded to be circular.

The blood vessel elasticity Ep or Ep' is the elasticity dependent not only on the hardness of blood vessels but also on the thickness of blood vessel walls and it is not possible to evaluate the hardness of blood vessels themselves. In order to evaluate the hardness of blood vessels, it is required to obtain Young's modulus by measuring the thickness of blood vessel walls. If Young's modulus is available, it can be determined which causes the change in the hardness of blood vessels due to arteriosclerosis, the change in quality or thickness of blood vessels.

As blood vessel elasticity which is equivalent to Young's modulus, incremental elasticity Einc has been suggested. The incremental elasticity Einc can be calculated by equation (3) below where the thickness of blood vessel walls is represented by h.

$$Einc = Ep (1-\delta^2)/(2h/D) \qquad (3)$$

In the above equation δ stands for Poisson's ratio which is 0.5 in incompressible blood vessels.

Thus, in order to obtain blood vessel elasticity, it is required to measure the diameter or cross-sectional area of a blood vessel, the change in the diameter or cross-sectional area in response to pulsation, the thickness of blood vessel walls and pulse pressure. These values shall be simultaneously measured at the same location and measurement of high sensitivity is required for the change in response to pulsation which is microscopic.

In the above ultrasonic method, however, the pulse pressure ΔP shall be substituted by the value measured at brachium using a cuff-type hemomanometer. The value will obviously be different from the pulse pressure at the location to be measured and therefore, the calculated blood vessel elasticity will include an error. Also, the measurement is limited to the location which can receive ultrasonic waves. Further, since the diameter of a blood vessel and change in the diameter in response to pulsation is measured using a part of the cross-section of the blood vessel, an error will result when the cross-section cannot be assumed to be circular.

A device to obtain the blood vessel elasticity using an intra-blood-vessel ultrasonic probe is disclosed in Japan Pat. Laid Open No. 63-317130.

This device enables to measure the pulse pressure at the location to be measured to obtain accurate blood vessel elasticity.

With this device, however, it is not possible to diagnose the shape of blood vessels because it does not provide cross-sectional images of blood vessels. Also, since this device cannot perform real-time measurement of the cross-sectional area of blood vessels, there is the same possibility of an error in the measurement of blood vessel elasticity as that in the non-invasive ultrasonic irradiation from the surface of the body in case of blood vessels with a changed shape.

SUMMARY OF THE INVENTION

It is an object of the present invention to provide an intra-blood-vessel ultrasonic diagnosis device which is suitable for overall diagnosis on blood vessels including information on blood vessels such as the cross-sectional and three-dimensional images of blood vessels and the cross-sectional area of blood vessels.

It is another object of the present invention to provide an intra-blood-vessel ultrasonic diagnosis device which can provide highly accurate blood vessel elasticity.

It is a further object of the present invention to provide an intra-blood-vessel ultrasonic diagnosis device which is beneficial to both operators and patients in that it provides many kinds of measurement data as desired in a short time.

This device comprises a portion which can be inserted into blood vessels and which has an ultrasonic probe with an incorporated ultrasonic oscillator for transmitting and receiving ultrasonic waves, a scan device for changing the direction of the transmission and reception of the ultrasonic waves, a transmission signal generating device for generating a signal to cause the transmission of ultrasonic waves, a blood vessel information calculating device for calculating information about the inner and outer walls of blood vessels based on the ultrasonic echo signals which it has received, a video signal processing device for generating video signals corresponding to cross-sectional images based on the ultrasonic echo signals and a display device.

BRIEF DESCRIPTION OF DRAWINGS

FIG. 1 through FIG. 25 relate to a first embodiment of the present invention.

FIG. 1 illustrates the overall configuration of an ultrasonic diagnosis device of the first embodiment.

FIG. 2 illustrates the end of an ultrasonic probe.

FIG. 3A and FIG. 3B are side views illustrative of the configuration of a flexible shaft driving system.

FIG. 5 is a block diagram illustrative of the configuration of a blood vessel information calculating circuit.

FIG. 6 is a block diagram illustrative of the configuration of a distance calculating circuit and a cross-section integrating circuit.

FIG. 7 is a block diagram illustrative of the configuration of a three-dimensional image processing circuit.

FIG. 8 is a timing chart illustrative of the operation of the circuit per FIG. 7.

FIG. 9 through FIG. 15 are illustrative of the function of the three-dimensional image processing circuit.

FIG. 16 is a block diagram illustrative of the configuration of a cross-sectional area ratio calculating circuit.

FIG. 17 is a timing chart illustrative of the circuit per FIG. 16.

FIG. 18 is illustrative of the function of the circuit per FIG. 16.

FIG. 19 is a flow chart illustrative of the contents of processing in the circuit per FIG. 16.

FIG. 20 and FIG. 21 illustrate that the ultrasonic probe can be inserted in a curved route by operating a flexible wire.

FIG. 22 illustrates that the end of the ultrasonic probe can be fixed within a blood vessel by operating the flexible wire.

FIG. 23 illustrates an example of a cross-sectional image displayed on a monitor.

FIG. 24 illustrates a blood vessel wall displayed on the monitor.

FIG. 26 illustrates the configuration of an ultrasonic diagnosis device according to the second embodiment.

FIG. 27 is a timing chart illustrative of the function of the device per FIG. 26.

FIG. 28 illustrates the configuration of an ultrasonic diagnosis device according to the third embodiment.

FIG. 29 is a timing chart for the device per FIG. 28.

FIG. 30 illustrates the configuration of an ultrasonic diagnosis device according to the fourth embodiment.

FIG. 31 illustrates that marking is being done with a light-pen.

FIG. 32 through FIG. 29 relate to a fifth embodiment of the present invention.

FIG. 32 illustrates the configuration of an ultrasonic diagnosis device according to the fifth embodiment.

FIG. 38 illustrates the configuration of the eighth embodiment of the present invention.

FIG. 39 is a timing chart illustrative of the device per FIG. 38.

FIG. 40 illustrates the procedure through which a cross-sectional area is obtained against the displayed cross-section of a blood vessel.

FIG. 41 illustrates that a measurement point is displayed on a display screen.

FIG. 42 through FIG. 45 relate to a ninth embodiment of the present invention.

FIG. 42 illustrates a driving system for an ultrasonic oscillator of the ninth embodiment.

FIG. 43 illustrates an ultrasonic probe which is being rotated and reciprocated within a blood vessel.

FIG. 44 illustrates the cross-sectional image which is obtained by the operation according to FIG. 43.

FIG. 45 illustrates a three-dimensional display of a blood vessel.

FIG. 46 illustrates the configuration of the tenth embodiment of the present invention.

FIG. 47 is a timing chart illustrative of the device per FIG. 46.

FIG. 48 illustrates that a cross-sectional image of a blood vessel is displayed.

FIG. 49 illustrates that a measurement point is displayed.

FIG. 55 illustrates the configuration of a sixteenth embodiment of the present invention.

FIG. 56 illustrates an ultrasonic probe.

FIG. 57 is an elevational view illustrative of an ultrasonic oscillator.

FIG. 58 is a perspective illustration of the head portion of an ultrasonic probe.

FIG. 59 illustrates the configuration of the seventeenth embodiment of the present invention.

FIG. 60 illustrates the configuration of the eighteenth embodiment of the present invention.

FIG. 61 is a flow chart illustrative of the contents of processing.

FIG. 62 illustrates a cross-sectional image of a blood vessel.

DETAILED DESCRIPTION OF PREFERRED EMBODIMENT

Figure 4A:
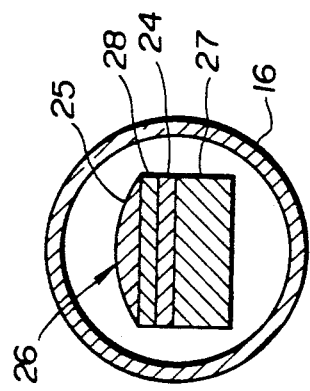
FIG. 4A and FIG. 4B are cross-sections illustrative of the configuration of an ultrasonic oscillator.

FIG. 1 shows an ultrasonic diagnosis device 1 according to the first embodiment.

An ultrasonic probe 5 comprises an ultrasonic oscillator 3 for transmitting and receiving ultrasonic waves and a pressure sensor 4 for measuring blood pressure incorporated in the end portion of a catheter 2 which is formed long and thin to be inserted into blood vessels.

An ultrasonic controller 13 is connected to the ultrasonic probe 5 and comprises a transmission signal generating circuit 6 for generating the transmission signal to cause the ultrasonic oscillator 3 to transmit ultrasonic waves. A reception signal processing circuit 7 processes the signals received by the ultrasonic oscillator 3. A blood vessel information calculating circuit 8 calculates the distance between inner surfaces and between outer surfaces of a blood vessel and the thickness of a blood vessel wall based on the output signal from the reception signal processing circuit 7. A cross-sectional image generating circuit 9 generates a cross-sectional image based on an output signal. A three-dimensional image generating circuit 10 generates a three-dimensional image based on the output signal. A pulse pressure calculating circuit 11 calculates pulse pressure based on the output signal of the blood pressure sensor 4. A blood vessel elasticity calculating circuit 12 calculates blood vessel elasticity based on the output signals of the pulse pressure calculating circuit 11 and blood vessel information calculating circuit 8.

A monitor 14 displays the video signal output from the cross-sectional image generating circuit 9 or three-dimensional image generating circuit 10.

At the head portion 16 of the ultrasonic probe 5 which is located at the top end of the catheter 2, the ultrasonic oscillator 3 is contained rotatably and movably in the axial direction B to the probe 5. As shown in FIG. 2, the top end portion 16 of the ultrasonic probe containing the ultrasonic oscillator 3 is covered by a cap 17 which is formed of a material transmitting ultrasonic waves, i.e. a material transparent to ultrasonic waves, and a liquid 18, for transferring ultrasonic waves, is filled around the ultrasonic oscillator 3 contained in the cap 17.

One end of a flexible shaft 19, penetrating the catheter 2 and containing a signal line, is connected to the base of the above ultrasonic oscillator 3, while the other end of this shaft 19 is fixed on a rotor side contact member 20a within a flexible shaft driver 30. This contact member 20a is fixed on the shaft of a motor 21 as a driving means for rotary motion. The motor 21 can be reciprocated in the axial direction B to the probe 5 by a linear motor 22.

Therefore, the ultrasonic oscillator 3 is rotated in the direction of rotation A to the flexible shaft by the motor 21, and thereby it radially transmits ultrasonic waves and receives the echo signals of the ultrasonic waves which have been transmitted in each direction. Thus, the motor 21 constitutes a driving means for radial scanning of ultrasonic waves. Also, the ultrasonic oscillator 3 is moved in the axial direction B to the flexible shaft 19 by the linear motor 22, and it transmits and receives ultrasonic waves in the direction normal to the axial direction B while it is being rotated. Thus, the linear motor 22 constitutes a driving means for linear scanning of ultrasonic waves.

It is possible to operate only one of the motors 21 and 22. The motors 21 and 22 can also be operated simultaneously. When they are operated simultaneously, ultrasonic waves are spirally transmitted. Each of the motors 21 and 22 is equipped with a encoder 21a and 21b respectively to detect the angle of rotation and the quantity of movement. As shown in FIG. 3A, the cable penetrated through the flexible shaft 19 is connected to a rotary contact P of the contact member 20, while the cable connected to the contact member 20b at the stator side is connected to the ultrasonic controller 13.

The structure as shown in FIG. 3B may be used instead of that shown in FIG. 3A. In this structure, a stepping motor 22' is used instead of the linear motor 22, the shaft of which is connected to the motor 21 through a ball screw 23. In this case, the motor 21 is moved back and forth depending on the rotation of the motor 22' in forward or reverse direction, and at the same time, the ultrasonic oscillator 3 at the head portion of the flexible shaft 19 is moved similarly.

Figure 4B:
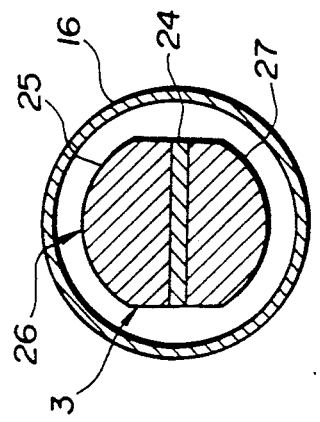

The structure of the ultrasonic oscillator is, for example, as shown in FIG. 4A or FIG. 4B.

In the ultrasonic oscillator shown in FIG. 4A, for example, electrodes are mounted on both sides of a plate-like piezoelectric element 24, on one face of which an acoustic lens 25 converging ultrasonic waves is mounted to form an ultrasonic receiving portion 26 for receiving ultrasonic waves, and on the other face of which a packing member 27 formed of a material attenuating ultrasonic waves is mounted. As shown in FIG. 4A, the structure formed by the acoustic lens 25 and packing member 27 is in a shape which substantially coincides with the shape of the inner circumference of the head portion 16 of the ultrasonic probe, and includes a space to pass the liquid for transmitting ultrasonic waves which is filled in the head portion 16 of the ultrasonic probe.

In the ultrasonic probe 3 shown in FIG. 4B, an acoustic lens 25 is mounted on one of the faces of the piezoelectric element 24 with an acoustic matching layer 28 interposed to form the receiving portion 26 while the packing member 27 is mounted on the other face of the piezoelectric element 24.

In this embodiment, a pressure sensor 4 is provided on the outer wall at the head portion of the catheter 2 as shown in FIG. 2. The pressure sensor 4 detects the pulse pressure of the blood vessel into which the catheter 2 is inserted and outputs pressure detection signal P (t) through a signal line 31. Three through holes 32 are provided on the outer wall of the catheter 2 in the axial direction. Each through hole 32 is exposed near the head of the catheter 2 in a predetermined length to form a groove portion 33. Within each through hole 32, a flexible wire 34 is provided, the end of which is connected to the catheter 2. Pushing the back end of each flexible wire 34 in the direction toward the head portion manually or by electromotive action causes the flexible wire 34 to project from the groove portion 33 in an appropriate length at which the wire is curved. The head portion of the catheter 3 can be bent by pulling the flexible wire in the direction of the back end thereof.

As shown in FIG. 1, the ultrasonic oscillator 3 is supplied with exciting pulses which are the ultrasonic exciting pulses from the transmission signal generating circuit 6 after amplification by a pulse driver 35 within the ultrasonic probe 5, and by which the transmission of ultrasonic waves is caused.

The transmitted ultrasonic waves are then reflected at the locations where the discontinuity of acoustic impedance exists and turned into ultrasonic echoes which are received by the ultrasonic oscillator 5 and converted into electrical signals i.e. ultrasonic echo signals. The echo signals are amplified by a preamplifier 36 within the probe 5 and input to a reception signal processing circuit 7 via the contact members 20a and 20b.

The timing for generation of the above exciting pulses is controlled by a timing controller 37.

Rotational angle signal $\theta$ from the encoder 21 detecting the angle of rotation of the motor 21, movement quantity signal Z from the encoder 22a detecting the quantity of movement caused by the motor 22 are input to the timing controller 37. The timing controller 37 controls the motors 21 and 22 through a motor servo circuit 38 so that there will be no advance or delay of signals $\theta$ and Z.

Figure 5:
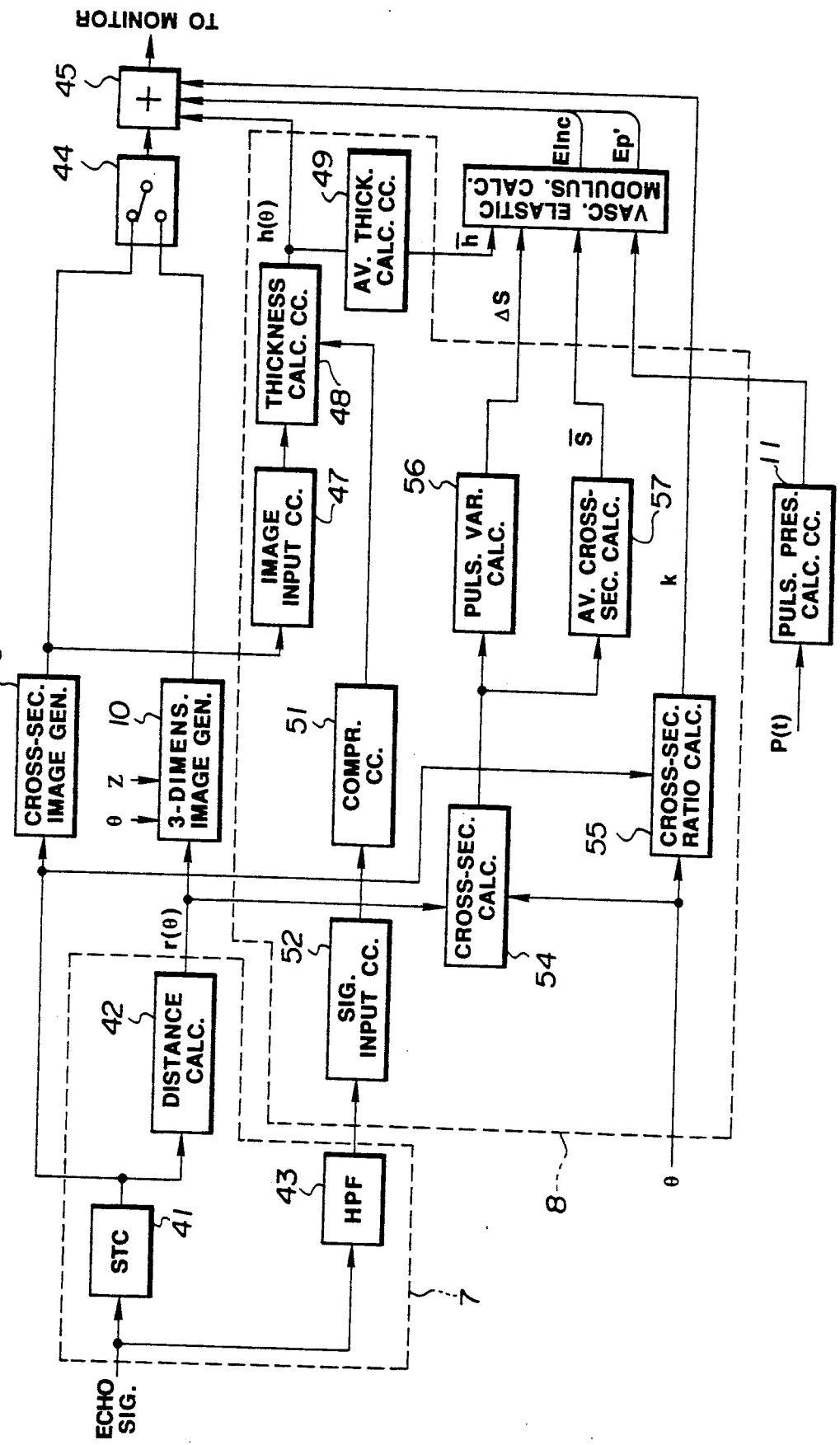

As shown in FIG. 5, the above reception signal processing circuit 7 comprises a STC circuit which performs Sensitivity Time Control (STC) processing, a distance calculating circuit 42 which calculates the distance between the ultrasonic oscillator 3 and inner walls of blood vessels and a high-pass filter 43 which generates RF echo signals.

Based on the ultrasonic echo signals which have received STC processing, the cross-sectional image generating circuit generates cross-sectional image signals which are sent to the monitor 14 to be displayed via a switch 44 and a mixer 45. The operation of the switch 44 can be controlled by a foot switch 44a.

The above cross-sectional image signal is input to a pulse-synchronous image input circuit 47 within the blood vessel information generating circuit 8 which supplies the cross-sectional image signal to a thickness calculating circuit 48 after synchronizing the signal with the pulses.

The thickness calculating circuit 48 generates a blood vessel wall thickness signal $h(\theta)$ by extracting signals for the blood vessel wall through processing the cross-sectional image signal, and outputs it to the monitor 14 via the mixer 45 on which the thickness of the entire blood vessel wall is displayed.

The blood vessel wall thickness signal h(θ) from the thickness calculating circuit 48 is also supplied to an average thickness calculating circuit 49. The average thickness calculating circuit 48 calculates the average thickness of a blood vessel wall using the blood vessel wall thickness signal h(θ) and outputs an average thickness signal h to an blood vessel elasticity calculating circuit 12.

The blood vessel thickness calculated by the thickness calculating circuit 48 through image processing becomes larger than the actual value due to expansion of the waveform of the ultrasonic echo. Taking this into consideration, a calibrating circuit 51 is provided in order to improve the accuracy of measurement.

The radio frequency component (referred to as RF echo signal) is supplied to the calibrating circuit 51 via the pulse-synchronous signal input circuit 52. The pulse-synchronous input circuit 52 synchronizes the RF echo signal with pulse and supplies it to the calibrating circuit 51. The calibrating circuit 51 operates on a theory which is similar to that of a normal ultrasonic thickness meter wherein it obtains the frequency spectrum of the RF echo signal and operates the thickness based on the intervals of the dips of the spectrum. The accuracy of the thickness measurement is greatly improved by correcting the operation of the thickness calculating circuit 48 using the output of the calibrating circuit 51.

The cross-sectional image signal is also supplied to a cross-sectional area ratio calculating circuit 55 within the blood vessel information calculating circuit 8 which calculates the ratio of the cross-sectional area K of a thrombus to the cross-sectional area of a blood vessel.

The distance calculating circuit 42 obtains a distance signal r(θ) by calculating the distance between the ultrasonic oscillator 3 and the inner wall of a blood vessel based on an input echo signal. The distance signal r(θ) is input to a three-dimensional image generating circuit 10 by which a three-dimensional image signal is generated and input, via the switch 44 and mixer 45, to the monitor 14 for displaying a three-dimensional image.

Also, the distance signal r(θ) is input to a cross-sectional area calculating circuit 54 in which a cross-sectional area signal S(t) is generated. The rotational angle signal from the encoder 21a is also input to this circuit.

The cross-sectional area signal S(t) is input to a pulsant change calculating circuit 56 and an average cross-sectional area calculating circuit 57. The pulsant change calculating circuit, which comprises a high-pass filter, calculates the change in cross-sectional area i.e. the change ΔS which is dependent on pulsation, and outputs it to the blood vessel elasticity operating circuit 12. The average cross-sectional area calculating circuit 57, which comprises a low-pass filter, calculates the average cross-sectional area S which is the average value of the cross-sectional area of a blood vessel, and outputs it to the blood vessel elasticity calculating circuit 12.

The cross-sectional area ratio signal k is output to the monitor 14 via the mixer 45 and the ratio k of the cross-sectional area of a thrombus to the cross-sectional area of a blood vessel is displayed on a screen of the monitor 14.

The pulse pressure ΔP output from the pulse pressure calculating circuit 11 is input to the blood vessel elasticity calculating circuit 12 and input to a pulse pressure signal generating circuit 59.

The blood vessel elasticity calculating circuit 12 to which the average blood vessel thickness $\bar{h}$, the average cross-sectional area $\bar{S}$, the pulsant change ΔS of the cross-sectional area and the pulse pressure P have been supplied carries out the calculation as given by the forementioned equations (2) and (3) to obtain blood vessel elasticity Ep' and Einc.

The blood vessel elasticity Ep' and Einc are input to the monitor 14 via the mixer 45 and those values are displayed on the screen of the monitor.

The pulse pressure signal generating circuit 59 generates a pulse synchronizing signal based on the maximum quantity of the change in the pulse pressure ΔP, and outputs it to a pulse-synchronous image input circuit 47 and the pulse-synchronous signal input circuit 52.

Figure 6:
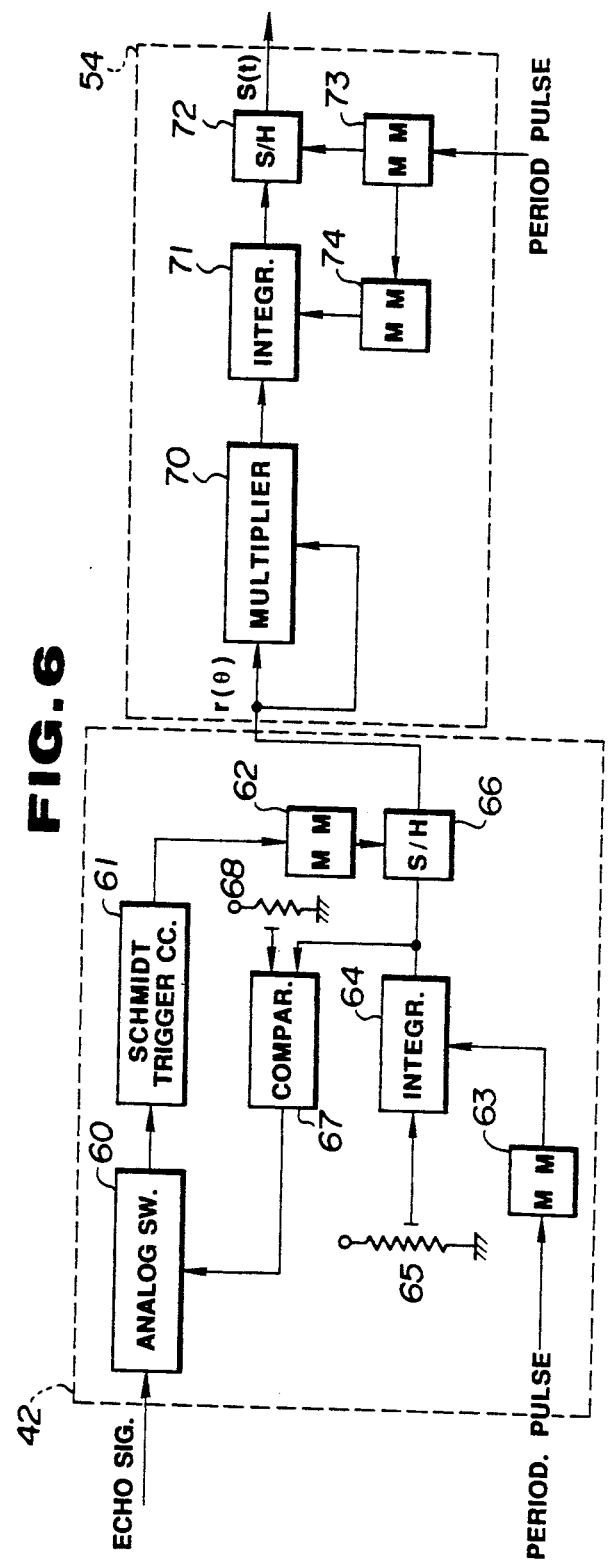

FIG. 6 illustrates a specific configuration of the distance calculating circuit 42 and cross-sectional area calculating circuit 54.

The echo signal is supplied to a monostable multivibrator 62 (referred to as MM hereinafter) via an analog switch 60 and a Schmitt trigger circuit 61. Meanwhile, a synchronizing pulse which is in synchronization with the operation of the ultrasonic oscillator 3 is supplied to an integrator 64 via the MM 63. The integrator 64 uses this signal as a reset signal and integrates a constant voltage supplied by the sliding edge of a variable resistor 65. This integration output is supplied to a sample-hold circuit 66 and a comparator 67. The comparator 67 has a predetermined constant voltage supplied by the sliding edge of a variable resistor 68 and it outputs a signal for turning an analog switch on at a predetermined time after the input of the synchronizing pulse, thereby preventing a probe multiecho signal, which occurs within a relatively short period after ultrasonic transmission, from passing the analog switch 60.

An echo signal from the inner wall of a blood vessel, which has passed the analog switch 60, receives a waveform shaping by the Schmitt trigger circuit 61 and is supplied to the sample-hold circuit 66 via the MM 62. The sample-hold circuit 66 receives a voltage varying in time supplied by the integrator 64 which is sampled and held depending on the timing of the signal supplied by the MM 62. Thus, the sample-hold circuit 66 outputs the distance signal r (θ) representing the distance between the ultrasonic oscillator 3 and the inner wall of a blood vessel.

The cross-sectional area calculating circuit 54 comprises a multiplier 70, an integrator 71, a sample-hold circuit 72, MMs 73 and 74. When a curve formed by the inner wall of a blood vessel is expressed using polar coordinates (r,θ), the area enclosed by the curve and radius vector of θ=0, 2π, i.e. the cross-sectional area S(t) of the blood vessel can be expressed by equation (4) below.

$$S(t) = \frac{1}{2} \int_0^{2\pi} r_2(\theta)d\theta \qquad (4)$$

The multiplier 70 receives the distance signal r(θ), i.e. the curve formed by the inner wall of a blood vessel, from the sample-hold circuit 66 which is squared and supplied to the sample-hold circuit 73 via the integrator 71. Meanwhile, a periodic pulse which is in synchronization with one cycle of the ultrasonic oscillator 3 is supplied to the sample-hold circuit 72 via the MM 73. The sample-hold circuit 72 samples and holds the output of the integrator 71 during one cycle of the ultrasonic oscillator. The output of the MM 73 is supplied to the integrator as a reset signal via the MM 74 while the periodic pulse is delayed by the MM 73 and MM 74 and supplied to the integrator 71 by which the factor ½ in the above equation (4) is given. Thus, the cross-sectional area S(t) as expressed by the above equation (4) is output from the sample-hold circuit 72. Since the ultrasonic oscillator rotates at high speed more than 30 rotations/second, the output of the sample-hold circuit 72 can sufficiently follow the change in the cross-sectional area in response to pulsation enabling highly accurate measurement of the same.

The configuration of the three-dimensional image generating circuit 19 will be described with reference to FIG. 7. In this figure, the pulse driver 35 and transmission signal generating circuit 6 in FIG. 1 are referred to as a pulser 81. Also, the preamplifier 36 and the STC circuit within the reception signal processing circuit 7 are referred to as an amplifier 82.

The timing controller 37 outputs a trigger 8A shown in FIG. 8 to the pulser 81 to drive it. The trigger 8A is also output to a first gate 82. The pulse output of the trigger 81 drives the oscillator 3 thereby causing transmission of an ultrasonic wave. The transmitted ultrasonic wave is reflected at a location where the discontinuity of acoustic impedance exists, such as a blood vessel wall, and then received by the ultrasonic oscillator 3 to become an electrical signal, i.e. an ultrasonic echo signal. This echo signal is amplified by the amplifier 82 resulting in a signal having the waveform as indicated by 8B in FIG. 8 which is input to the first gate 83.

Since the gate 83 eliminates the influence of the signal from the pulser 81 and the multiecho of the probe 5, a gate 8C is generated, which cuts off reception signals for a arbitrary period after pulse driving.

Therefore, since the multiecho signal in the input echo signal 8B is cut off by the gate 83, the echo signal output by the gate 83 will be as indicated by 8D in FIG. 8. The signal 8D is input to a comparator 84 to be compared to a reference level Vref, and converted into a binary value which is "H" if it is greater than the reference level Vref, and "L" if it is smaller than the Vref (8E of FIG. 8).

The binary signal is input to a second gate 85 and a counter 86 which counts the number of "H" pulses and which controls the switching of the gate, when it has counted a pulse so that no pulse will pass the gate 85 thereafter (See 8F of FIG. 8). Therefore, the output signal from the gate 85 is as indicated by 8G of FIG. 8, and the circuit up to the gate 85 is a circuit in which as soon as a signal greater than Vref is input no further signal is accepted, that is a circuit for detecting the first falling edge.

A plane P1 as shown in FIG. 9 can be obtained by processing signals in the signal processing system 81 through 85 for each radial scan.

Planes P1 through P3 can be obtained by performing a linear scan each time when one rotation is made for a radial scan and processing the signal thus obtained in the above signal processing system. The planes P1 through P3 are stored in a frame memory as shown in FIG. 7 in correspondence to the rotational angle signal θ and the linear quantity of movement Z.

Performing a radial scan and a linear scan simultaneously results in a spiral scan which provides a stereoscopic image as shown in FIG. 11.

As shown in FIG. 11, when a spiral scan is performed, it is assumed that scan in the radial direction is only for one line or a few lines for the plane corresponding to the plane 1 indicated by a, b, c and d in FIG. 9. However, when the quantity Z of the movement in the linear direction is small, it can be assumed that the linear scan is performed on the same plane. Therefore, in FIG. 11, the data stored in the frame memory 87 can be regarded as the P1 through P3, the first falling edge of which have been detected as shown in FIG. 10.

The data of the falling edge in the frame memory 76 is stored with the address of a two-dimensional memory shifted slightly in the X direction and Y direction which is normal to the X direction.

The image shown in FIG. 10 will not be formed in a continuous three-dimensional image because the intervals in the sampling in the Z direction is larger than that in the X and Y directions.

Figure 12:
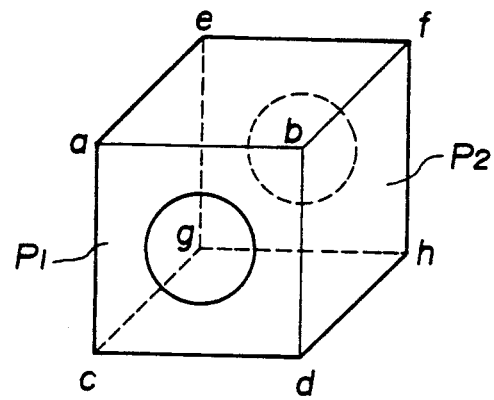
Figure 13:
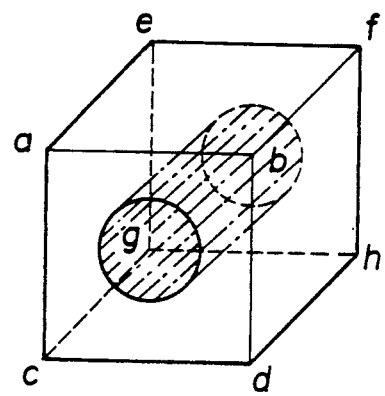

As shown in FIG. 13, interpolation is carried out between the edge lines of two adjoining edge images P1 and P2 which have been stored in the frame memory 87 as shown in FIG. 12.

Interpolation between the edges of the P1 and P2 planes is performed by a interpolation circuit 88 as shown in FIG. 7 which regards the edge of P1 as substantially circular and calculates the center of the circle and the average radius r from each point.

Also each point of the edge of the P2 plane corresponding to the edge of the P1 plane can be obtained by calculating the center and average radius from the edge of the P2 plane, and thus a line can be stretched between the edges.

Figure 14:
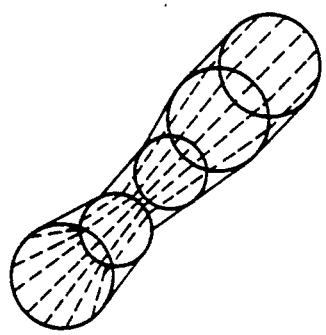

After interpolation operation through repetition of the above steps, the result of the interpolation is stored in the frame memory 87. For example, if P1 through P5 are available, a three-dimensional image as shown in FIG. 14 can be formed.

Figure 15:
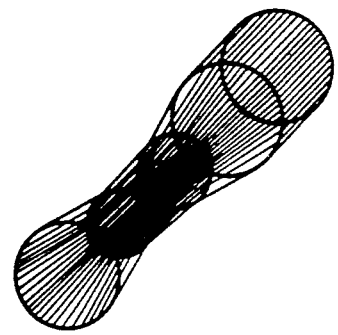

Also, increasing the number of lines enables surface interpolation as shown in FIG. 15. The images as shown in FIG. 14 and FIG. 15 are stored in the frame memory 87 and output to the monitor 14 via the switch 45 etc. for displaying three-dimensional images.

Thus, the formation of a three-dimensional image using interpolation enables to understand the shape of the inner wall of a blood vessel at a glance and thereby providing a very effective means for diagnosis.

The structure of the cross-sectional area ratio operating circuit 55 will be described with reference to FIG. 16.

The echo signal which has passed the STC circuit 41 is input to a gate 91. This echo signal is as shown in FIG. 17B. FIG. 17A shows a pulse which drives the ultrasonic oscillator 3 (The pulse is the output of the pulser 81 in FIG. 8 or the output of the pulse driver 35.). As shown in FIG. 17C, the gate 91 closes the gate for a predetermined period after the rising edge of the pulse. Therefore the signal which has passed this gate 91 is as shown in FIG. 17D. The signal which passed the gate 91 are input to comparators 92 and 93 to which reference voltages Vr1 and Vr2 are supplied respectively. When the signal exceeds the reference voltage Vr1 or Vr2, an "H" pulse is output as shown in FIG. 17E and FIG. 17F. The reference voltages Vr1 and Vr2 are set at a level which is to detect an echo signal coming back from a thrombus or blood vessel wall.

The pulse outputs from the above comparators 92 and 93 are applied to reset terminals of MM 94 and MM 95 respectively. A driving pulse is applied to a trigger terminal of each of MM 94 and 95 which, as shown in FIG. 17G and FIG. 17H, outputs an "H" pulse from the output terminal until it is reset by the driving pulse. The width of these pulses corresponds to the distance from the ultrasonic oscillator 3.

The outputs from the MM 94 and MM 95 are applied to count enable terminals of counters 96 and 97 respectively which count clock while the pulse is "H". The counts of the counters 96 and 97 are input to an arithmetic circuit 98. If the counts of the counters 96 and 97 are put as C1($\theta$) and C2($\theta$) respectively, the arithmetic circuit 98 calculates $(C1(\theta)/C2(\theta))^2$ for each radial scan, accumulates the obtained value, and after one rotation, divides the accumulated value by 360 obtaining a cross-sectional area ratio which is output to the monitor 14 via a mixer 46. The counters 96 and 97 is reset, for example, by a reset pulse immediately before the driving pulse.

FIG. 18 shows how to obtain a cross-sectional area ratio. As shown in FIG. 18a, ultrasonic waves are transmitted and received with the ultrasonic oscillator 3 being turned at a very small angle $\Delta\theta$ around an origin 0 within the ultrasonic oscillator 3.

When l1 and l2 stand for the distance from the origin 0 to an inner wall 101 of a blood vessel and to the boundary Bo between blood and a thrombus respectively, while t1 and t2 stand for the time until echo signals return from the boundary Bo and the inner wall 101 respectively, the relationship between them can be expressed as follows.

$$l2/l1 = t2/t1$$

When S1 and S2 stand for the area of a region A1 inside the inner wall 101 and the area of a region A2 inside the boundary Bo respectively within the small angle $\Delta\theta$, the ratio of S1 to S2 is expressed as follows.

$$S2/S1 = \Delta\theta(l2)^2/\Delta\theta(l1)^2$$
$$= (l2/l1)^2$$

The same ratio when the angle $\Delta\theta$ is 360°, i.e. the ratio k of the A1 to A2 is expressed as follows.

$$k = S2/S1 = \int (l2/l1)^2 d\theta$$

If the angle $\Delta\theta$ is 1°, the ratio is as follows.

$$S2/S1 = \Sigma(l2/l1)^2/360$$

Therefore, the area ratio k can be obtained by accumulating the square of the counts C1 and C2 of the two counters 96 and 97 respectively by 360 times, and dividing the accumulated value by 360 with the arithmetic circuit 98.

Figure 19:
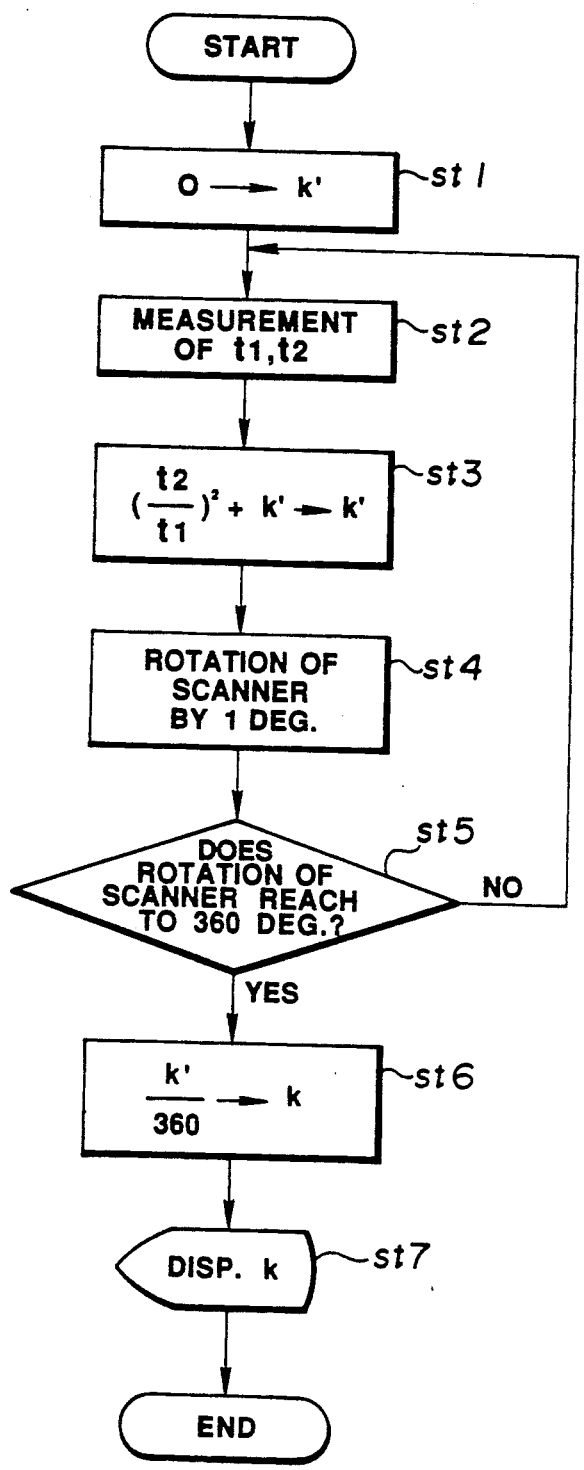

FIG. 19 shows the contents of a process to calculate the area ratio k and to display it on the monitor 14.

When the display operation is initiated, the value of a area ratio parameter k' of the arithmetic circuit 98 is set to 0 at the step st1. The time t1 and t2 are measured at step st2. The counts C2 of the counter 97 and the count C1 of the counter 96 correspond to the times t1 and t2 respectively. At step st2, calculation of t1 and t2 which satisfies $(t2/t1)^2 + k' = k'$ is performed (k' is 0 for the first time and k' is other than 0 for the second time and thereafter.). At step st3, the ultrasonic oscillator 3 is turned by 1° by the motor 21. Step st5 is to determine whether the ultrasonic oscillator 3 has been turned 360° or not. The steps st2 through st4 are repeated until the oscillator is turned 360°. When the steps st2 through st4 have been completed for the angle 360°, step st6, to divide the parameter k' by 360, is carried out to obtain the area ratio parameter k which is displayed on the monitor 14 at step st7 which completes the process.

It is possible to detect hemadostenosis using the value of the area ratio parameter k. Also, there is a clinical report that even after dilating the portion suffering from hemadostenosis with a balloon dilator, a high recurrence rate is observed with the k at a certain value, for example the value less than 25%. Thus, the value k provides valuable information to determine the possibility of the recurrence of hemadostenosis.

Next, the operation of such an ultrasonic diagnosis device will be described with reference to the other drawings.

Figure 22A:
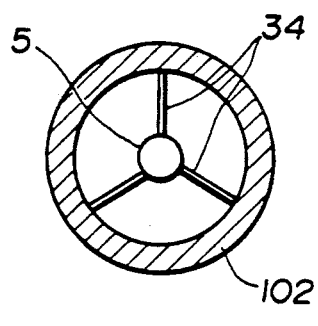
Figure 22B:
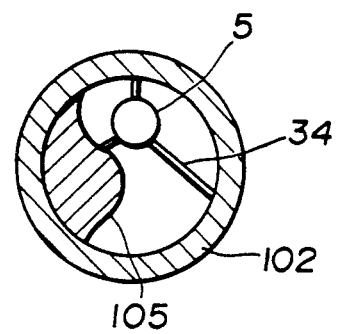

Firstly, the ultrasonic probe 5 as shown in FIG. 2 is inserted into a blood vessel. In case of a blood vessel having a branch as the blood vessel 102 in FIG. 20, the direction of the head portion of the probe 5 can be changed to facilitate insertion by pulling an appropriate flexible wire 34. Pushing the flexible wire 34 within a through hole 32 of the ultrasonic probe 5 enables flexible wires 32 to project from groove portions 33 as shown in FIG. 21. The catheter 2 is supported by the projected flexible wires. The back ends of the flexible wires 32 are pushed when the probe 5 has reached the location to be measured. For example, in case the shape of the blood vessel is substantially circular as shown in FIG. 22a, the catheter 2 is supported at a position in the center of the blood vessel by pushing the inner wall of the blood vessel with the projected portion of each flexible wire 32 which is projected in the same amount. Also, for example, in case plaque 105 is formed on a part of a blood vessel as shown in FIG. 22b, the catheter 2 is positioned near the plaque 105 by adjusting the projection of each flexible wire 27. This facilitates the observation of plaque 105 enabling effective diagnosis.

The ultrasonic oscillator 3 is reciprocated spirally within the head portion 16 of the ultrasonic probe 3 by operating a flexible shaft driver 30 while ultrasonic pulses are provided via a signal line to cause ultrasonic waves to be transmitted from the ultrasonic probe 3 toward the inner wall of the blood vessel. The ultrasonic probe 3 receives an echo from the location to be observed and outputs an echo signal to the distance calculating circuit 42 and cross-sectional image generating circuit 9 (See FIG. 5.).

Figure 23:
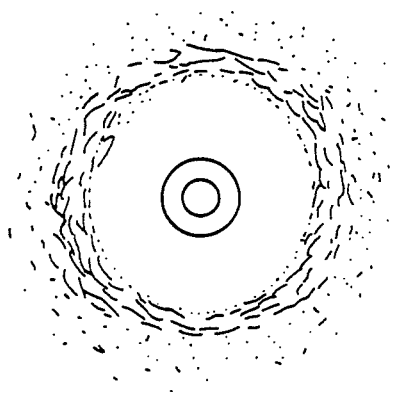
Figure 24:
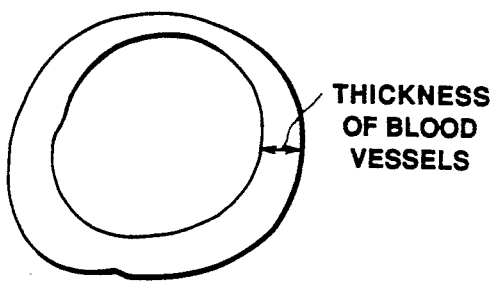

The cross-sectional image generating circuit 9 generates a cross-sectional image signal for the blood vessel based on the echo signal. The cross-sectional image signal is input to the monitor 14 on the screen of which a cross-sectional image as shown in FIG. 23 is displayed. The cross-sectional image signal is supplied to the thickness calculating circuit 48 via pulse-synchronous image input circuit 47. The thickness calculating circuit 48 outputs a blood vessel thickness signal h($\theta$) representing the thickness of a blood vessel without influence of the pulse to the monitor 14. Thus an enlarged display of the blood vessel thickness appears on the screen of the monitor 14. Also, the change in the blood vessel thickness in response to pulsation can be displayed on the monitor 14 by supplying the thickness calculating circuit 48 with the cross-sectional image signal in synchronization which is being varied by the pulse-synchronous image input circuit 47. The output of the thickness calculating circuit 48 is supplied to the average thickness calculating circuit 49 from which the average thickness h of a blood vessel wall is supplied to the blood vessel elasticity calculating circuit 12.

Figures 25A, 25B:
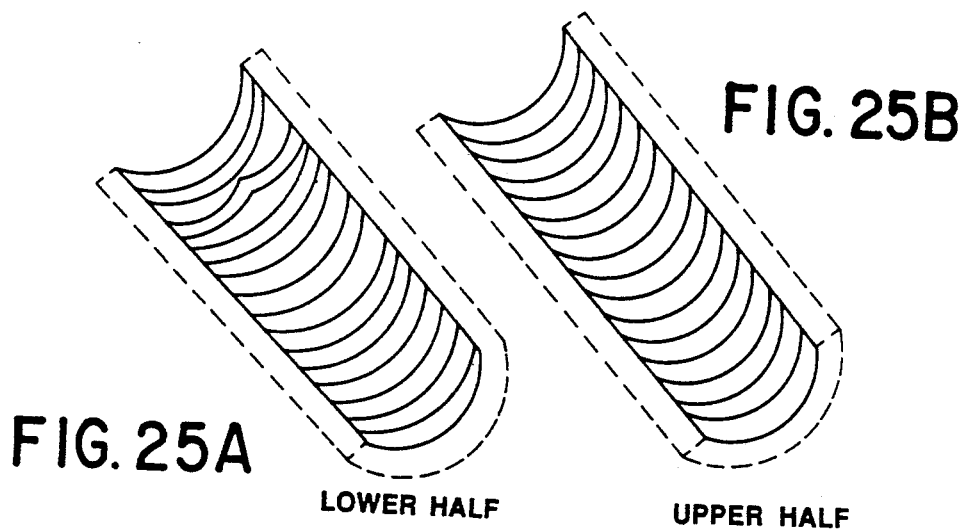
FIGS. 25(a)–25(b) illustrate inner walls of a blood vessel displayed on the monitor using an wire frame.

The distance signal r(θ) from the distance calculating circuit 42 is also supplied to the three-dimensional image generating circuit 10. The three-dimensional image generating circuit 10 is also supplied with the rotational angle and the position Z in axial direction of the ultrasonic oscillator 3. This circuit supplies the image signal to the monitor 14 sequentially in correspondence to the rotary and reciprocal motion of the ultrasonic oscillator 3. Based on this three-dimensional image signal, the monitor 14 performs real-time display of the three-dimensional images of the line frame as shown in FIG. 14 and FIG. 25, for example, sequentially from the line frame at the head portion of the probe 5 to that at the back end portion. In FIG. 25, the blood vessel is divided into upper and lower portions in displaying it to make the image clearer. Also, the three-dimensional image generating circuit 10 can output image signals with brightness which is varied depending on the strength of echo signals. The three-dimensional image generating circuit 10 can display realistic images on the screen using shading.

On the other hand, the distance signal r(θ) from the distance calculating circuit 42 is also supplied to the cross-sectional area calculating circuit 54. The cross-sectional area calculating circuit 54 obtains the cross-sectional area of a blood vessel by carrying out the calculation expressed by the forementioned equation (4). The cross-sectional area signal S(t) is supplied to the pulsant change calculating circuit 56 and average cross-sectional area calculating circuit 57. The pulsant change calculating circuit 56 calculates the average value $\bar{S}$ of the cross-sectional area of a blood vessel and supplies it to the blood vessel elasticity calculating circuit 12. The pressure sensor 12 provided near the head portion of the catheter 2 detects the pulse pressure within a blood vessel and supplies it to the pulse pressure calculating circuit 11. The pulse pressure calculating circuit 11 calculates pulse pressure ΔP and supplies it to the blood vessel elasticity calculating circuit 12. Thus, the blood vessel elasticity calculating circuit 12 is supplied with the average thickness h of a blood vessel, the pulsant change S of the cross-sectional area of a blood vessel, the average thickness S of the cross-sectional area of a blood vessel and the pulse pressure ΔP, based on which the blood vessel elasticity calculating circuit 12 obtains the blood vessel elasticity Ep' and Einc by carrying out the calculation as expressed in the forementioned equations (2) and (3).

The ratio k of the cross-sectional area of a thrombus to the cross-sectional area of a blood vessel is calculated by the cross-sectional area ratio calculating circuit 55 and displayed on the monitor 14.

In this embodiment, a quantitative measurement of various values such as the cross-sectional area of a blood vessel, the thickness of a blood vessel wall, the pulsant change in them and the smoothness of a blood vessel wall are performed in addition to formation of the cross-sectional image of the shape of a blood vessel. This embodiment provides a lot of information in one cycle of clinical inspection enabling overall diagnosis. The intra-blood-vessel method is an invasive inspection method wherein the burden to patients may be significantly reduced if this embodiment is used.

This embodiment obtains the three-dimensional image of a blood vessel in real-time. Therefore, it is very easy to verify the location to be measured and understand the shape of a blood vessel. This embodiment may be also used for the operation of a blood vessel.

Further, as a supporting mechanism for the catheter 2, flexible wires 32 are provided. The flexible wires 32 prevent the vibration of the catheter 2 and enable placement of the catheter 2 at the center of a blood vessel or at the optimal position near a location to be observed. Thus, the quality of the image displayed on the monitor 14 is improved and diagnosis will be quite easy. In case the catheter supporting mechanism comprising flexible wires 32 is provided on a catheter for operation of blood vessels, operability and safety during the operation will be greatly improved because the positioning of the catheter is easy.

The pressure sensor 4 is provided near the head portion of the ultrasonic probe within the catheter 2 for operating blood vessel elasticity from the pulse pressure near the location to be observed. This enables highly accurate measurement. In addition, in operation of blood vessel elasticity, the cross-sectional area and the change in the cross-section area of a blood vessel have been obtained by the cross-sectional area calculating circuit 54. This greatly improves the accuracy of measurement of blood vessel elasticity when compared to the prior art. Especially, most patients who need intra-blood-vessel inspection suffer from the abnormality of blood vessel shape. The blood vessel elasticity obtained by this embodiment is quite effective for such an inspection.

Briefly, this embodiment which provides measurement of dynamical characteristics of a blood vessel as well as the qualitative and quantitative measurement of the shape of a blood vessel is quite effective in clarification of pathology of various blood vessel diseases.

The average cross-sectional area of a blood vessel or the average thickness of a blood vessel wall may be obtained by taking the average for a pulse period.

Figure 26:
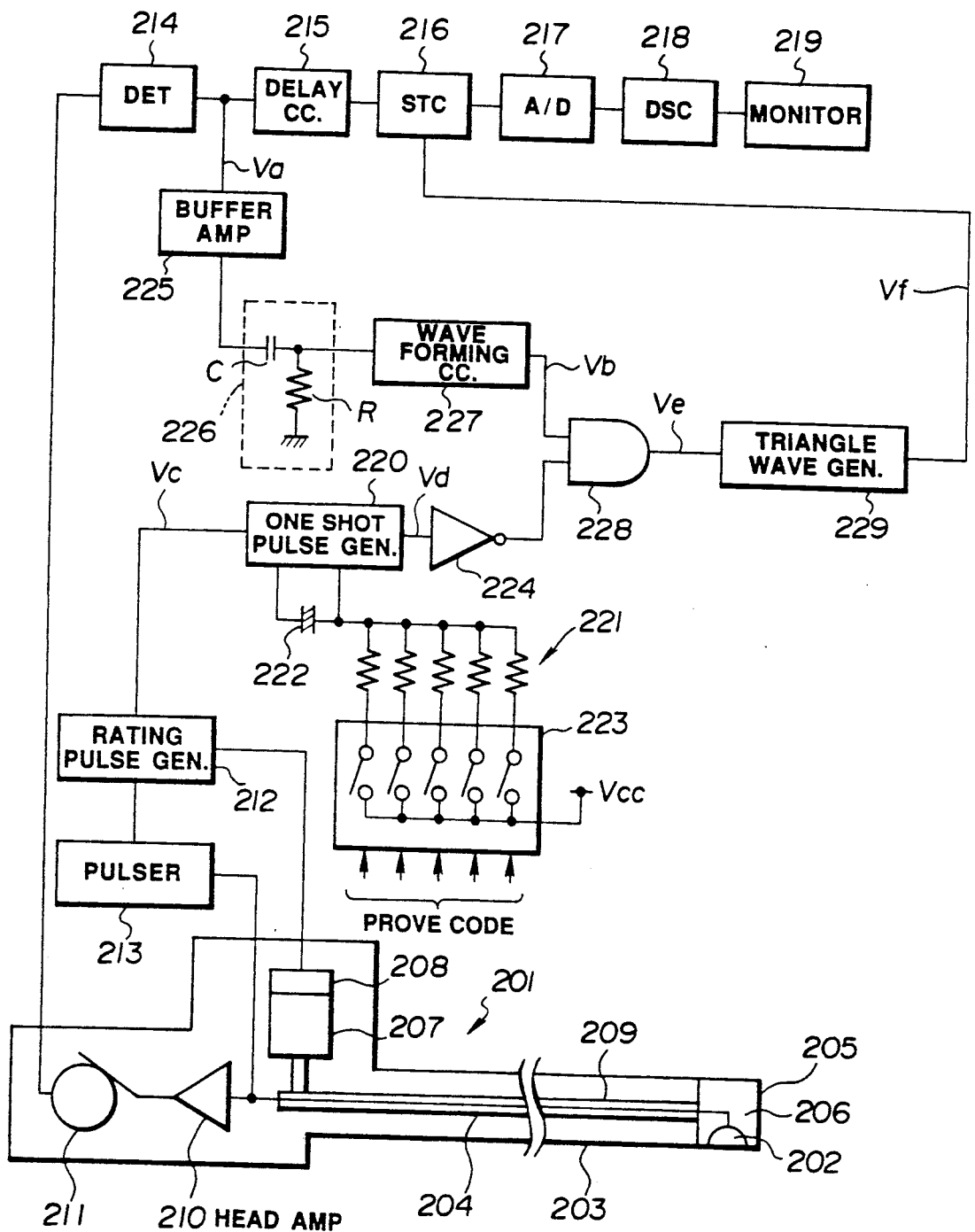
FIG. 26 and FIG. 27 relate to a second embodiment of the present invention.

FIG. 26 shows an ultrasonic diagnosis device according to the second embodiment of the present invention. In this embodiment, it is intended to enable signal processing suitable to the detection of an echo signal from the location to be observed such as the inner wall of a blood vessel by preventing the STC circuit from being affected by an echo having a large amplitude such as the echo from the cap at the head portion.

As shown in FIG. 26, the ultrasonic diagnosis device comprises an ultrasonic oscillator (referred to as oscillator hereinafter) 202 for transmitting and receiving an ultrasonic wave. An ultrasonic probe (referred to as probe hereinafter) 201 on which the oscillator 202 etc. are provided. A rate pulse generator 212 generates a predetermined pulse wave using an encoder 208 which will be described later. A pulser 213 drives the oscillator 202 based on the pulse wave from the gate pulse generator 212. A wave detector 214 detects an echo received by the oscillator 202. A delay circuit 215 delays the output signal from the wave detector 214. STC 216 is a voltage variable amplifier. An A-D converter 217 converts the analog signal of the STC 216 into a digital signal. A digital scan converter (referred to as DSC hereinafter) 218 converts the signal of the A-D converter 217 into a video signal. A monitor 219 displays the video signal of the DSC 218. A buffer amplifier 224 buffers the signal of the wave detector 214. A differentiator 226 comprises a capacitor C and a resistor R for differentiating the signal of the buffer amplifier 225. A waveform shaping circuit 227 shapes the waveform of the output signal of the differentiator 226. A one-shot pulse generator 220 generates a predetermined pulse based on the pulse of the rate pulse generator 212. A group of resistors 221 and a capacitor 222 set the width of the pulse from the one-shot pulse generator 221. A multiplexer 223 selects the group of resistors 221. An inverter 224 inverts the output logical value of the one-shot pulse generator 220. An AND circuit 228 carries out the logical AND between the waveform shaping circuit 227 and inverter 224. A sawtooth wave generating circuit 229 generates a sawtooth wave to control the STC 216 based on the output signal of the AND circuit 228.

The probe 201 has a insert portion 203 which is formed, for example, long and thin. At the head portion of the insert portion 203, there is provided a head cap 205 which is filled by a ultrasonic transmitting medium 206 including the oscillator 202. A flexible shaft 204 having a signal line 209 provided therein is provided within the insert portion 203. At the base portion of at operator side, there are provided a head amplifier 210 for amplifying a reception signal from the oscillator. A slip ring 211 transmits the output of the head amplifier 210 externally. A motor 207 drives the flexible shaft 204 in a rotary motion. An encoder 208 generates a synchronizing signal and is mounted on the motor 207. The head cap 205 is constructed so that it will not injure an organ in the body cavity with the oscillator 202, and the ultrasonic transmitting medium 206 is for transmitting an ultrasonic wave within the body cavity efficiently.

The oscillator 202 is connected to the input terminal of the head amplifier 210 and the output terminal of the pulser 213 via the signal line 209.

The output terminal of the head amplifier 210 is connected to the input terminal of the wave detector 214 via slip ring 211, and the output terminal of the wave detector 214 is connected to the input terminals of the delay circuit 215 and the buffer amplifier 225.

The output terminal of the delay circuit 215 is connected to the signal input terminal of the STC 216, and the output terminal of the STC circuit 216 is connected to the A-D converter 217. The output terminal of the A-D converter 217 is connected to the input terminal of the DSC 218, and the output terminal of the DSC 218 is connected to the input terminal of the monitor 219.

The output terminal of the buffer amplifier 225 is connected to the input terminal of the differentiator 226, and the output terminal of the differentiator 226 is connected to the input terminal of the waveform shaping circuit 227. The output terminal of the waveform shaping circuit 228 is connected to the first input terminal of the AND circuit 228.

The output terminal of the encoder 207 is connected to the input terminal of the rate pulse generator 212. The rate pulse generator 212 has the first output terminal connected to the input terminal of the pulser 213 and the second output terminal connected to the trigger terminal of the one-shot pulse generator 220.

Both terminals of the capacitor 222 are connected to the one-shot pulse generator 220. One of the terminals of the capacitor 222 is connected to the group of resistors 221 which is connected to a power source (VCC) via the multiplexer 223.

The output terminal of the one-shot pulse generator 220 is connected to the input terminal of the inverter 224, and the output terminal of the inverter 224 is connected to the second input terminal of the AND circuit 228.

The output terminal of the AND circuit 228 is connected to the trigger terminal of the sawtooth wave generating circuit 229, and the output terminal of the sawtooth wave generating circuit 229 is connected to the control input terminal of the STC 216.

The operation of the ultrasonic diagnosis device having the above configuration will be described.

The oscillator 202 is rotated by the flexible shaft 204 which is rotated by the motor 207.

The encoder 208 is provided on the motor 207. The motor 207 causes the encoder 208 to generate a synchronizing signal (A-phase).

The synchronizing signal is input to the rate pulse generator 212.

The rate pulse generator 212 generates a trigger pulse based on the synchronizing signal and outputs it to the pulser 213 and one-shot pulse generator 220.

The pulser 213 is a switching circuit comprising, for example, a FET and outputs a driving signal synchronized with the trigger pulse to the oscillator 202.

The driving signal is transmitted to the oscillator 202 via the signal line 209, and thus an ultrasonic wave is transmitted inside the body cavity.

The ultrasonic wave transmitted in the manner described above is reflected within the body cavity and is received by the oscillator 202 where it becomes an echo signal and is transmitted to the head amplifier 210 via the signal line 209.

The head amplifier 210 amplifies the transmitted echo signal and outputs it to the wave detector 214 via the slip ring 211.

The wave detector 214 detects the input echo signal and outputs it to the delay circuit 215 and buffer amplifier 225.

The delay circuit appropriately delays the input signal and outputs it to the STC 216.

The buffer amplifier 225 carries out, on the input signal, an amplification which establishes a non-dense relationship between the input signal and the output signal, that is buffer amplification, and outputs the output signal to the differentiator 226.

The differentiator 226 differentiates the input signal, in other words, it detects a portion in the input signal where an abrupt change exists and outputs the signal to the waveform shaping circuit 227.

The waveform shaping circuit 227 rectifies the input signal into, for example, a rectangular waveform and outputs the shaped signal to the first input terminal of the AND circuit.

Meanwhile, the one-shot pulse generator 220 is caused to generate a pulse signal having a predetermined pulse width by the trigger pulse from the rate pulse generator 212. The pulse width is determined by the resistance of the group of resistors 221 connected to the power source (VCC) via the multiplexer 223 and the value of the capacitor 222.

To the multiplexer 223, a probe type signal is input from the probe 201 via a signal line which is not shown, and then multiplexer 223 selects a predetermined resistor from the group of resistors 221 based on the probe type signal.

Therefore, the rate pulse generator 212 generates a pulse width which corresponds to the type of the probe 201.

As previously mentioned, the pulse wave generated by the rate pulse generator 212 undergoes the inversion of the logical value by the inverter 224 and is input to the second input terminal of the AND circuit 228.

The AND circuit 228 outputs a trigger signal to the sawtooth wave generating circuit 229. The trigger signal is the logical AND between the output signal of the waveform shaping circuit 227 input to the first input terminal thereof and the output signal of the inverter 224 input to the second input terminal thereof.

The sawtooth wave generating circuit 228 generates a sawtooth wave upon the trigger signal input as described above and outputs it to the STC 216.

The STC 216 amplifies the wave-detected echo signal input from the delay circuit 215 with amplification degree being varied depending on the saw-tooth wave of the sawtooth wave generating circuit 229 and outputs the amplified signal to the A-D converter 217.

The A-D converter 217 converts the analog output signal of the STC 216 into a digital signal and outputs it to the DSC 218.

The DSC 218, to which signals such as the scan signal of the oscillator 202 and the synchronizing signal for the monitor 219, which are not shown, are input, converts the signal of the A-D converter 217 into a video signal and outputs it to the monitor 219, thereby causing the monitor 219 to display an ultrasonic image for observation.

The waveforms related to the important parts of the above operations will be described with reference to FIG. 27.

Figure 27:
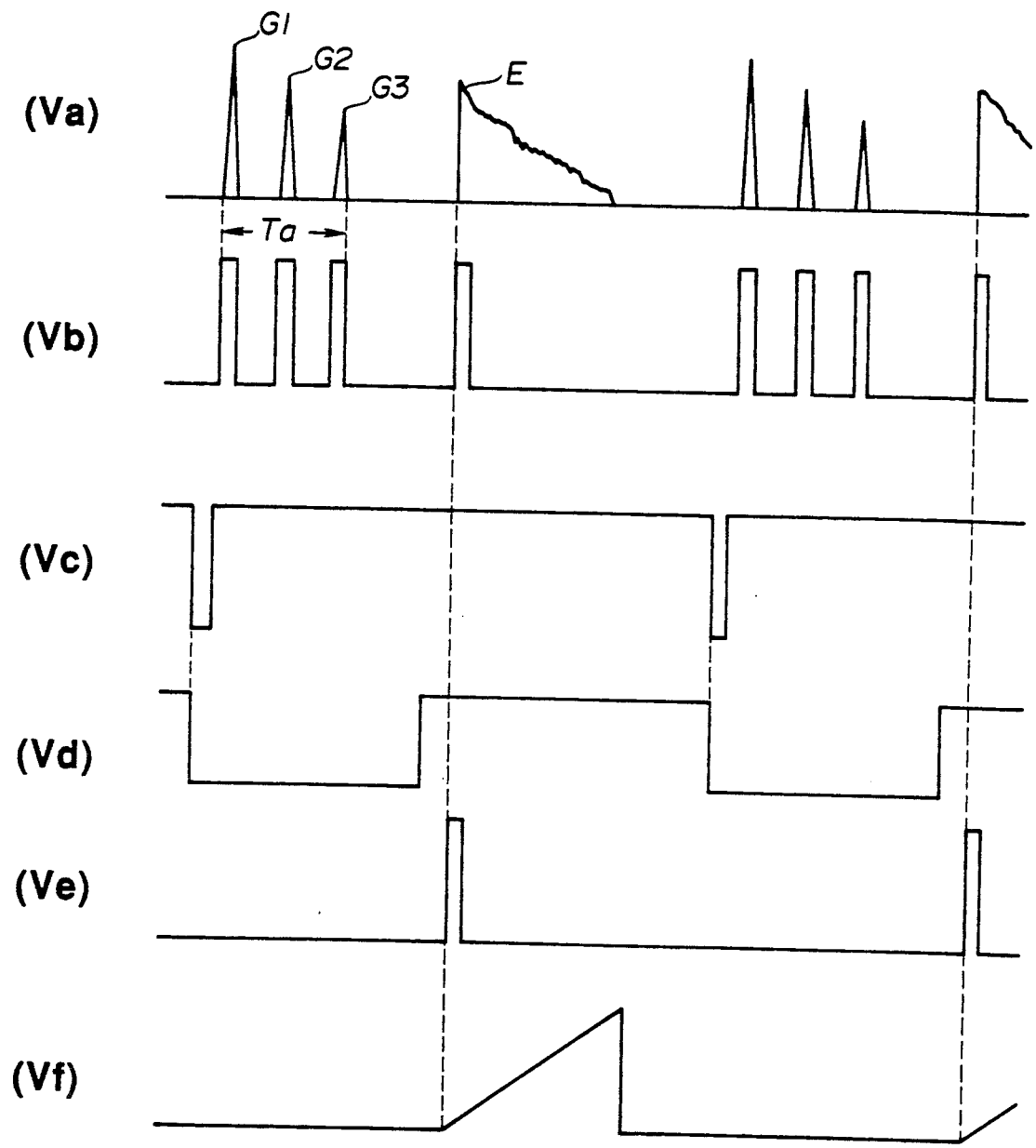

FIG. 27 (Va) shows the waveform of an output signal Va of the wave detector 214 which is an echo resulted from the reflection of an ultrasonic wave transmitted by the oscillator 202 at a location such as the location to be inspected.

This echo includes, for example, G1 through G3 which are the multiecho generated between the oscillator 202 and the head cap 205, and E which is the echo reflected by the location to be inspected.

The echo is converted, through the differentiator 226 and the waveform shaping circuit 227, into a logical signal Vb in which the logical value is "H" at the places corresponding to the peaks of the echo as shown in FIG. 27.

To the one-shot pulse generator circuit 220, as shown in FIG. 27 (Vc), a pulse wave Vc synchronized with the driving operation for the oscillator 202 is input from the rate pulse generating circuit 212.

Thus the one-shot pulse generator 220 generates a pulse wave having a width which is determined by the value of the capacitor 222 and the resistance of the group of resistors 221. This pulse wave undergoes inversion of the logical value by the inverter 224, and thereby becomes a logic signal Vd in which the logical signal is "L" for a predetermined period after the oscillator 202 is driven as shown in FIG. 27 (Vd).

The AND circuit 228 carries out the logical AND between the output signal Vb of the waveform shaping circuit 227 and the output signal Vc of the inverter 228. The AND circuit outputs a trigger signal Ve as shown in FIG. 27 (Ve) to the sawtooth wave generating circuit 229.

Upon the trigger signal Ve, the sawtooth wave generating circuit 229 outputs a control signal Vf as shown in FIG. 27 (Vf) for controlling the amplification degree of the STC 216.

The group of resistors 221 and the multiplexer 223 may be substituted by a variable resistor to set a desired time.

Thus, the one-shot pulse generator 220 provides an effect that the STC 216 starts variable amplification upon receipt of the echo from the location to be inspected.

Figure 28:
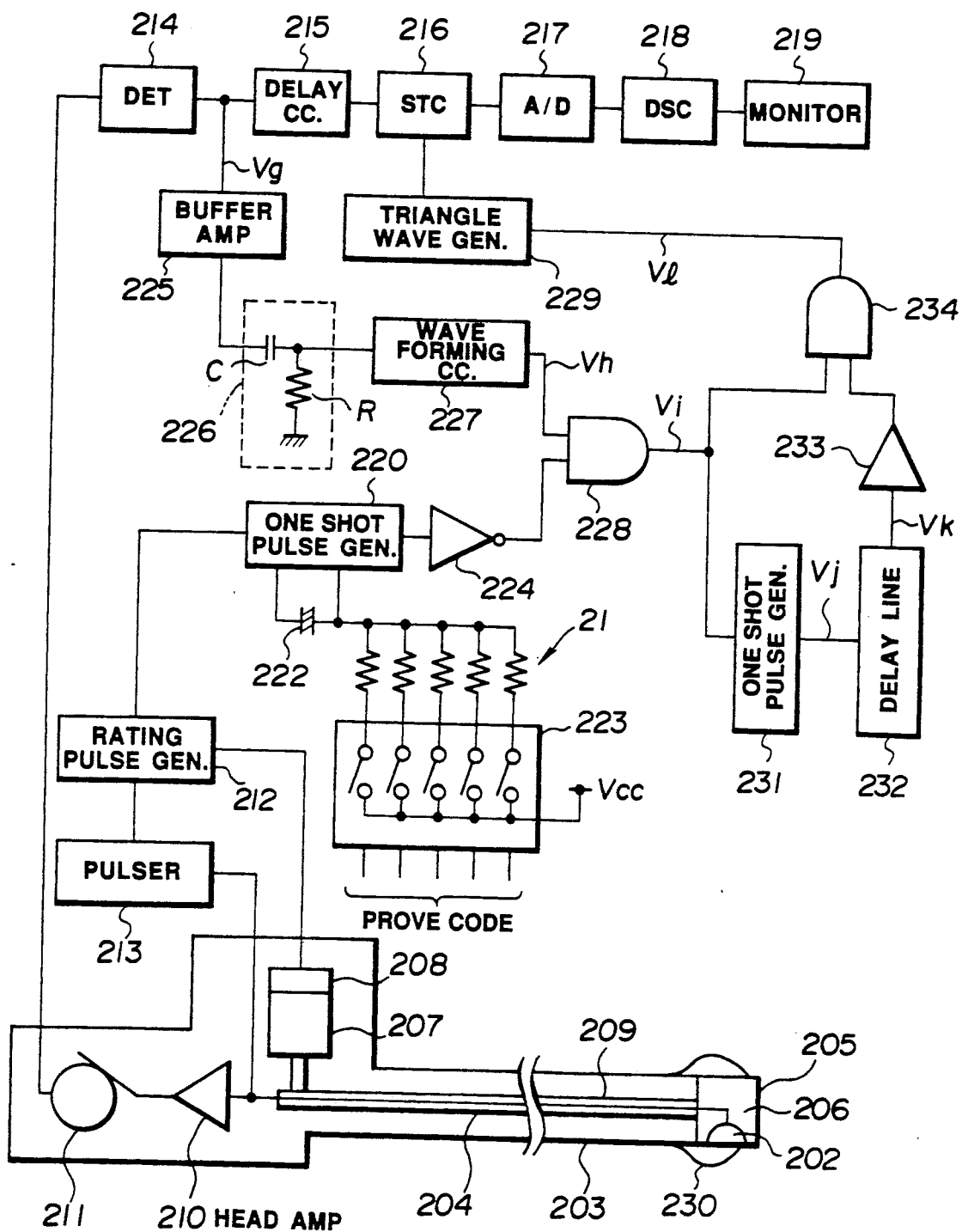
FIG. 28 and FIG. 29 relate to a third embodiment of the present invention.

FIG. 28 shows a third embodiment of the present invention.

Where the same part as that in the second embodiment is used, the same numeral as that in the second embodiment will be used and the description for such a part is omitted.

The ultrasonic diagnosis device in this embodiment comprises a balloon 230 which is filled, for example, by water provided around the outer circumference of the head cap 205 of the probe 201.

A one-shot pulse generator 231 generates a pulse wave having a predetermined pulse width provided between the AND circuit 228 and sawtooth wave generating circuit 229 as described in the second embodiment. A delay line 232 delays an input signal. A buffer 233 buffers between earlier and later stages. An AND circuit 234 carries out the logical AND between the output signal of the AND circuit 228 and the output signal of the buffer 233.

The output terminal of the AND circuit 228 is connected to the first input terminal of the AND circuit 234 and the trigger terminal of the one-shot pulse generator 231.

The output terminal of the one-shot pulse generator 231 is connected to the input terminal of the delay line 232. The output terminal of the delay line 232 is connected to the input terminal of the buffer 233. The output terminal of the buffer 233 is connected to the second input terminal of the AND circuit 234.

The output terminal of the AND circuit 234 is connected to the trigger terminal of the sawtooth wave generating circuit 229.

The operation of an ultrasonic diagnosis device configured as above will be described.

In the same way as that in the first embodiment, the AND circuit 228 carries out the logical AND between the waveform shaping circuit 227 and the signal of the inverter 224 and outputs the AND to the first input terminal of the AND circuit 234 and the trigger circuit of the one-shot pulse generator 231.

As a result of the above, the one-shot pulse generator 231 generates a pulse wave having a pulse width Tp shorter than the intervals of a pulse wave for driving the oscillator 202 based on the fact that an echo reflected by the location to be inspected exists within an interval of a rate pulse, and outputs the pulse wave to the delay line 232.

The delay line 232 delays the pulse wave input as described above by a predetermined period and outputs the delayed pulse wave to the buffer 233.

The buffer 233 shapes the waveform of the pulse input as described above and outputs the shaped pulse wave to the second input terminal of the AND circuit 234.

The AND circuit 234 outputs a trigger signal to the sawtooth wave generating circuit 229. The trigger signal is the logical AND between the output signal of the AND circuit 228 input to the first input terminal thereof and the output signal of the buffer 233 input to the second input terminal thereof.

The sawtooth wave generating circuit 229 is triggered by the trigger signal input as described above to generate a sawtooth wave which is output to the STC 216 in the same way as that in the second embodiment.

Description is omitted for other operations which are the same as those in the second embodiment.

The waveforms related to the important parts of the above operations will be described with reference to FIG. 29.

Figure 29:
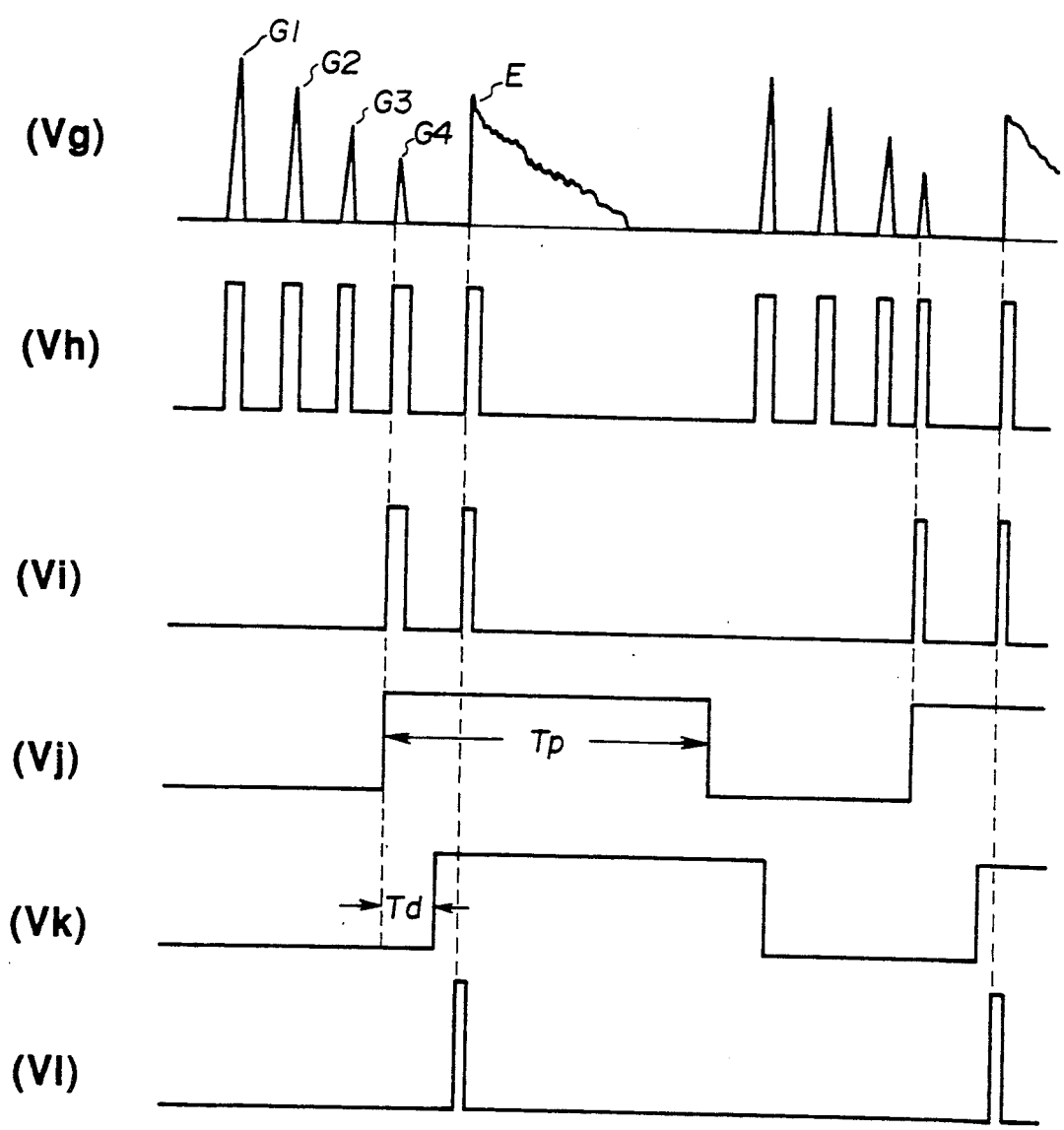

FIG. 29 (Vg) shows the waveform of an output signal Vg of the wave detector 214 which is an echo resulting from the reflection of an ultrasonic wave transmitted by the oscillator 202 at a location such as the location to be inspected.

This echo includes, for example, G1 through G3 which are the multiecho generated between the oscillator 202 and the head cap 205 and E which is the echo reflected by the location to be inspected.

The echo is converted, through the differentiator 226 and the waveform shaping circuit 227, into a logical signal Vh in which the logical value is "H" at the places corresponding to the peaks of the echo as shown in FIG. 29.

If the logical AND is carried out between the one-shot pulse generator 220 and the inverter 224 by the AND circuit 228 in the same way as that in the second embodiment, the output signal V1 of the AND circuit 228 will have a logical value "H" due to the reflection from the balloon 230 and the location to be inspected as shown in FIG. 29 (Vi).

The one-shot pulse generator 231 is triggered by the output signal of the AND circuit 228 to generate a pulse wave Vj of the logical value "H" having a pulse width Tp which is shorter than the intervals of a pulse wave for driving the oscillator 202, and outputs the pulse wave to the delay line 232.

The delay line 232 outputs a signal Vk which is the pulse wave input from the one-shot pulse generator 231 delayed by Td (time) to the buffer 233.

The delay time Td is determined by the value obtained by dividing the thickness of the balloon by the sound velocity. For example, the Td will be as follows.

$$0.1/(1.56 \times 10)^6 = 64 \text{ (nsec.)}$$

where the thickness of the balloon and the sound velocity are given as 0.1 (mm) and $1.56 \times 10^6$ (mm/sec.) respectively. The Td is set at the above value.

As described before, the delayed signal Vk is buffered by the buffer 233 and input to the second input terminal of the AND circuit 234.

The AND circuit 234 carries out the logical AND between the output signal Vi of the AND circuit 228 input to the first input terminal thereof and the output signal Vk of the delay line 232 input to the second input terminal thereof via the buffer 233, and outputs a trigger signal V1 as shown in FIG. 29 to the sawtooth wave generating circuit 229.

A voltage variable delay line in which the delay time varies depending on the voltage may be used as the delay line 232.

Also the group of resistors 221 and the multiplexer 223 may be substituted by a variable resistor to set a desired time.

Thus, in this embodiment, the echo due to the balloon 230 can be removed by the one-shot pulse generator 231, the delay line 232, the buffer 233 and the AND circuit 234.

Other effects of this embodiment are the same as those of the second embodiment.

Figure 30:
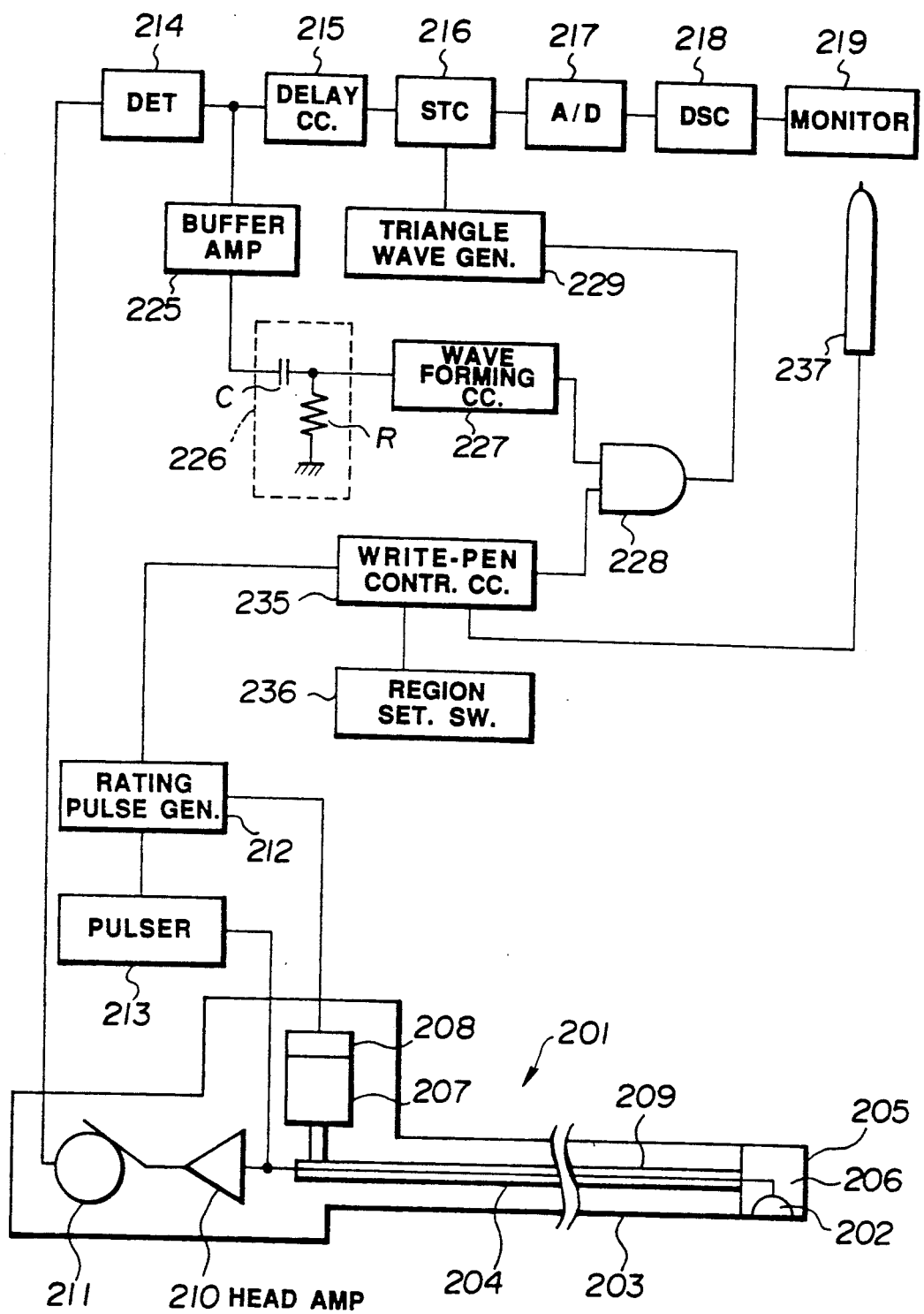
FIG. 30 and FIG. 31 relate to a fourth embodiment of the present invention.
Figure 31:
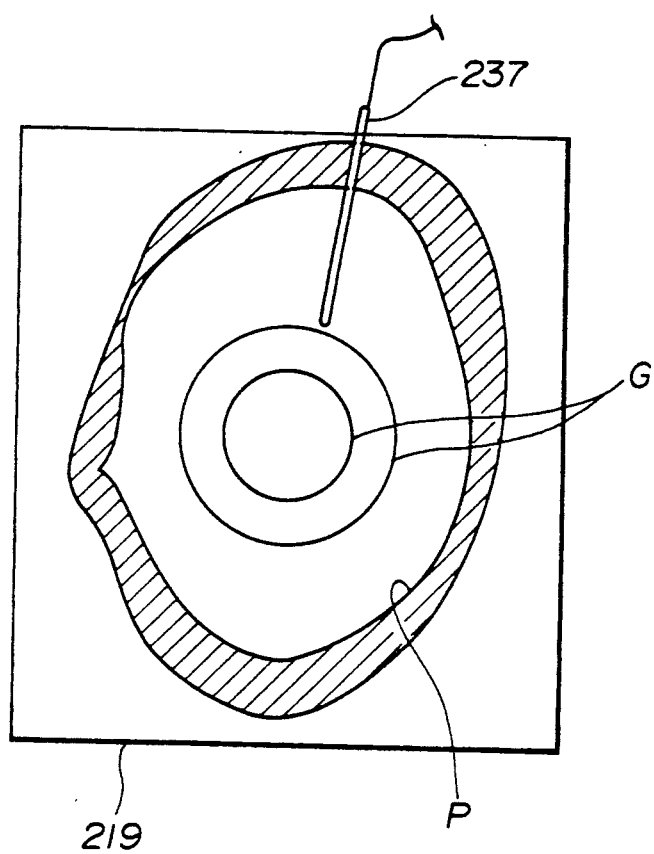

FIG. 30 shows a fourth embodiment of the present invention.

Instead of the one-shot pulse generating circuit 220, the group of resistors 221, the capacitor 222, the multiplexer 223 and the inverter 224 used in the ultrasonic diagnosis device according to the second embodiment, the ultrasonic diagnosis device according to this embodiment comprises a light pen controller 235 for controlling the sawtooth wave generating circuit 229 using the trigger signal of the rate pulse generator 212, a range setting switch 236 to be described later, a light pen 237 to be described later, a range setting switch 236 for setting the range of measurement, and a light pen 237 for specifying the position of a multiecho on the screen of the monitor 219.

The light pen controller 235 has a trigger terminal connected to the second output terminal of the rate pulse generator 212, a range input terminal connected to the output terminal of the range setting switch 236 and a light pen input terminal connected to the light pen 237.

The operation of an ultrasonic diagnosis device configured as above will be described.

The operator of the ultrasonic diagnosis device provides a mark for a multiecho on the screen of the monitor 14 with the light pen 237.

The mark is detected by the light pen controller 235.

Also the light pen controller 235 has the input of the value of a measurement range from the range setting switch 236 and a trigger signal from the rate pulse generator synchronized with the timing in which the oscillator 2 has transmitted a ultrasonic wave.

The light pen controller 235 calculates the time of the multiecho based on the position of the mark provided by the light pen 237, i.e. the pixel number, and the value of a measurement range input from the range setting switch 236, and it outputs a pulse wave of the logical value "L" having a pulse width which corresponds to the time obtained by the above operation, to the second input terminal of the AND circuit 228.

Thus there are effects that any multiecho can be removed using the light pen 237 and the range setting switch 236 and that the STC 216 starts variable amplification upon the echo of the location to be inspected.

A voltage variable band-pass filter, in which the passing band varies depending on voltage, may be used instead of the STC 216.

Also the STC 216 and the delay circuit 215 may be inter-changed.

Figure 32:
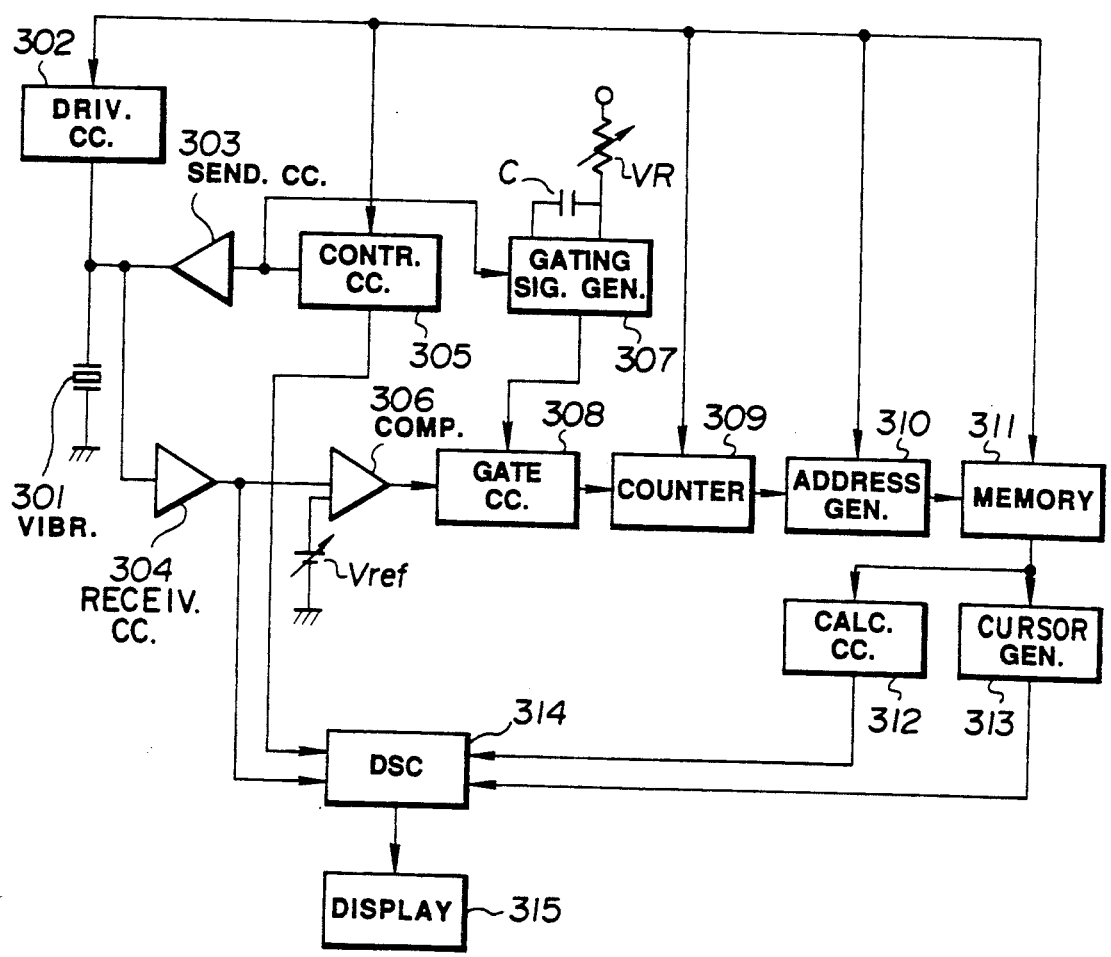
Figure 33A:
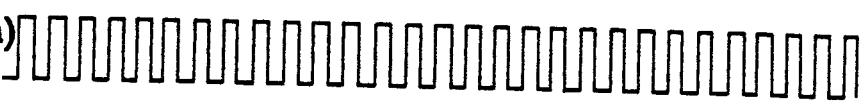
FIG. 33 is a timing chart for the device per FIG. 32.
Figure 33B:
Figure 33C:
Figure 33D:
Figure 33E:
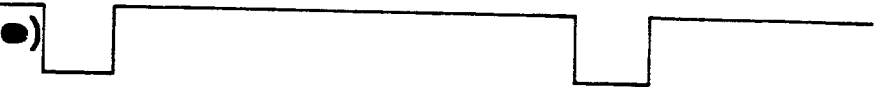
Figure 33F:
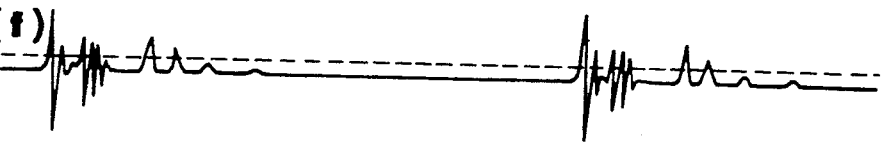
Figure 33G:
Figure 33H:
Figure 33I:
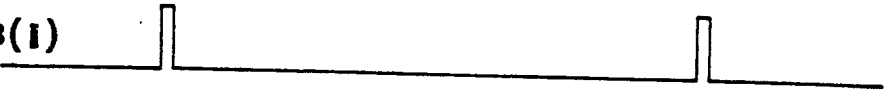

FIG. 32 shows a fifth embodiment of the present invention.

This embodiment is an ultrasonic diagnosis device which is suitable for measuring the diameter and the cross-sectional area of a blood vessel.

As shown in FIG. 32, the ultrasonic diagnosis device comprises an oscillator 301 for transmitting and receiving an ultrasonic wave. A driving circuit 302 drives the oscillator 301. A transmission circuit 303 oscillates the oscillator in an ultrasonic frequency. A reception circuit 304 receives a received wave from the oscillator 301. A comparator 306 detects a signal having a value more than a predetermined value from the signal of the reception circuit 304. A reference potential Vref is provided for the comparator 306. A gate circuit 308 controls whether or not to input the output signal of the comparator 306 to a counter 309 described later. A gate signal generator 307 controls the gate circuit 308. A capacitor C and a variable resistor VR set the controlling time of the gate signal generator 307. A counter counts a predetermined clock and outputs a counted value which is latched by the signal of the comparator 306 when the gate circuit 308 is open. An address generator 310 generates an address upon the output of the counter 309. A memory 311 stores the address generated by the address generator 310. An arithmetic circuit 312 carries out a predetermined calculation based on the data in the memory 311. A cursor generator 313 obtains the position of a cursor based on the data in the memory 311. A DSC 314 converts the signals from the reception circuit 304, the arithmetic circuit 312, cursor generator 313 and a control circuit 305 described later, into a signal such as a video signal. A display 315, e.g. a television monitor, displays the video signal of the DSC 314. A control circuit controls the driving circuit 302, transmission circuit 303, gate signal generator 307, counter 309, address generator 310, memory 311 and DSC 314.

The control circuit 305 is connected to the driving circuit 302, counter 309, address generator 310, memory 311, transmission circuit 303, gate signal generator 307 and DSC 314.

The oscillator 301 is connected to the output terminal of the transmission circuit 303 and the input terminal of the reception circuit 304.

The output terminal of the reception circuit 304 is connected to the first input terminal of the comparator 306 and the DSC 314.

The comparator 306 has a second terminal connected to the reference potential Vref and an output terminal connected to the counter 309 via the gate circuit 308.

The output terminal of the counter 309 is connected to the input terminal of the address generator 310 and the output terminal of the address generator 310 is connected to the memory 311.

The output terminal of the memory 311 is connected to the arithmetic circuit 312 and cursor generator 313.

The output terminals of the arithmetic circuit 312 and the cursor generator 313 are connected to the DSC 314.

The output terminal of the DSC 314 is connected to the input terminal of the display 315.

The output terminal of the gate signal generator 307 is connected to the control terminal of the gate circuit 308.

The operation of an ultrasonic diagnosis device configured as above will be described.

The driving circuit 302 drives the oscillator 301 in rotary motion by the voltage from the control circuit 305. The driving circuit 302 generates A-phase pulses in a predetermined number during one rotation of the oscillator 301, and at the same time it generates Z-phase pulses during each one rotation of the oscillator 301 and outputs them to the control circuit 305.

The control circuit 305 controls the A-phase pulses as shown in FIG. 33 (b) to the transmission circuit 303.

As shown in FIG. 33 (c), the transmission circuit 303 is triggered by the A-phase pulses to oscillate the oscillator 301 thereby transmitting an ultrasonic wave. Thus a rotary scan is performed with scanning lines in a number depending on the A-phase pulses.

As described before, the an ultrasonic wave transmitted by the oscillator 301 is reflected by a location to be inspected and the like, and is received by the oscillator 301 as shown in FIG. 33 (d).

The received signal (referred to as an echo hereinafter) undergoes processing such as amplification in the reception circuit 304, and then is output to the comparator 306 and DSC 314.

The comparator 306 compares the input signal with the reference potential Vref as indicated by the broken line in FIG. 33 (f), and when the input signal is in excess of the reference potential Vref, it outputs a logical signal of a high level as shown in FIG. 33 (g).

The gate signal generator 307 generates a predetermined gate signal as shown in FIG. 33 (c) from the time of the rising edge of the A-phase pulse as shown in FIG. 33 (b), and for a period depending on the time constant determined by the capacitor C and the variable resistor VR. The period of the gate signal is set at the period of a strong reflected wave as shown in FIG. 33 (d) which is caused by the multiecho of the transmitted ultrasonic wave as shown in the FIG. 33 (c) caused by the cap engagedly mounted on the oscillator 301, and the ringing of the oscillator 3.

Thus the gate circuit 308 closes the gate for the gate signal period as shown in FIG. 33 (e) and blocks the input signals shown in FIG. 33 (g) and outputs the signal as shown in FIG. 33 (h) to the counter 309.

The counter 309 has the input of the a clock pulse which is synchronized with the A-phase as shown in FIG. 33 (a).

The counter 309 is reset by the A-phase pulse input by the control circuit 305, counts the clock as shown in FIG. 33 (3), latches the clock with the first pulse as shown in FIG. 33 (i) of the output signal of the gate circuit 308 and outputs the count value to the address generator 310.

The address generator 310 generates an address value from the above count value and outputs the address value to the memory 311.

The address value input to the memory 311 is stored in the memory 311.

The address value stored in the memory 311 is read by the arithmetic circuit 312 and cursor generator 313.

The arithmetic circuit 312 operates the area and diameter of a region which is enclosed by the address value of the first pulse as described later, based on the read address value and known angle cf rotation and scan number, and outputs the area and diameter to the DSC 314.

At the same time, the cursor generator 313 generates a signal for displaying the cursor on the read address value and outputs it to the DSC 314.

The DSC 314 has the input of the forementioned clock pulse from the control circuit 305 which is synchronized with the A-phase as shown in FIG. 33 (a), the forementioned echo from the reception circuit 304 as shown in FIG. 33 (d), the forementioned signal for the operated value of the area and diameter from the arithmetic circuit 312, and the forementioned signal for displaying a cursor from the cursor generator 313.

Thus the DSC 314 stores an input signal, for example, in the memory of a predetermined address, and at the same time it outputs the value stored in the memory to the display 315 as a video signal and the like.

Figure 34:
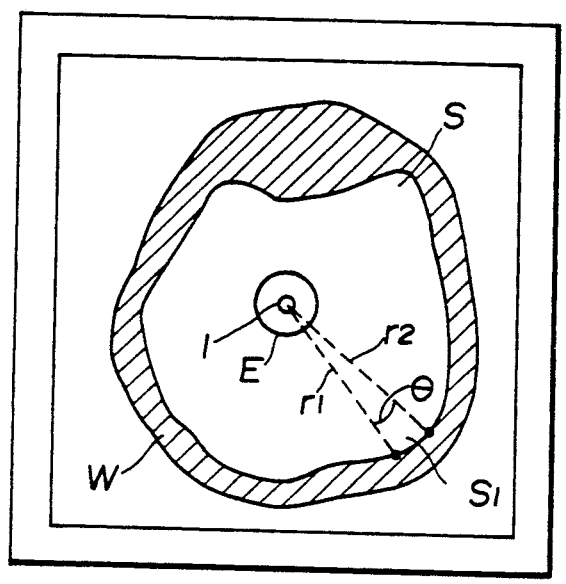
FIG. 34 and FIG. 35 illustrate a cross-sectional image of a blood vessel displayed on a monitor.
Figure 35:
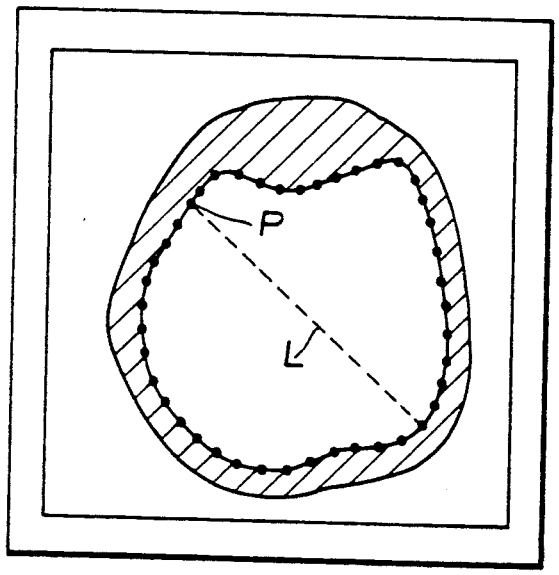

The display 315 displays the video signal of an image for observation input from the DSC 314, for example, as shown in FIG. 34 and FIG. 35.

As shown in FIG. 34, the display of the above-mentioned image for observation consists of a substantially annular display portion E near the oscillator 301 which is the result of the multiecho due to the cap engagedly mounted on the oscillator 301 and the ringing of the oscillator 301, and a blood vessel W which is the result of the echo from the reception circuit 304.

The area S of the region enclosed by the address value of the first pulse is obtained by the operating circuit 312, for example, as follows.

A length r1 is obtained from the time required for an ultrasonic wave while it is transmitted by the oscillator 301, reflected by the inner wall of a blood vessel and received by the oscillator 301. Then an area S1 enclosed by r1 and r2 which is the length obtained from next transmission of ultrasonic wave is obtained using $\theta$ which is the angle of the rotation until the next transmission of ultrasonic wave. This means that the operation is carried out assuming a substantially circular cross-sectional shape of a blood vessel. Therefore, the area is given by the equation below.

$$\Delta S1 = r1^2 \times \pi \times \theta / 360$$

This calculation is repeated for scanning lines in a number n and accumulated as follows.

$$S = \sum_{x=1}^{n} \Delta Sx$$

In this case the measurement point for the area to be calculated is indicated by the cursor P as shown in FIG. 35.

Also the diameter L of a region enclosed by the address value of the first pulse is obtained by the arithmetic circuit 312 as follows assuming, for example, 512 scanning lines, and based on the above-mentioned length of a scanning line 1 and another scanning line 257 at the symmetrical position.

$$L = r1 + r257$$

For an arbitrary scanning line, L can be obtained as follows.

$$L = rn + r512/2 + n + 1 \quad (1 \leq n \leq 128)$$

In this case the operated portion in the measurement of the diameter L is indicated in addition to the cursor P as shown in FIG. 35.

Also the average of Ls for all scanning lines may be indicated, or the maximum and minimum Ls may be indicated. Further, those indications may be combined.

Thus it is possible to operate the inner wall of a blood vessel, the diameter of a blood vessel from an echo at the point in time after a predetermined elapsed time after the transmission of an ultrasonic wave. Also errors in measurement can be reduced by the indication of the measurement point. Thus a quick and accurate measurement is possible.

Figure 36:
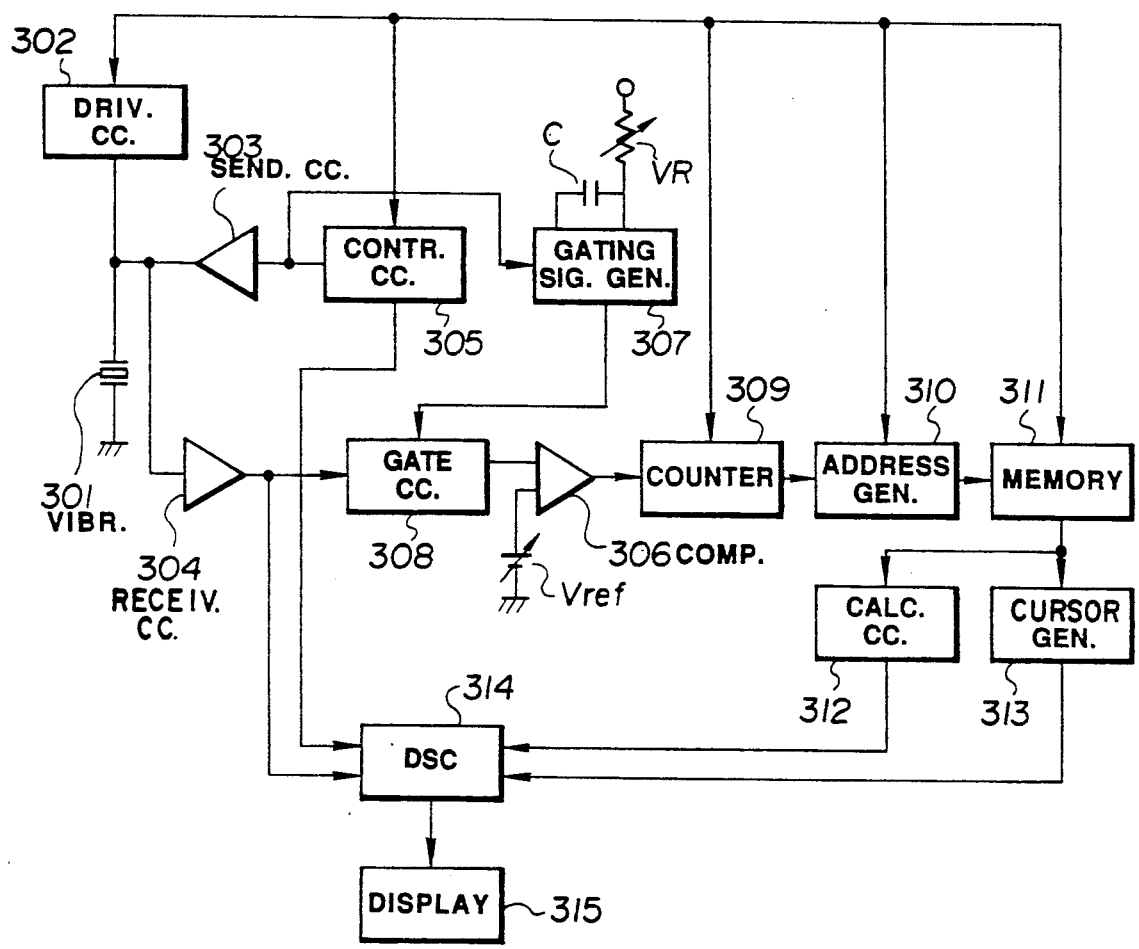
FIG. 36 illustrates the configuration of a sixth embodiment of the present invention.

FIG. 36 is a block diagram showing the configuration of an ultrasonic diagnosis device according to the sixth embodiment of the present invention.

Description is omitted for a part which is similar to that in the fifth embodiment by using the same reference numeral.

The gate circuit 308 in this embodiment has an input terminal connected to the output terminal of the reception circuit 304 and an output terminal connected to the first input terminal of the comparator 306. The output terminal of the comparator 306 is connected to the counter 309.

Therefore the echo of the reception circuit 304 shown in FIG. 33 (d) is not input to the comparator 306 due to the gate circuit 308 for the period shown in FIG. 33 (e) which is the period of the strong reflected wave shown in FIG. 33 (d), where a strong reflected wave is caused by the multiecho of a transmitted ultrasonic wave as shown in FIG. 33 (C) due to the cap engagedly mounted on the oscillator 301, and the ringing of the oscillator 301. The comparator 306 outputs the signal as shown in FIG. 33 (h) to the counter 309.

Figure 37:
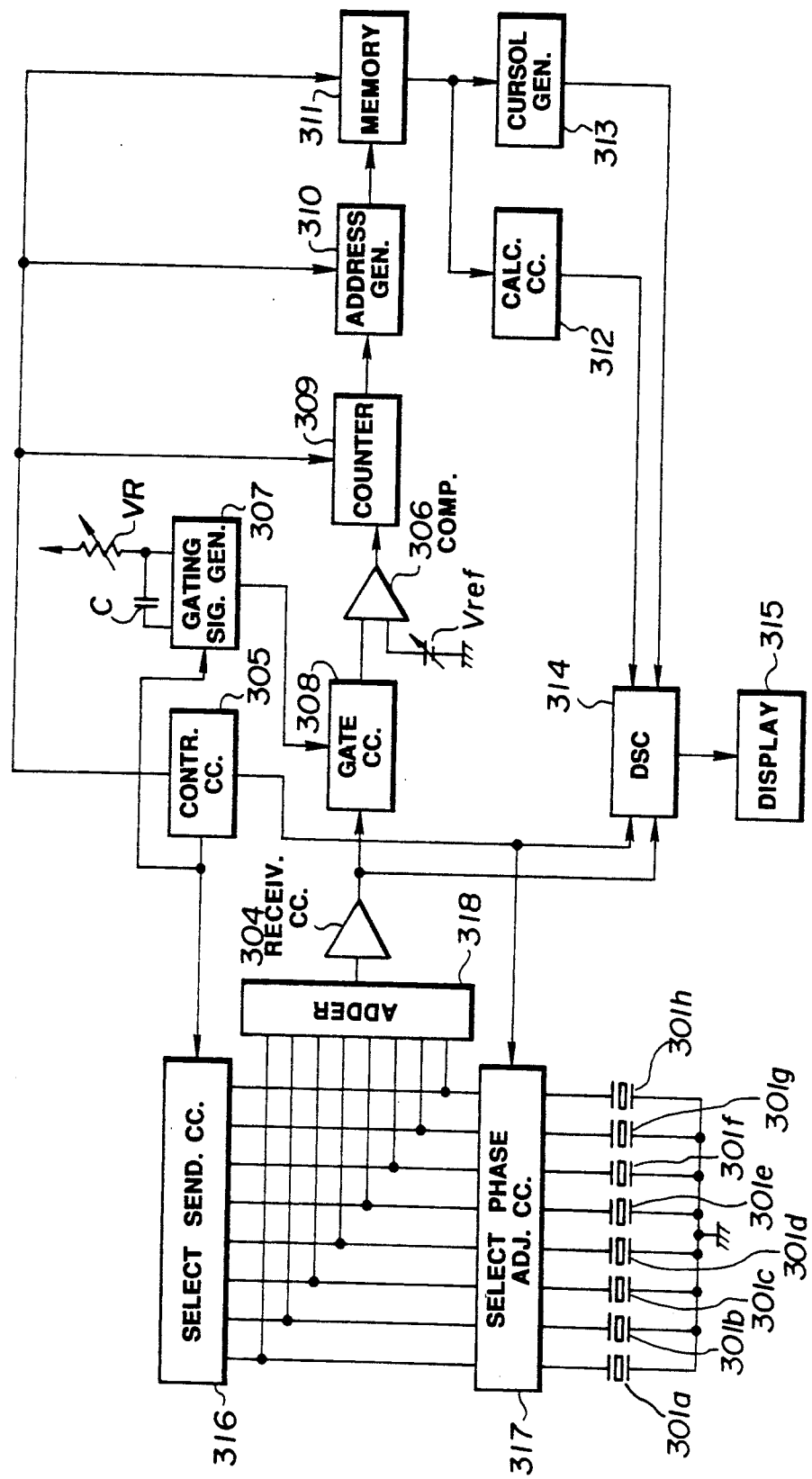
FIG. 37 illustrates the configuration of a seventh embodiment of the present invention.

FIG. 37 relates to a seventh embodiment of the present invention and is a block diagram illustrative of the configuration of an electronic scan type ultrasonic diagnosis device.

Description is omitted for a part which is similar to that in the fifth embodiment by using the same reference numeral.

As shown in FIG. 37, the ultrasonic diagnosis device comprises oscillators 301a through 301h, a selection/transmission circuit 316 for selecting the oscillators 301a through 301h and oscillating them in an ultrasonic frequency. A selection/phasing circuit 317 selects a received wave from the oscillators 301a through 301h and phases the selected received signal. Adder 318 adds the outputs of the selection/phasing circuit 317 and outputs it to a reception circuit 304. The reception circuit 304, a comparator 306, a reference potential Vref, a gate circuit 308, a gate signal generator 307, a capacitor C and a variable resistor VR, a counter 309, an address generator 310, a memory 311, an arithmetic circuit 312, a cursor generator 313, a DSC 314, a display 315 are also provided. A control circuit 305 controls the selection/transmission circuit 316, selection/phasing circuit 317, counter 309, address generator 310, memory 311 and DSC 314.

The oscillators 301a through 301h in this embodiment are provided on the circumference of the head portion of the probe having a substantially circular cross-section and are arranged in parallel to the longitudinal direction to the probe.

The oscillators 301a through 301h are selected by the selection/transmission circuit 316 which drives selection and transmission upon receiving a control signal of the control circuit 305, and transmits an ultrasonic wave. The ultrasonic wave is reflected by the body cavity and the like, received by the oscillators 301a through 301h, selected and phased by the selection/phasing circuit 317 which selects and phases upon receiving a control signal of the control circuit 305, and is input to the adder 318.

The adder 318 adds the signals input from the selection/phasing circuit 317 as described above and outputs it to the reception circuit 304.

Description for the remaining configurations and operations are omitted because they are similar to those in the fifth embodiment.

This embodiment is effective in that it can follow a quick movement of the location to be inspected by using an electronic scan type ultrasonic oscillator and in that it can provide an accurate diagnosis because the oscillator is not rotated.

Other effects of this embodiment are the same as those of the fifth and sixth embodiments.

Figure 38:
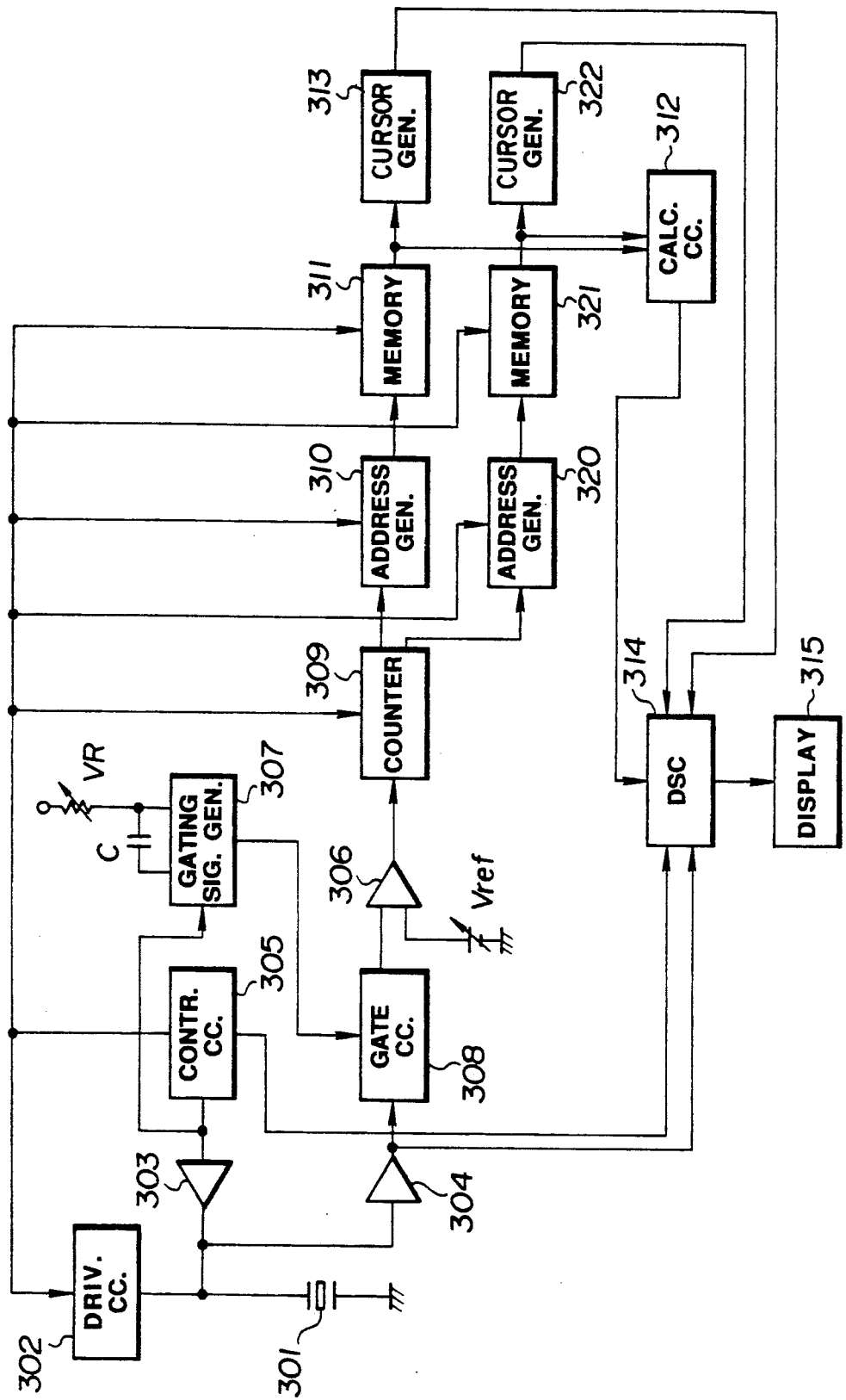
FIG. 38 through FIG. 41 relate to an eighth embodiment of the present invention.
Figure 39A:
Figure 39B:
Figure 39C:
Figure 39D:
Figure 39E:
Figure 39F:
Figure 39G:
Figure 39H:
Figure 39I:

FIG. 38 shows an eighth embodiment of the present invention.

This embodiment is different from the sixth embodiment in that there are additional parts which are an address generator 320, a memory 321 and a cursor generator 322.

The counter 309 is reset by a signal synchronized with an ultrasonic pulse form the transmission circuit 303 and it counts a predetermined clock, latches a count output by the output of the comparator 306 and outputs it to the address generators 310 and 320. The address generator 310 generates an address value based on the count output until the first echo signal from the inner wall of a blood vessel after the gate circuit 308 is open. The address generator 320 generates an address value based on the count output until the second echo signal from the inner wall of a blood vessel after the gate circuit 308 is opened. This means that the address value from the address generator 310 corresponds to the distance between the oscillator 301 and the inner wall of a blood vessel while the address value from the address generator 320 corresponds to the distance between the oscillator 301 and the outer circumference of a blood vessel. The memory 321 stores the output of the address generator 320. The stored address value is read by the control circuit 305 and supplied to the arithmetic circuit 312 and the cursor generator 322. The cursor generator 322 outputs data to DSC 314 which is for displaying the cursor at the coordinate based on the address value stored in the memory 321. The arithmetic circuit 312 is supplied with the information of the address values stored in the memories 311 and 321, the angle of rotation and the scanning position of the oscillator 301. The arithmetic circuit 312 obtains the thickness of a blood vessel wall and the cross-sectional area of a blood vessel and outputs this data to the DSC 314.

Figure 40:
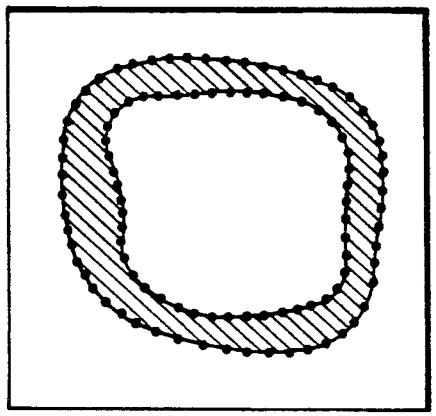

In an embodiment having the above configuration, an echo signal from the reception circuit 304 is supplied to the DSC 314. The DSC 314 generates a video signal for displaying the cross-sectional image of a blood vessel and supplies it to the display 315. Thus the cross-sectional image as shown in FIG. 40 is displayed on the screen of the display 315. While it is similar to the sixth embodiment in that the pulse as shown in FIG. 39 is output from the comparator 306. The address generator 310 generates an address value depending on the count output up to the first pulse among the outputs of the generator 306, i.e. the pulse (FIG. 39 (h)) which is based on the echo signal from the inner wall of a blood vessel, and causes the memory 311 to store such an address value. The address generator 320 generates an address value depending on the count output up to the second pulse among the outputs of the generator 306, i.e. the pulse (FIG. 39 (i)) which is based on the echo signal from the outer circumference of a blood vessel, and causes the memory 311 to store such an address value.

The arithmetic circuit 312 calculates a cross-sectional area including the area enclosed by a blood vessel wall and the cavity of a blood vessel based on the address values stored in the memories 311 and 321. It further operates the cross-sectional area of a blood vessel (the portion indicated by oblique lines in FIG. 40) by subtracting the above values and outputs this data to the DSC 314. Thus the display 315 displays the cross-sectional area of a blood vessel and the like.

Figure 41:
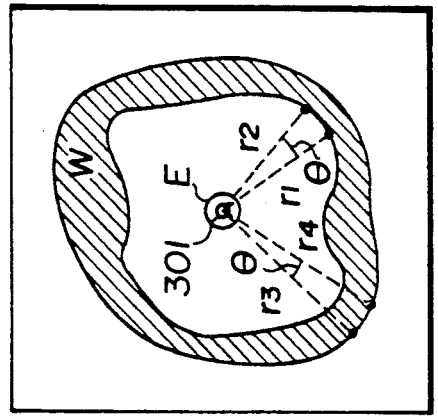

The cursor generators 313 and 322 outputs to the DSC 314, the data for displaying cursor based on the address values stored in the memories 311 and 321. The DSC 314 causes the display 315 to display the measurement point as shown in FIG. 41.

This embodiment is advantageous in that it enables a calculation of the elasticity of a blood vessel because it provides the measurement of the diameter and cross-sectional area of a blood vessel and the thickness of a blood vessel wall.

Other operations and effects of this embodiment are the same as those in the sixth embodiment.

FIG. 42 shows a driving system for an oscillator in a ninth embodiment of the present invention.

An oscillator 301 is provided at the head portion of an ultrasonic probe 350. The back end of the ultrasonic probe 350 is connected to the driving shaft of a motor 353 which is not shown via a slip ring 351 and an encoder 352 of a driving device. The rotation of the driving shaft of the motor 353 causes the probe 350 to rotate enabling the oscillator 301 to perform a rotary scan. The slip ring 351 is connected to a signal line which is not shown, for transmitting the driving signal and received signal of the oscillator 301 to supply the driving signal from a transmission circuit to the signal line and to pick up and transmit the received signal to the transmission circuit. The encoder 352 detects the rotation of the motor 352 and outputs A-phase and Z-phase pulses.

The slip ring 351 encoder 352 and motor 353 are combined together and are connected to a ball screw 355 via a transmission shaft 354. One of the ends of the ball screw 355 is connected to the motor 357 via the encoder 356. The rotation of the motor 357 causes the ball screw 355 to rotate thereby the transmission shaft 354 moves in the axial direction to the ball screw 355. Thus the rotation of the motor 357 causes the combined slip ring 351, encoder 352 and motor 353 to reciprocate in the axial direction to the ball screw 355, and at the same time the ultrasonic probe 350 reciprocates. This operation enables the oscillator 301 to perform a linear scan. The encoder 356 detects the rotation of the motor 357 thereby enabling the position control for the linear scan.

In an embodiment configured as described above, as shown in FIG. 43, the ultrasonic probe 350 inserted into a blood vessel 361 is rotated and reciprocated by the motors 353 and 357 to cause the oscillator 301 to perform a rotary and a linear scan. At the positions indicated by lines 44A—44A, 44B—44B and 44C—44C in FIG. 43, the oscillator 301 performs a rotary scan to obtain cross-sectional images as shown in FIGS. 44 (a), 44 (b) and 44 (c). Also a three-dimensional image as shown in FIG. 45 can be displayed by generating a video signal for a three dimensional image from an echo which is obtained by a spiral reciprocation of the oscillator 301.

With the ability to display a three-dimensional image of a blood vessel which enables the status of a blood vessel wall to be easily understood, this embodiment is quite advantageous in diagnosis for a location affected by a disease.

Figure 46:
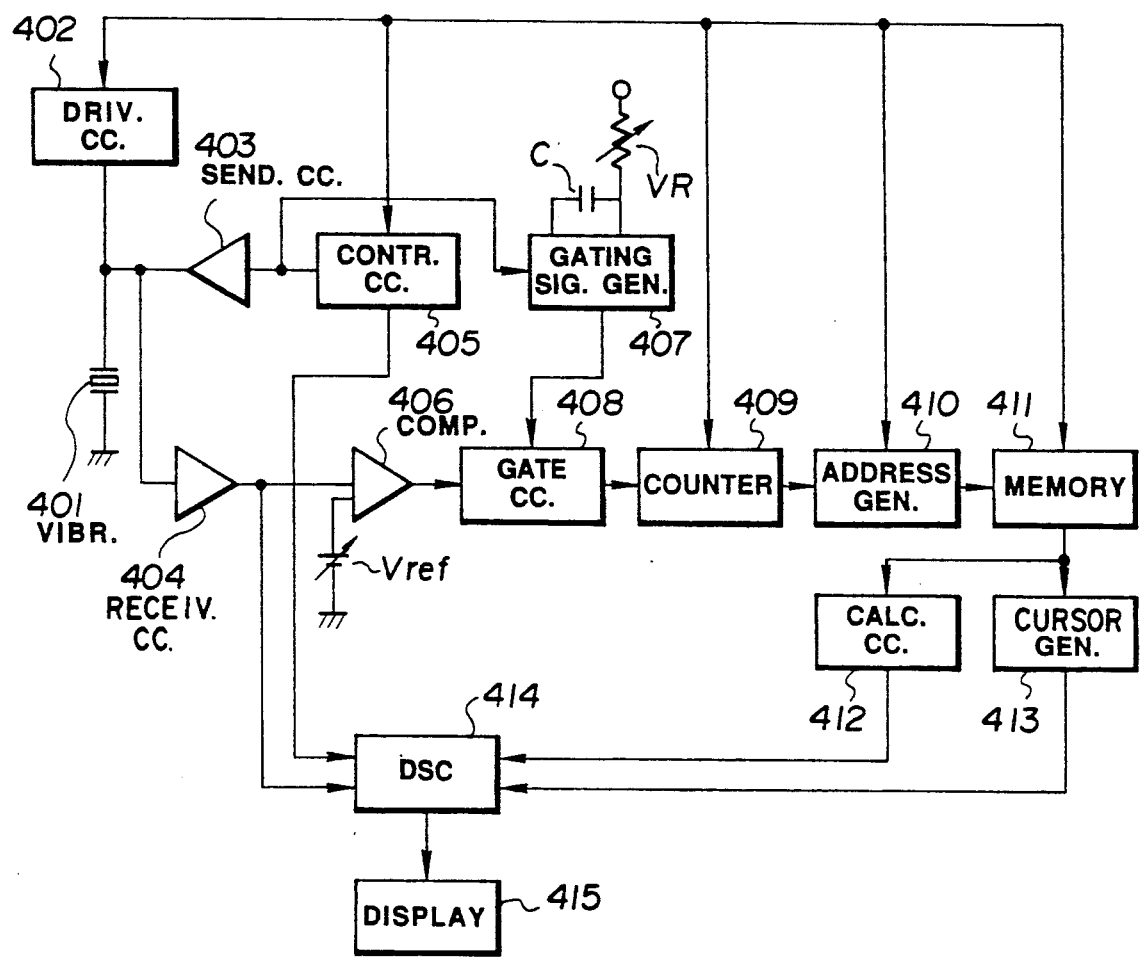
FIG. 46 through FIG. 49 relates to a tenth embodiment of the present invention.

FIG. 46 shows a tenth embodiment of the present invention.

This embodiment enables an accurate calculation of the cross-sectional area of a blood vessel.

As shown in FIG. 46, the ultrasonic diagnosis device comprises an oscillator 401 for transmitting and receiving an ultrasonic wave. A driving circuit 402 drives the oscillator 401 in a rotary motion. A transmission circuit 403 oscillates the oscillator 401 in an ultrasonic frequency. A reception circuit 404 receives a received signal from the oscillator 401. A comparator 406 detects a signal having a value in excess of a predetermined value from the reception circuit 404. A reference potential Vref is provided for the comparator 406. A gate circuit controls whether or not to input the output signal of the comparator 406 to a counter 409 which is described later. A gate signal generating circuit 407 controls the gate circuit 408. A capacitor C and a variable resistor VR set the control time of the gate signal generating circuit 407. A counter 409 counts the signal of the comparator 406 when the gate circuit 408 is open.

An address generator 410 generates an address upon receiving the signal of the counter 409. A memory 411 stores the address given by the address generator 410. An arithmetic circuit 412 performs a predetermined calculation based on the data in the memory 411. A cursor generator 413 obtains the position of a cursor from the data in the memory 411. A DSC 414 converts the signals from the reception circuit 404, arithmetic circuit 412, cursor generator 413 and a control circuit described later into a video signal and the like. A display which is, for example, a television monitor displays the video signal of the DSC 414. The control circuit 405 controls the driving circuit 402, transmission circuit 403, gate signal generator 407, counter 409, address generator 410, memory 411 and DSC 414.

The control circuit 405 is connected to the driving circuit 402, counter 409, address generator 410, memory 411, transmission circuit 403, gate signal generator 407 and DSC 414.

The oscillator 401 is connected to the output terminal of the transmission circuit 403 and the input terminal of the reception circuit 404.

The output terminal of the reception circuit 404 is connected to the first input terminal of the comparator 406 and the DSC 414.

The comparator 406 has a second input terminal connected to the reference potential Vref and an output terminal connected to the counter 409.

The output terminal of the counter 409 is connected to the input terminal of the address generator 410 and the output terminal of the address generator 410 is connected to the memory 411.

The output terminal of the memory 411 is connected to the arithmetic circuit 412 and the cursor generator 413.

The output terminals of the arithmetic circuit 412 and the cursor generator 413 are connected to the DSC 414.

The output terminal of the DSC 414 is connected to the input terminal of the display 415.

The output terminal of the gate signal generator 407 is connected to the control terminal of the gate circuit 408.

The operation of an ultrasonic diagnosis device configured as above will be described.

The driving circuit 402 drives the oscillator 401 in a rotary motion by the voltage from the control circuit 405, and at the same time, it generates an A-phase and a Z-phase which is output for each one rotation of the oscillator 401, and outputs them to the control circuit 405.

Figure 47:
Figure 47:
Figure 47:
Figure 47:
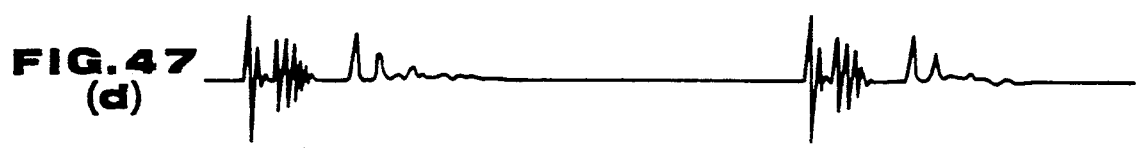
Figure 47:
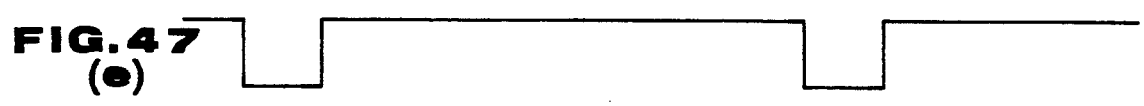
Figure 47:
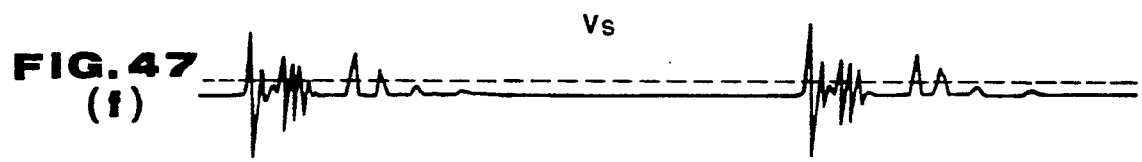
Figure 47:
Figure 47:
Figure 47:

The control circuit 405 outputs an A-phase pulse as shown in FIG. 47 (c) to the transmission circuit 403.

The transmission circuit 403 is triggered by the A-phase pulse to drive the oscillator 401 to oscillate enabling the transmission of an ultrasonic wave.

The ultrasonic wave transmitted by the oscillator 401 is reflected by the location to be inspected and the like and received by the oscillator 401 as shown in FIG. 47 (d).

The received signal (referred to as an echo hereinafter) undergoes processing such as amplification by the reception circuit 404 and is output to the comparator 406 and the DSC 414.

The comparator 406 compares the received signal with a threshold level (Vs) of the reference potential Vref, and when the input signal is in excess of the threshold level (Vs) it changes the logical signal of the output terminal thereof as shown in FIG. 47 (g).

The gate signal generating circuit 407 generates a predetermined gate signal as shown in FIG. 47 (b) upon receiving the A-phase pulse as shown in 47 (c) with the capacitor C and the variable resistor VR. The period of the gate signal is the period of a strong reflected wave as shown in FIG. 47 (d) which is the result of the multiple echo of the transmitted ultrasonic wave as shown in FIG. 47 (c) by the cap engagedly mounted on the oscillator 401 and the ringing of the oscillator 401.

Thus the gate circuit 408 closes the gate for the period of the gate signal as shown in FIG. 47 (e), blocks an input signal as shown in FIG. 47 (g) and transmits an output signal as shown in FIG. 47 (h) to the counter 409.

The counter 409 has the input of a clock pulse which is synchronized with the A-phase as shown in FIG. 47.

The counter 409 is reset by the A-phase pulse input by the control circuit 405, counts the clock as shown in FIG. 47 (a), latches the clock with the first pulse as shown in FIG. 47 (i) of the output signal of the gate circuit 408 as shown in FIG. 47 (h) and outputs the count value to the address generator 410.

The address generator 410 generates an address value from the above count value and outputs the address value to the memory 411.

The address value input to the memory 411 is stored by the memory 411.

The address value stored in the memory 411 is read by the arithmetic circuit 412 and the cursor generator 413.

The arithmetic circuit 412 calculates the area and diameter of a region which is enclosed by the address value of the first pulse as described later, based on the read address value and known angle of rotation and scan number, and outputs the area and diameter to the DSC 414.

At the same time, the cursor generator 413 generates a signal for displaying a cursor on the read address value and outputs it to the DSC 414.

The DSC 414 has the input of the forementioned clock pulse from the control circuit 405 which is synchronized with A-phase as shown in FIG. 47 (a), the forementioned echo from the reception circuit 404 as shown in FIG. 47 (d), the forementioned signal for the calculated value of the area and diameter from the arithmetic circuit 412, and the forementioned signal for displaying a cursor from the cursor generator 413.

Thus the DSC 414 stores an input signal, for example, in the memory of a predetermined address, and at the same time it outputs the value stored in the memory to the display 415 as a video signal and the like.

Figure 48:
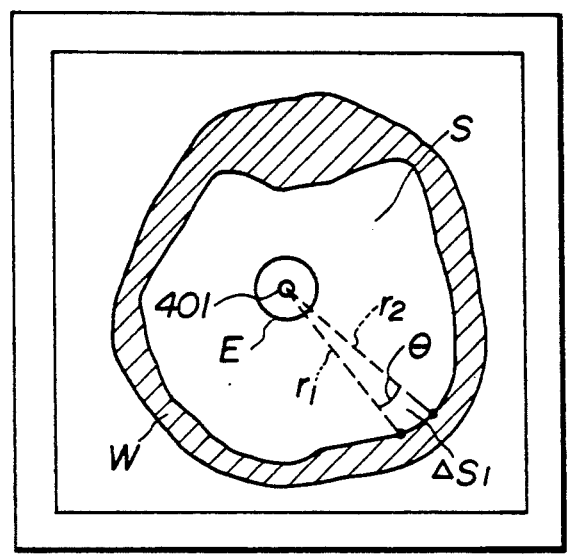
Figure 49:
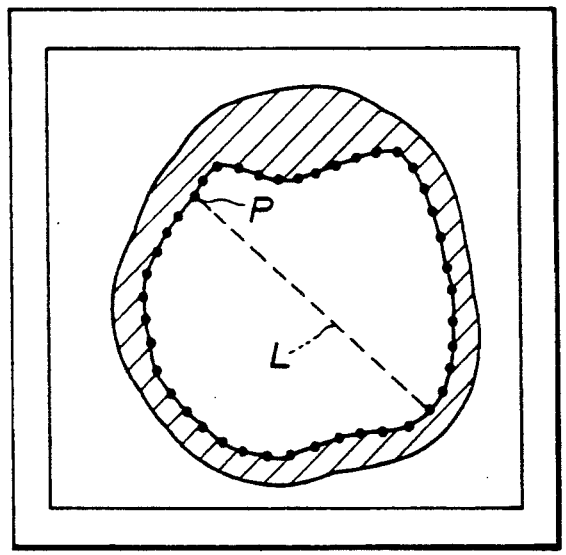

The display 415 displays the video signal of an image for observation input from the DSC 414, for example, as shown in FIG. 48 and FIG. 49.

As shown in FIG. 48, the display of the above-mentioned image for observation consists of a substantially annular display portion E near the oscillator 401 which is the result of the multiecho due to the cap engagedly mounted on the oscillator 401 and the ringing of the oscillator 401, and a blood vessel W which is the result of the echo from the reception circuit 404.

The area S of the region enclosed by the address value of the first pulse is obtained by the arithmetic circuit 412, for example, as follows.

A length r1 is obtained from the time required for an ultrasonic wave while it is transmitted by the oscillator 401, reflected by the inner wall of a blood vessel and received by the oscillator 401. An area S1 enclosed by r1 and r2 which is the length obtained from next transmission of ultrasonic wave is obtained using the angle of the rotation until the next transmission of the ultrasonic wave. This means that the calculation is carried out assuming a substantially circular cross-sectional shape of a blood vessel. Therefore, the area is given by the equation below.

$$\Delta S1 = r1^2 \times \pi \times \theta / 360$$

This calculation is repeated for scanning lines in a number n and accumulated as follows.

$$S = \sum_{x=1}^{n} \Delta Sx$$

In this case the measurement point for the area to be calculated is indicated by the cursor P as shown in FIG. 49.

The diameter L of a region enclosed by the address value of the first pulse is obtained by the arithmetic circuit 412 as follows assuming, for example, 512 scanning lines, and based on the above-mentioned length of a scanning line 1 and another scanning line 257 at the symmetrical position.

$$L = r1 + r257$$

For an arbitrary scanning line, L can be obtained as follows.

$$L = rn + r512/2 + n + 1 \ (1 \leq n \leq 128)$$

In this case the calculated portion in the measurement of the diameter L is indicated in addition to the cursor P as shown in FIG. 49.

- The average of Ls for all scanning lines may be indicated, or the maximum and minimum Ls may be indicated. Further, those indications may be combined.

Thus it is possible to calculate the inner wall of a blood vessel, the diameter of a blood vessel from an echo at the point in time after a predetermined elapsed time after the transmission of an ultrasonic wave. Also errors in measurement can be reduced by the indication of the measurement point. Thus, a quick and accurate measurement is possible.

Figure 50:
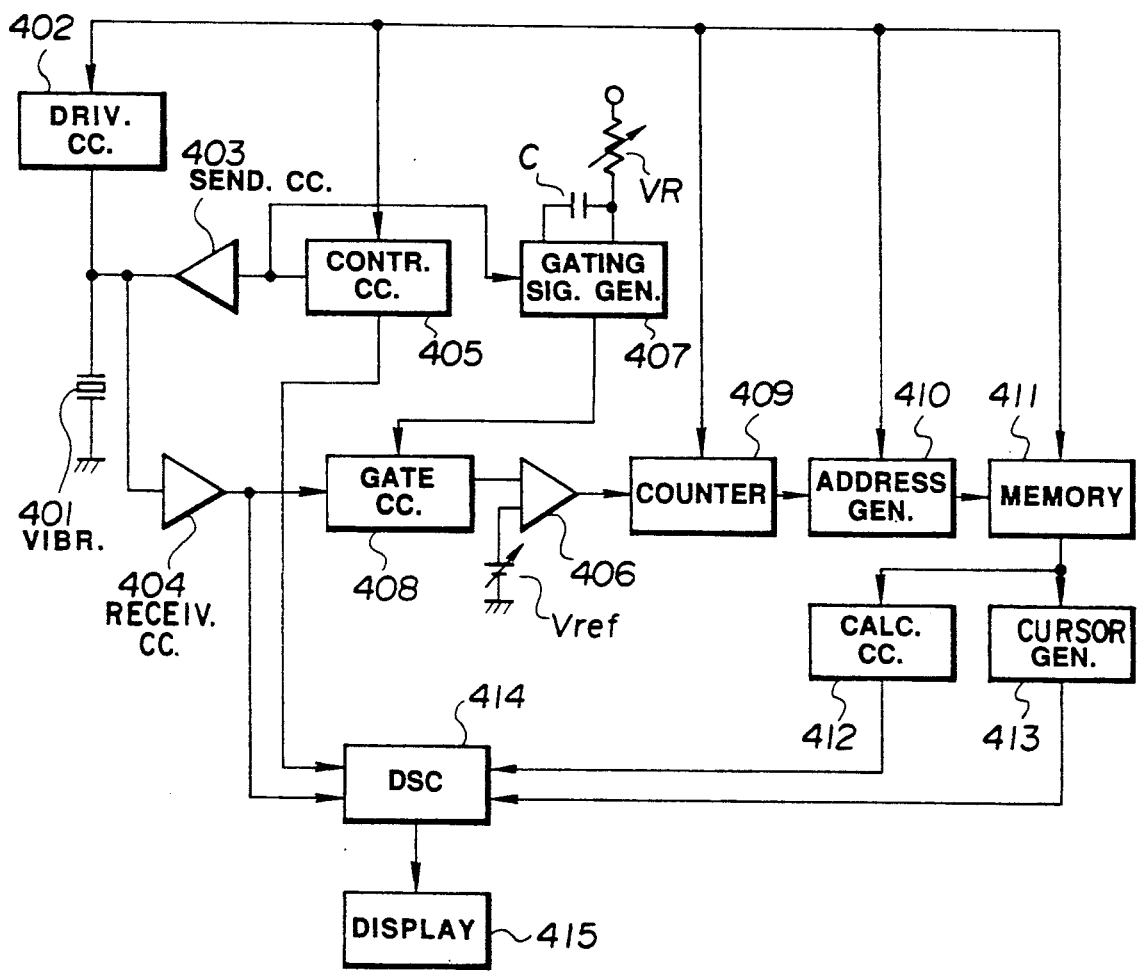
FIG. 50 illustrates the configuration of an eleventh embodiment of the present invention.

FIG. 50 shows eleventh embodiment of the present invention.

The gate circuit 408 in this embodiment has an input terminal connected to the output terminal of the reception circuit 404 and an output terminal connected to the first input terminal of the comparator 406. The output terminal of the comparator 406 is connected to the counter 409.

Therefore the echo of the reception circuit 404 shown in FIG. 47 (d) is not input to the comparator 406 due to the gate circuit 408 for the period shown in FIG. 47 (e) which is the period of the strong reflected wave shown in FIG. 47 (d), where strong reflected wave is caused by the multiecho of a transmitted ultrasonic wave as shown in FIG. 47 (C) due to the cap engagedly mounted on the oscillator 401, and the ringing of the oscillator 401. The comparator 406 outputs the signal as shown in FIG. 47 (h) to the counter 409.

Other configurations, operations and effects are the same as those of the tenth embodiment.

Figure 51:
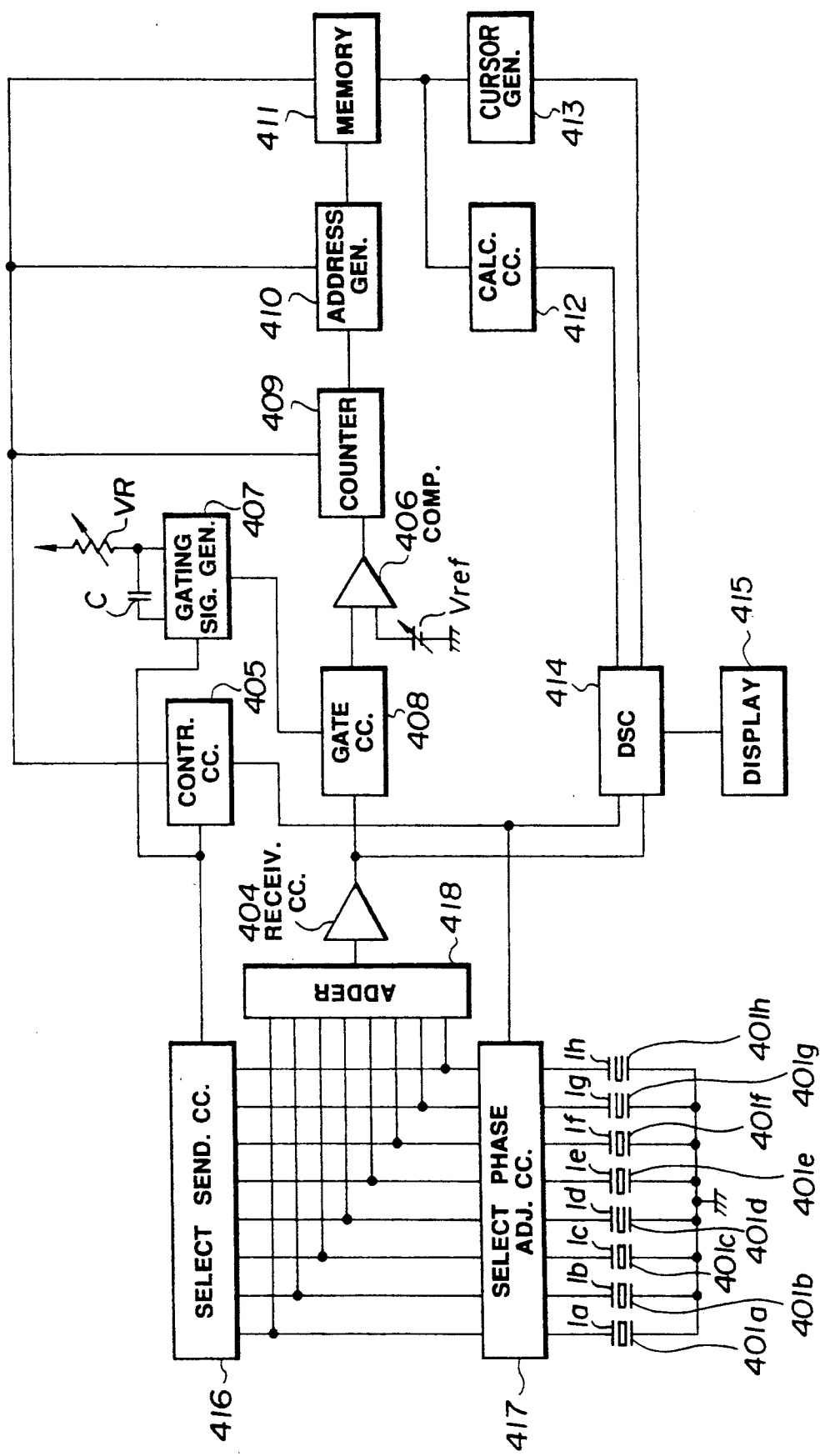
FIG. 51 illustrates the configuration of a twelfth embodiment of the present invention.

FIG. 51 shows the electronic scan type ultrasonic diagnosis device according to the twelfth embodiment of the present invention.

As shown in FIG. 51, the ultrasonic diagnosis device comprises oscillators 401a through 401h. A selection/transmission circuit 416 selects the oscillators 401a through 401h and oscillating them in an ultrasonic frequency. A selection/phasing circuit 417 selects a received wave from the oscillators 401a through 401h and phases the selected received signal. An adder 418 adds the outputs of the selection/phasing circuit 417 and outputs it to a reception circuit 404. The reception circuit 404, a comparator 406, a reference potential Vref, a gate circuit 408, a gate signal generator 407, a capacitor C and a variable resistor VR, a counter 409, an address generator 410, a memory 411, an arithmetic circuit 412, a cursor generator 413, a DSC 414, a display 415 are provided. A control circuit 405 controls the selection/transmission circuit 416, selection/phasing circuit 417, counter 409, address generator 410, memory 411 and DSC 414.

The oscillators 401a through 401h in this embodiment are provided on the circumference of the head portion of the probe having a substantially circular cross-section and are arranged in parallel to the longitudinal direction to the probe.

The oscillators 401a through 401h are selected by the selection/transmission circuit 416 which drives selection and transmission upon a control signal of the control circuit 405, and transmits an ultrasonic wave. The ultrasonic wave is reflected by the body cavity and the like, received by the oscillators 401a through 401h, selected and phased by the selection/phasing circuit 417 which selects and phases upon receiving a control signal of the control circuit 405, and is input to the adder 418.

The adder 418 adds the signals input from the selection/phasing circuit 417 as described above and outputs it to the reception circuit 404.

Description for the remaining configurations and operations are omitted because they are similar to those in the tenth embodiment.

- This embodiment is effective in that it can follow a quick movement of the location to be inspected by using an electronic scan type ultrasonic oscillator and in that it can provide an accurate diagnosis because the oscillator is not rotated.

Other effects of this embodiment are the same as those of the tenth and eleventh embodiments.

The device may be controlled to enable display of the length of the cross-section (thickness) of the location to be inspected, by storing an address in excess of a second predetermined value from an echo in excess of a first predetermined value be calculated and displayed using a cursor.

Figure 52:
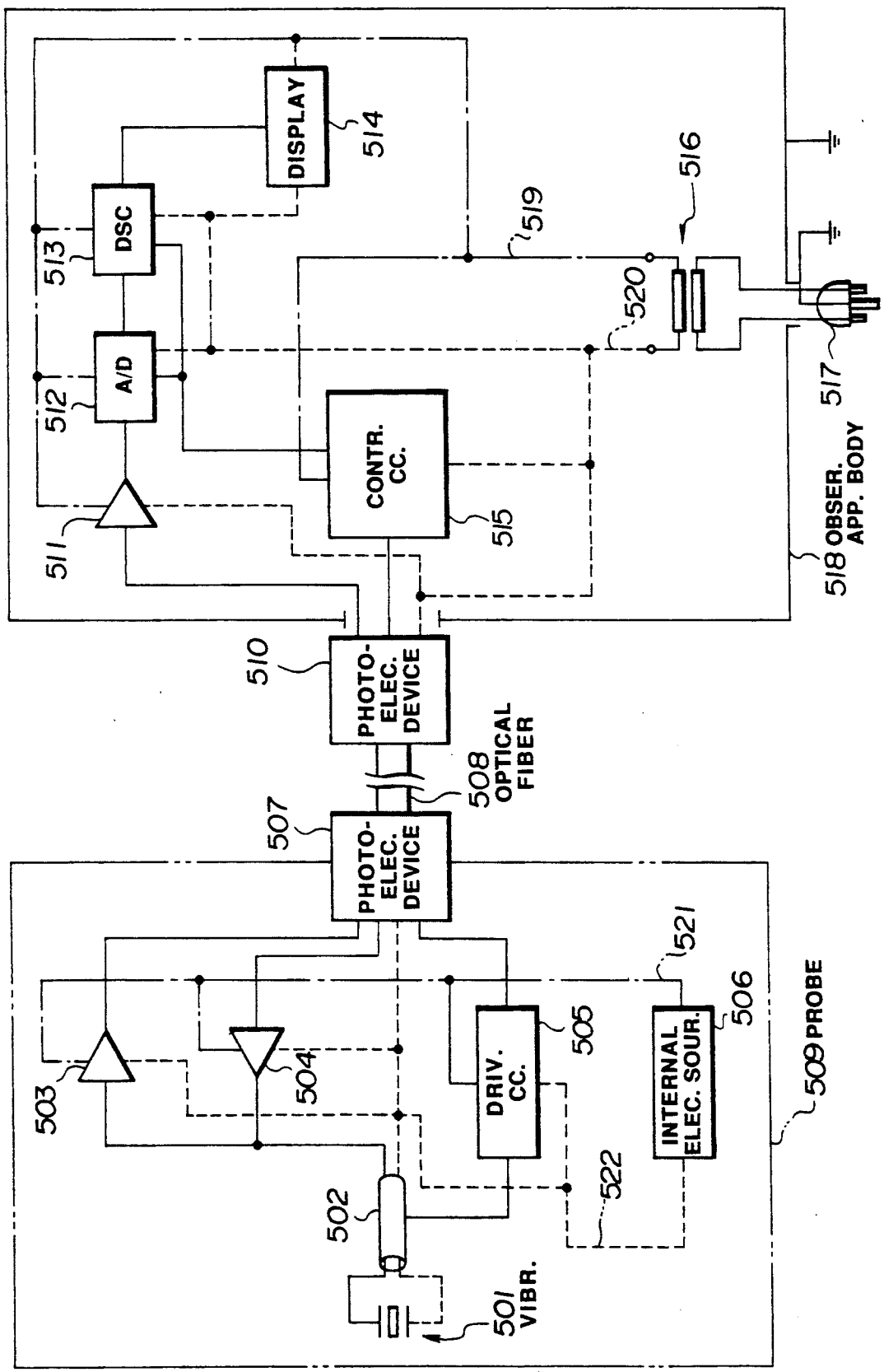
FIG. 52 illustrates the configuration of a thirteenth embodiment of the present invention.

FIG. 52 shows a thirteenth embodiment of the present invention.

In this embodiment, an internal power source is provided within an ultrasonic probe.

The ultrasonic observation device according to this embodiment comprises a probe 509 for diagnosing a body cavity, a main body 518 of an observation device to which the ultrasonic probe is connected. The probe 509 is a mechanical scan type probe having an oscillator 501 which is connected to am amplifier 503 and an transmitter 504 via a power transmitting portion 502. The power transmitting portion 502 is supplied with power by a driving circuit 505. The control signal line to transmit the control signal for controlling the driving circuit 505 is connected to a photoelectric element 507 for converting an electrical signal into an optical signal.

Both the amplifier 503 and transmitter 504 are connected to the photoelectric element 507. Within the probe 509, an internal power source 506 is provided by which the amplifier 503, transmitter 504 and driving circuit 505 are supplied with power.

The photoelectric element 507 of the probe 509 is connected to a photoelectric element 510 of the main body 518 of the observation device. A receiver 511 and a control circuit 515 are connected to the photoelectric element 510. To the output side of the photoelectric element 511, an A-D converter 512, a digital scan converter (referred to as DSC hereinafter) 513 and a display 514 are connected in this order. The control circuit 515 sends control signals to the converter 512 and the DSC 513. The power source of each circuit within the main body 518 of the observation device, i.e., the receiver 511, A-D converter 512, DSC 513, display 514 and control circuit 515, is connected to the secondary of a transformer 516 within the main body 518 of the observation device. A power source cable 517 for leading the commercial power source is connected to the primary of the transformer 516. The secondary of the transformer 516 has already become a DC power source due to a rectifying circuit which is not shown.

The operation of this embodiment will now be described.

The power source cable 517 is connected to the commercial power source to lead the commercial power source to a primary circuit of the transformer 516. The primary and the secondary circuits of the commercial power source are insulated by the transformer 516, and desired voltage and current are generated at the secondary. The voltage and current are converted into a DC voltage and a DC current by a rectifying circuit which is not shown, and supply a power source to each circuit of the main body 518 of the observation device from the positive pole 519 and negative pole 520 of a secondary circuit power source. The control circuit 515 which has been supplied with the power source outputs control signals to the photoelectric element 510, A-D converter 512 and DSC 513. The control signal sent to the photoelectric element 510 is converted by the photoelectric element 510 into an optical signal and transmitted to the side of the probe 509 via an optical fiber 508. At the probe 509, the control signal is converted into an electrical signal by the photoelectric element 507 and sent to the driving circuit 505 to start the driving circuit 505. The power source of each circuit within the probe 509, i.e the driving circuit 505, transmitter 504 and the receiver 503, is supplied by the positive pole 521 and negative pole 522 of the internal power source 506. The driving circuit 505 causes the power transmitting portion 502 to rotate and thereby causes the oscillator 501 to rotate. The driving circuit also detects the angle of the rotation of the oscillator 501, performs photoelectrical conversion of the rotational angle signal using the photoelectric element 507 and sends it to the main body 518 of the observation device via the optical fiber 508. The signal is then converted into an electrical signal by the photoelectric element 510 and sent to the control circuit 515. The control circuit 515 performs photoelectrical conversion on a transmission trigger synchronized with the rotational angle signal using the photoelectric element 510 and sends it to the transmitter 504 via the optical fiber 508 and photoelectric element 507. The transmitter 504 drives the oscillator 501 with the transmission trigger and an ultrasonic pulse is transmitted from the oscillator 501 into a human body. The echo reflected by a boundary between organs in the body is received by the oscillator 501 and converted into an electrical signal. The received echo signal is amplified by the amplifier 503. The output of the amplifier 503 receives photoelectrical conversion by the photoelectric element 507 and input to the receiver 511 via the optical fiber 508 and the electric element 510. It is then processed by the receiver 511, sampled by the A-D converter 512 into a digital signal and stored in DSC 513. The signal stored in the DSC 513 is read in synchronization with a television signal and thus an ultrasonic cross-sectional image is formed on the display 514.

In this embodiment, the main body 518 of the observation device and the probe 509 are totally floated by separating them electrically while enabling exchange of signals between them using the optical signal. Since the leakage current is suppressed considerably with the above arrangement, this embodiment can be a safe ultrasonic diagnosis device which complies with medical safety standards. Therefore, it will keep patients safe if it is used for diagnosis or operation of blood vessel, heart and the like.

The separation of the probe 509 and the main body 518 of the observation device provides good operability. In case the internal power source 506 within the probe 509 is up, it is enough to replace the probe 509. Thus diagnosis can be continued immediately.

Also, since the probe 509 and the main body 518 of the observation device are connected only by the optical fiber 508, the device is protected from line noise between the probe 509 and the main body 518 of the observation device.

The internal power source 506 can be used for a long time because it supplies power only to the circuits at the side of the probe 509.

Figure 53:
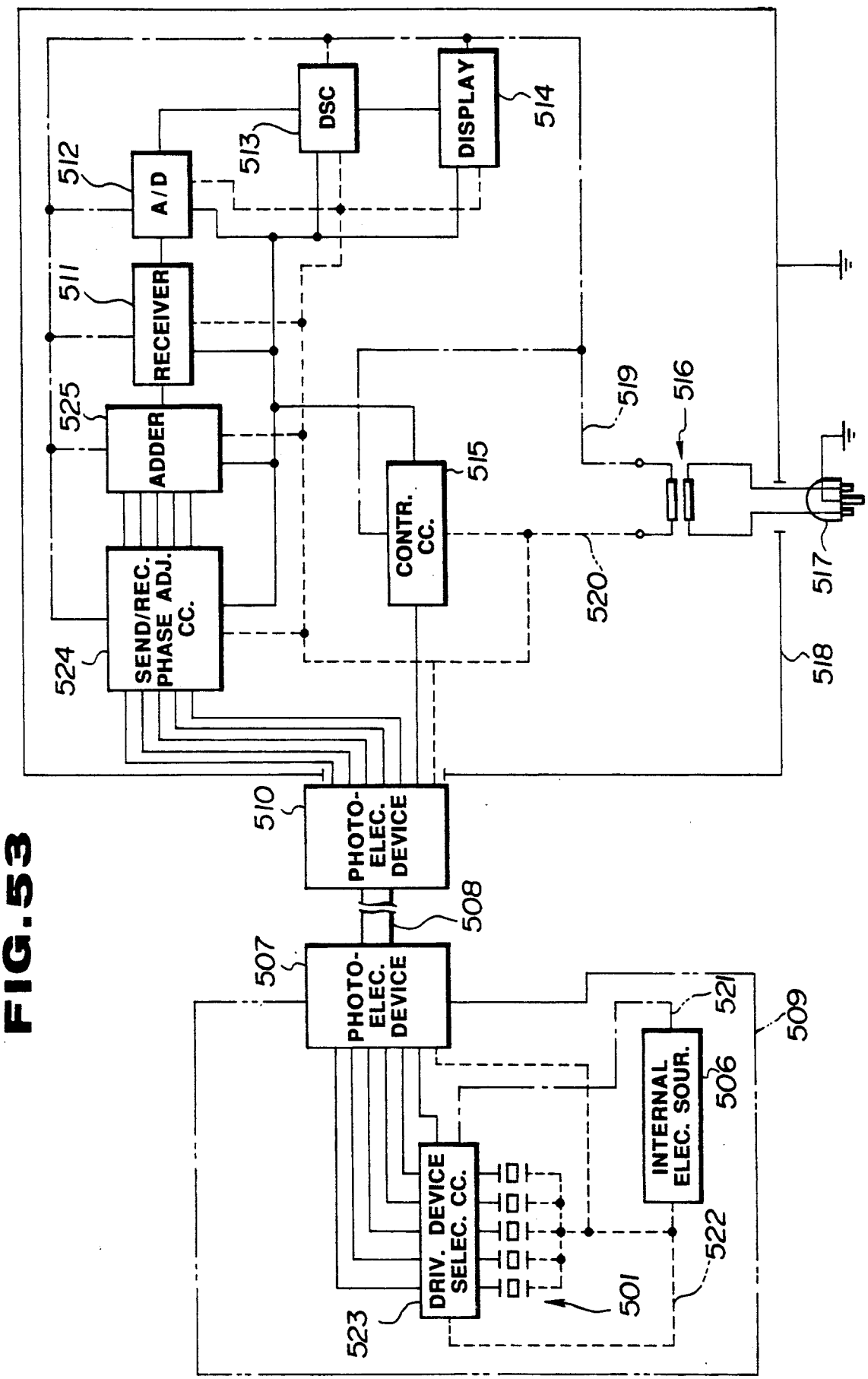
FIG. 53 illustrates the configuration of a fourteenth embodiment of the present invention.

FIG. 53 shows a fourteenth embodiment of the present invention.

The ultrasonic observation device according to this embodiment is a example of an electronic scan type device.

The configuration of a probe 509 is different from the thirteenth embodiment in that a plurality of oscillator 501 are provided within the probe 509 and each oscillator 501 is connected to a driving element selecting circuit 523. The driving element selecting circuit 523 is connected to a photoelectric element 507. The driving element selecting circuit 523 is supplied with a power source by an internal power source 506. A transmission/reception phasing circuit 524 is provided within a main body 591 of the observation device and the transmission/reception phasing circuit 524 is connected to a photoelectric element 510. The output of the transmission/reception phasing circuit 524 is added by an adding circuit 525 and input to a receiver 511. The power source of each circuit within the main body 518 of the observation device including the transmission/reception phasing circuit 524 and the adding circuit 525 is supplied by the secondary of a transformer 516.

Other configurations are the same as that of the thirteenth embodiment.

The operation of this embodiment will now be described.

A control circuit 515 outputs a transmission trigger to the transmission/reception phasing circuit 524. The transmission/reception phasing circuit 524 determines a desired number of driving elements and a desired amount of delay. It performs photoelectrical conversion on a pulse carrying information using the photoelectric element 510, and sends it to the driving element selecting circuit 523 on the side of the probe 509 via a photoelectric element 507. The driving element selecting circuit 523, which is supplied with power source by the internal power source 506, selectively drives some of the plurality of oscillators 501. Thus an ultrasonic beam is electronically scanned. A reception echo signal received by the oscillator 501 passes the driving element selecting circuit 523, receives photoelectrical conversion by the photoelectric element 507, and is led to the transmission/reception phasing circuit 524 within the main body 518 of the observation device via the operation fiber 508 and the photoelectric element 510. The signal phased by the transmission/reception phasing circuit 524 is added by the adding circuit 525, and then it is sent to an A-D converter via receiver 511 to be sampled into a digital signal. It is then synchronized with a television signal by a DSC 513 and thus an ultrasonic cross-sectional image is formed on a display 514.

According to this embodiment, the device is compatible with a high frame rate because it uses an electronic scan.

Other operations and effects are the same as those of the thirteenth embodiment.

Figure 54:
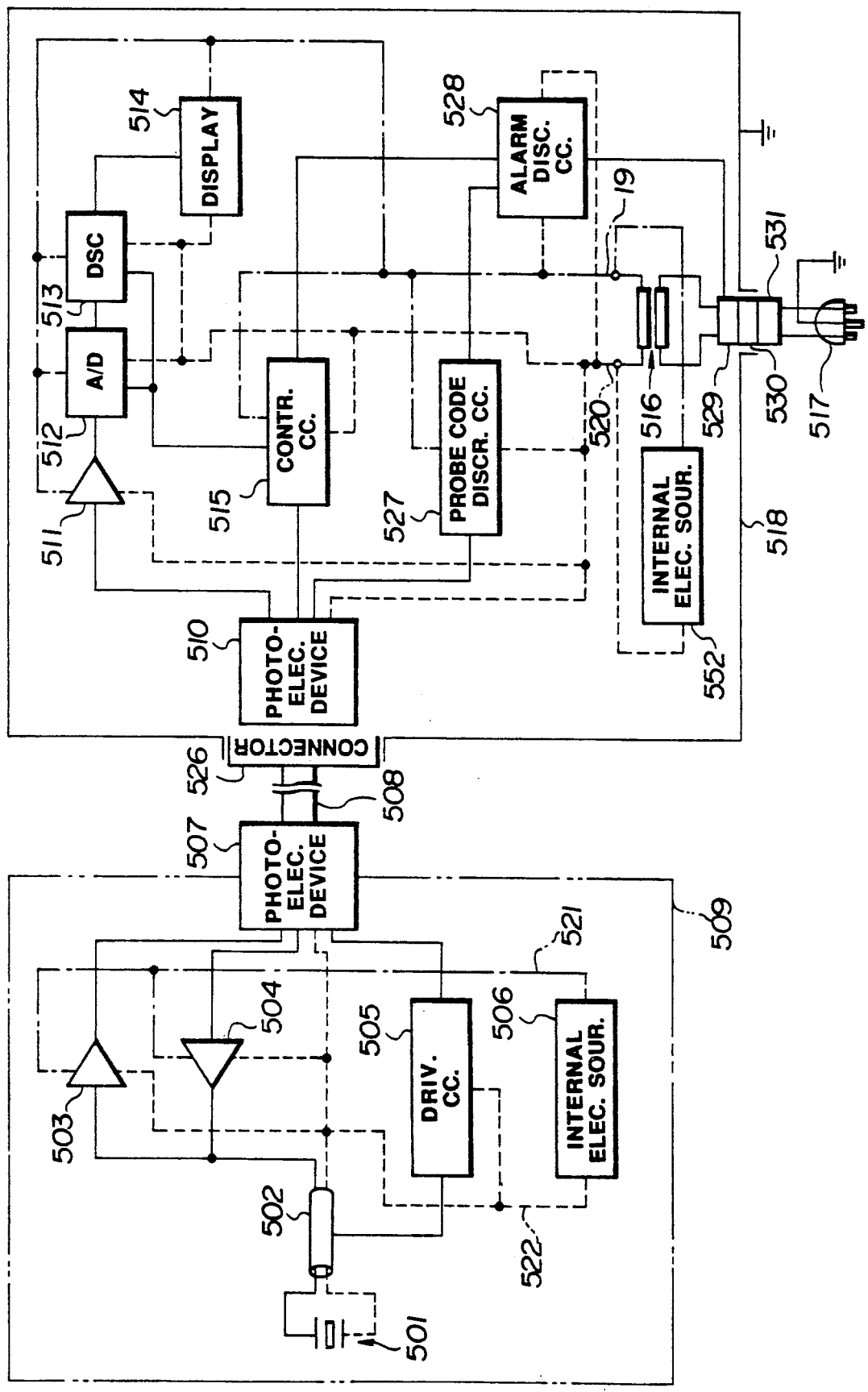
FIG. 54 illustrates the configuration of a fifteenth embodiment of the present invention.

FIG. 54 shows a fifteenth embodiment of the present invention.

The configuration of a probe 509 of the ultrasonic observation device according to this embodiment is the same as that in the thirteenth embodiment.

At the side of a main body 518 of the observation device, a connector 526 which is provided on the end of an optical fiber connecting the main body to the probe 509 is connected to a photoelectric element 510. On this connector 526, there is provided a code which identifies if the probe 509 incorporates a power source or not. Within the main body 518 of the observation device, a probe code recognizing circuit 527, for recognizing the code provided on the connector 526, is connected to the photoelectric element 510.

Also an outlet 531 is provided on the main body side end of the cable for leading the commercial power source to the main body 518 of the observation device. An inlet 530 is provided on the main body 518 of the observation device and this inlet 530 is connected to the primary of a transformer 516. An outlet recognizing sensor 529 is mounted on the inlet 530. An outlet recognition signal which is the output of the outlet recognizing sensor 529 and a probe code recognition signal which is the output of the probe code recognizing circuit 527 are input to an alarm recognizing circuit 528. The alarm recognizing circuit 528 sends the control circuit 515 an alarm recognition signal which indicates whether to generate an alarm based on the outlet recognition signal and the probe code recognition signal. If alarm is generated, the control circuit 515 sends an alarm displaying signal to the DSC 513 causing a display 514 to display the alarm.

An internal power source 552 is provided within the main body 518 of the observation device. The internal power source 552 is connected to the secondary of the transformer 516.

The power source of each circuit within the main body 518 of the observation device including the probe code recognizing circuit 527 and the alarm recognizing circuit 528 is supplied by the commercial power source from the internal power source 522 or the transformer 516.

Other configurations are the same as that of the thirteenth embodiment.

In this embodiment, each circuit within the main body 518 of the observation device is operated by the internal power source 552 if required. Thus, the electrical safety of the device can be further improved by reducing leakage current in the main body 518 of the observation device by means of removal of the commercial power source.

Also, in case the commercial power source is used in the combination of the probe having the internal power source 506 and the main body 518 of the observation device, the alarm display will be shown on the display 514 by the alarm recognizing circuit 528.

In this embodiment, therefore, it is possible to confirm the safety of the ultrasonic observation device against leakage current only by watching the display 514.

The display on the display 514 may be arranged to show whether the probe 509 incorporates a power source or not, or whether the internal power source 552 in the main body 518 of the observation device is used or not.

Other operations and effects are the same as those of the thirteenth embodiment.

This invention is not limited to the above embodiments. For example, in the thirteenth through fifteenth embodiments, the probe 509 may be of a disposable type so that it may be replaced at each diagnosis. This will eliminate the need for charging or replacing the internal power source 506.

Also the internal power source within the probe 506 or the main body 518 of the observation device may be of a type to be replaced or a chargeable type.

The thirteenth through fifteenth embodiments may be applied to a variety of ultrasonic observation devices such as a type in which a probe is inserted into a body cavity, a type in which a probe is put in contact with the surface of the body and an ultrasonic autoscope having a probe provided on the head portion of the inserted portion.

Figure 55:
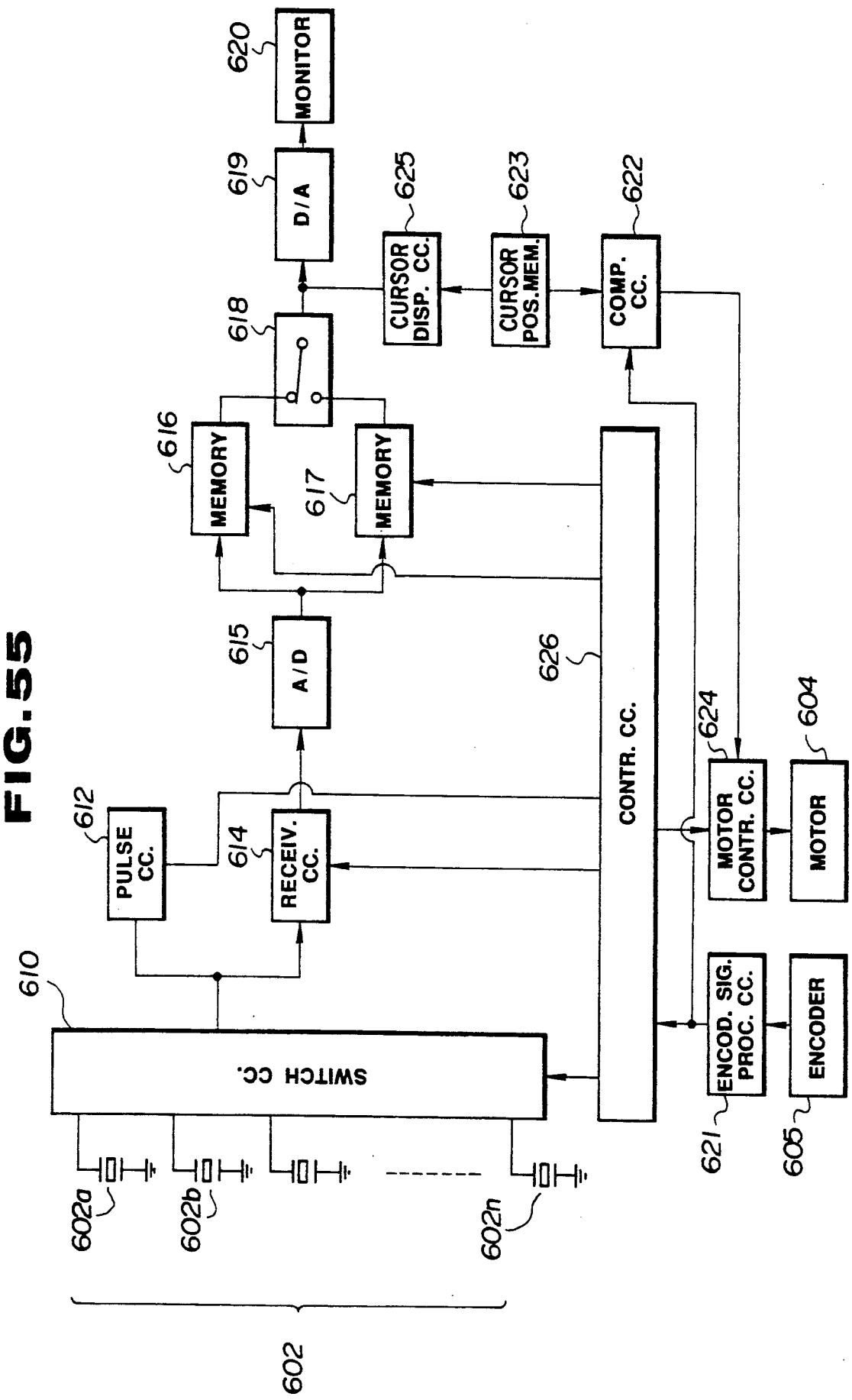
FIG. 55 through FIG. 57 relate to a sixteenth embodiment of the present invention.

FIG. 55 shows a sixteenth embodiment of the present invention.

Figure 56:
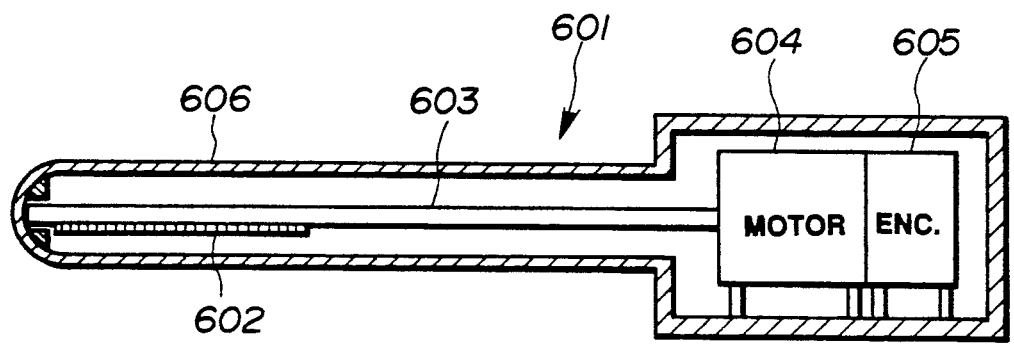

In this embodiment, as shown in FIG. 56, an ultrasonic probe 601 comprises an ultrasonic oscillator 602 for linear scanning. The oscillator 602 is mounted at the head side of a pipe 603 penetrating a probe 601, and on a surface including the pipe 603. The back end of the pipe 602 is attached to a motor 604 and the pipe is rotated by the motor 604. The quantity of the rotation can be detected by an encoder 605. The pipe is rotatably pivoted at the head portion thereof. A tube 606 of the probe 601 is formed of a material which transmits an ultrasonic wave.

Figure 57:
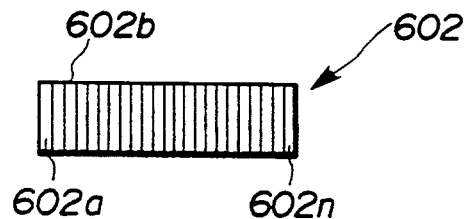

The ultrasonic oscillator 602 comprises a multiplicity of oscillator elements such as 602a, 602b ... 602n as shown in FIG. 57. Signal lines connected to each element 602i (i=a, b, ... n) are inserted into the pipe 603.

Each element 602i of the ultrasonic oscillator can be scanned linearly by switching them sequentially using a switching circuit 610 as shown in FIG. 57 while they are transmitting and receiving ultrasonic waves. A radial scan can be performed by moving the cursor to the desired position in the linear scan image, selecting the desired element 602i with the switching circuit 610 and rotating the pipe 603 using the motor 604.

To perform a linear scan at the desired position in a radial scan image, element 6*i* shall be switched sequentially while they are driven by the motor 604.

In FIG. 55, a pulse from the pulser circuit 612 is applied to a selected element 6*i* of the oscillator 602 via switching circuit 604. Also the received signal is input to a reception circuit 614 via the switching circuit 610. Then after it is converted into a digital signal by an A-D converter 615, it is stored in memories 616 and 617 alternately. The signal data stored in the memories 616 and 617 is alternately read through a switch 618 and displayed on a monitor 620 via D-A converter 619.

On the other hand, the signal of the encoder 605 is input to an encoder processing circuit 621 It is then compared with a value held by a cursor position memorizing circuit 623 through a comparing circuit 622 and input to a motor controlling circuit 624 to rotate the motor 604.

The value in the cursor position memorizing circuit 623 is input to a cursor displaying circuit 625 and displayed on the monitor 620 via the D-A converter 619, the display overlapping the image in the memories 616 and 617. The reference numeral 625 represents a control circuit which controls each circuit.

Figure 58:
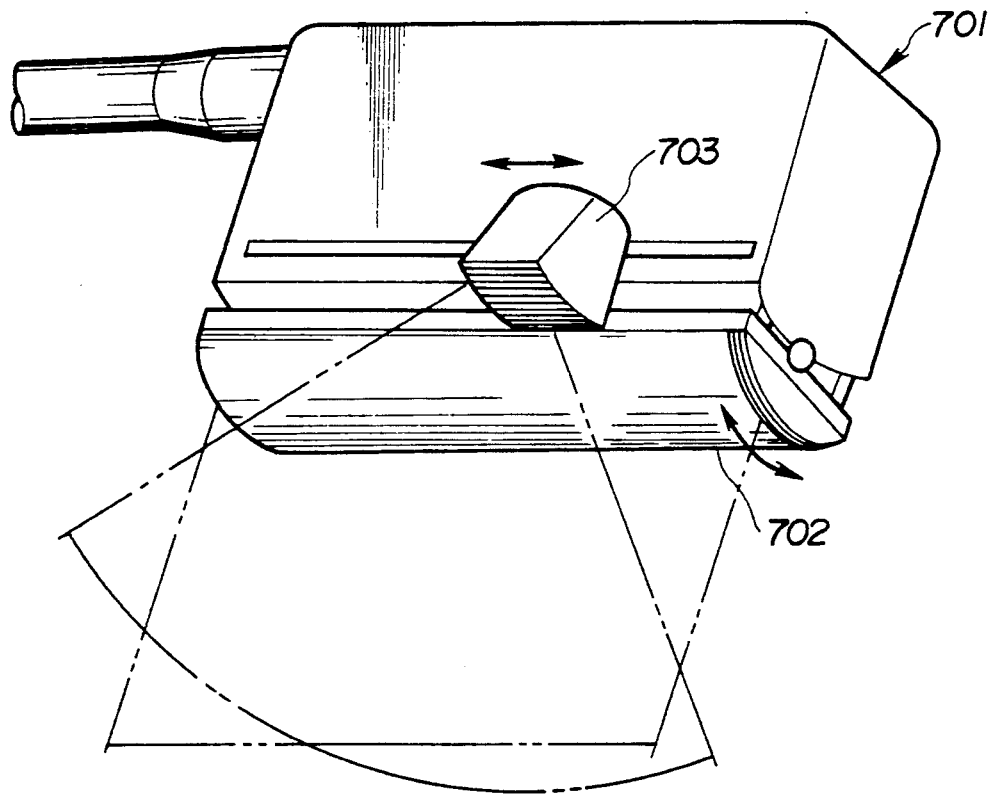
FIG. 58 and FIG. 59 relate to a seventeenth embodiment of the present invention.

FIG. 58 shows the ultrasonic oscillator in the seventeenth embodiment of the present invention.

As shown in the figure, two independent oscillators are provided on a probe 701. They are an ultrasonic oscillator 702 for linear electronic scanning and an ultrasonic oscillator 703 for sector or convex electronic scanning.

Figure 59:
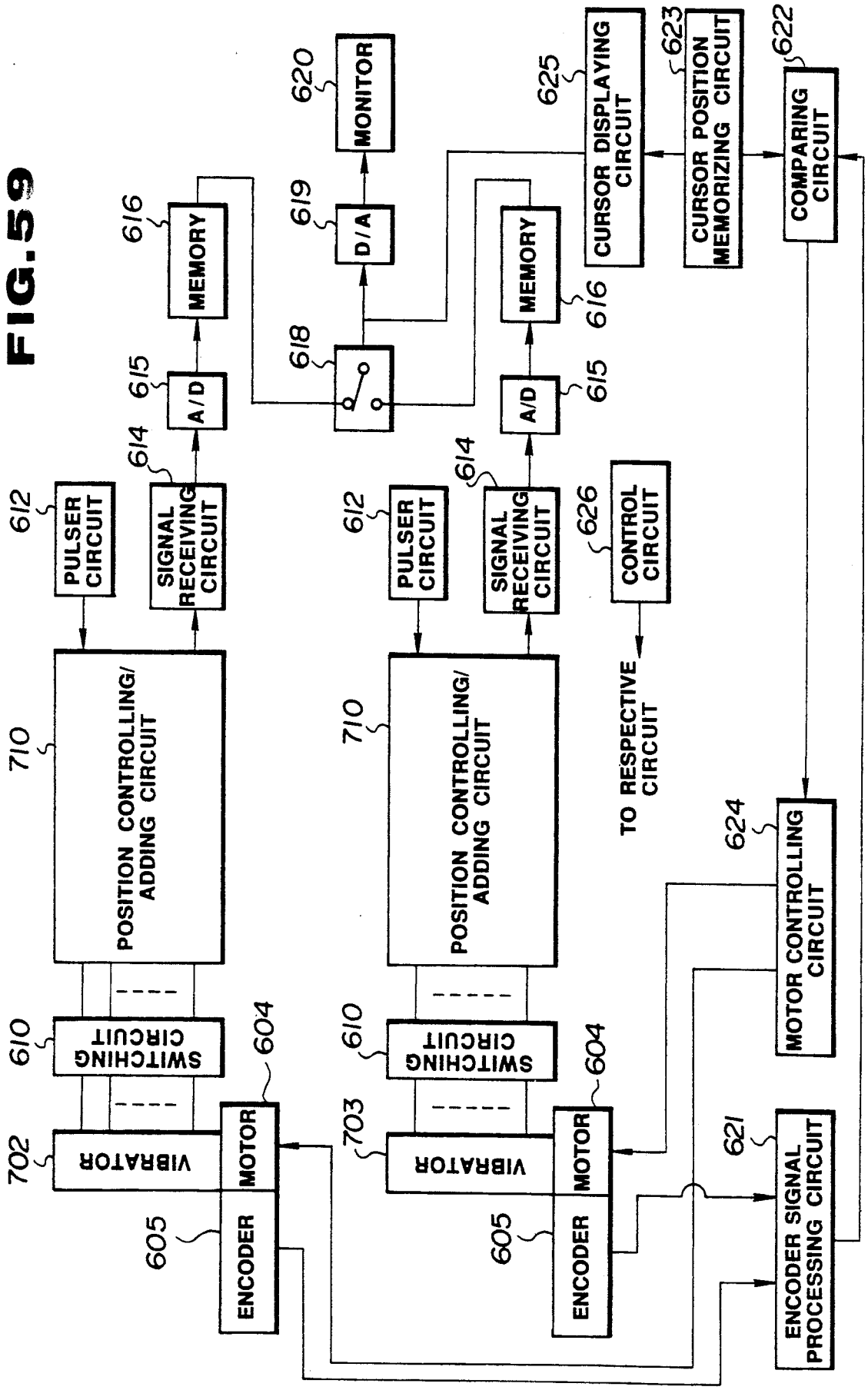

The oscillators 702 and 703 are driven through the switching circuits 610 and 610' respectively as shown in FIG. 59.

In FIG. 59, the components which have been described in FIG. 55 carry the same reference numerals. A description is omitted for the same reference numerals here.

A phase controlling/adding circuit 710 performs addition after applying a phase difference and is designed to electronically focus an ultrasonic beam.

Figure 60:
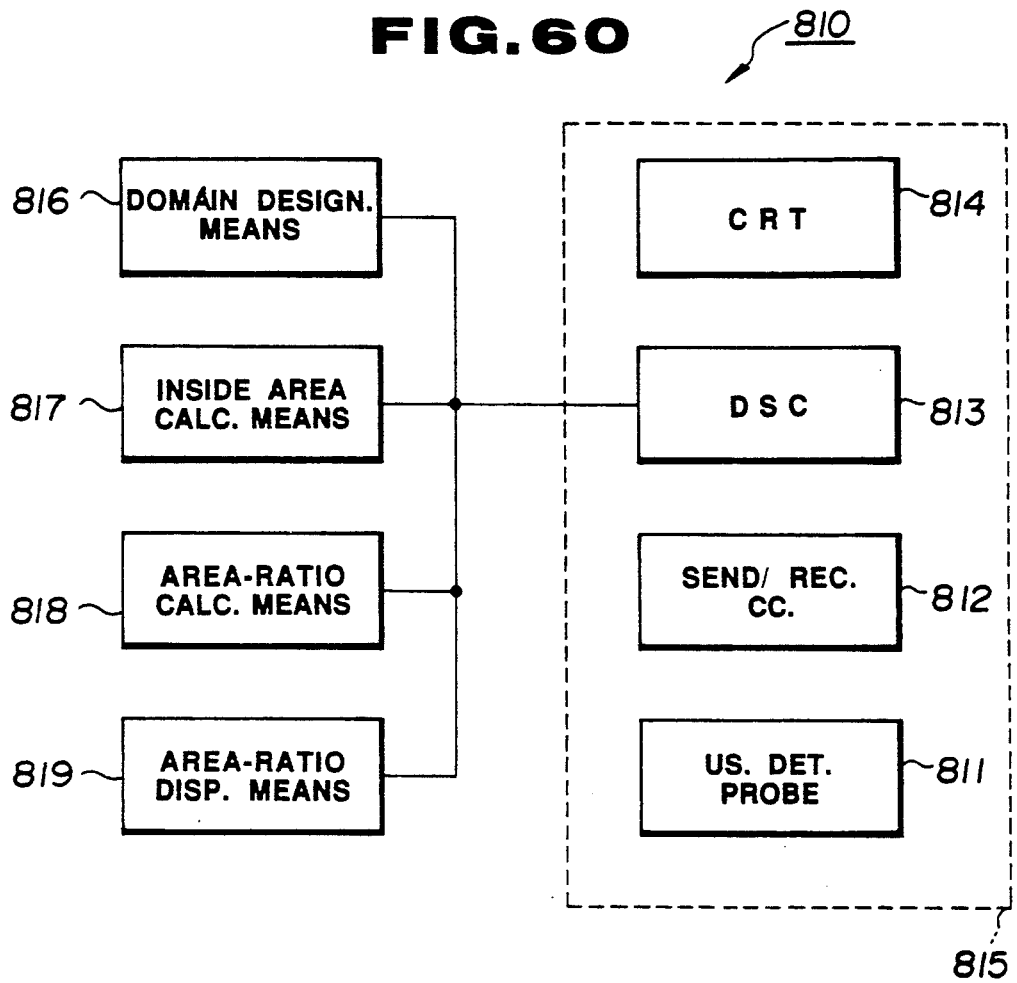
FIG. 60 through FIG. 62 relate to an eighteenth embodiment of the present invention.
Figure 61:
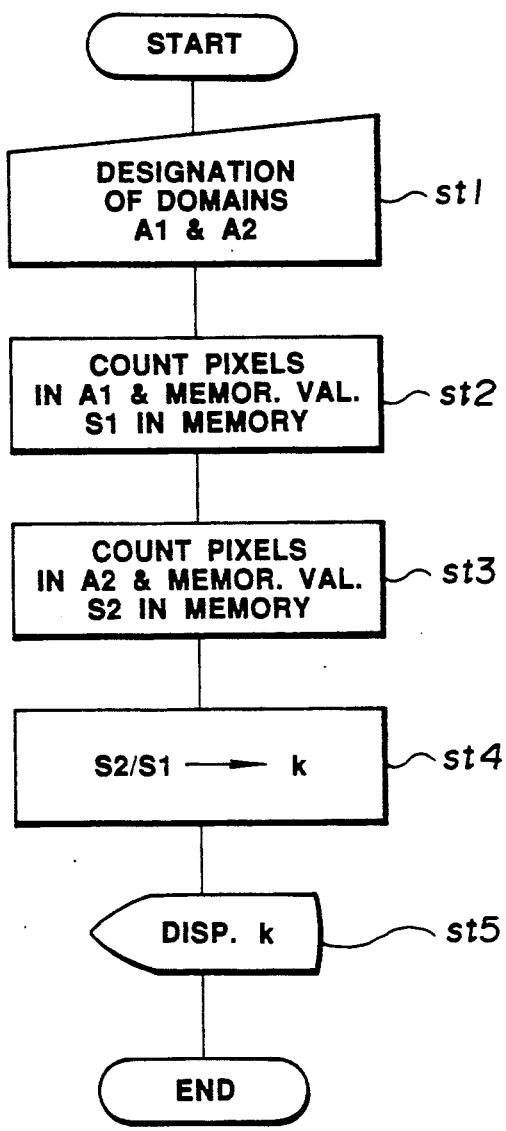

While an area ratio is calculated with the configuration as shown in FIG. 16 in the first embodiment, the area ratio may be calculated with the configuration as shown in FIG. 60 and by the process shown in FIG. 61.

The device per FIG. 60 comprises a transmission/reception circuit 812 comprising a (ultrasonic) search unit 811 for transmitting and receiving an ultrasonic wave provided within a probe insertable into a blood vessel which is not shown, a transmission circuit for transmitting a signal to excite the ultrasonic wave to the search unit 811 and a reception circuit for amplifying a signal received by the search unit 811. An ultrasonic observation device 815 has a B mode ultrasonic diagnosis function comprising a DSC 813 converting a signal from the transmission/reception circuit 812 into a video signal for display and a CRT 814 for displaying the output signal of the DSC 813. A region designating means 816 comprises a light pen or track ball for designating a plurality of any desired regions on the CRT 814. A region area calculating means 817 calculates the area of the regions designated by the region designating means 816 by counting the picture elements in the designated region. A region area ratio calculating means 818 calculates the ratio of the area of the plural regions calculated by the region area calculating means 817. An area ratio displaying means 819 displays the area ratio calculated by the region area ratio calculating means 818.

Figure 62:
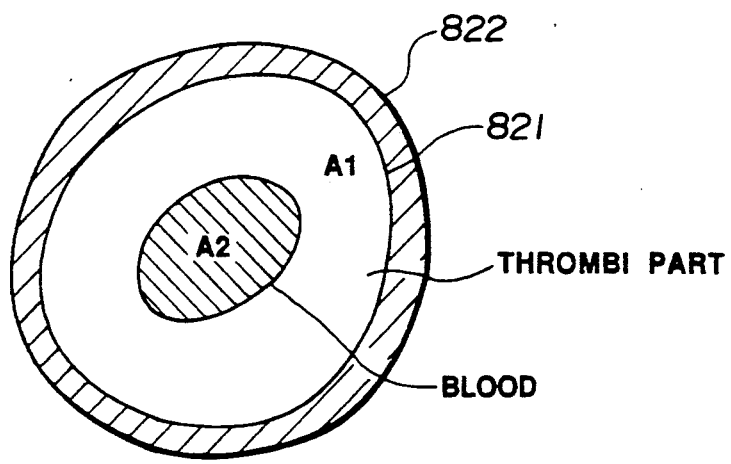

By transmitting and receiving an ultrasonic wave at the search unit 811 by inserting the probe into a blood vessel, the ultrasonic cross-sectional image of the blood vessel is displayed on the CRT 814, for example, as shown in FIG. 62.

In FIG. 62, the innermost region A2 represents the blood portion while the region A1 outside A2 represents a thrombus portion. The outer boundary of the thrombus represents the inner wall 821 of the blood vessel while the outside of the inner wall 821 represents the outer wall 822 of the blood vessel.

Therefore, if a doctor designates the regions for which an area ratio is desired using a light pen or track ball on an ultrasonic cross-sectional image displayed on the CRT 814, the area ratio S2/S1 can be displayed on the CRT 814 in accordance with the process shown in FIG. 61.

For example, step st1, designating the region A2 which is the portion of the blood, is carried out by designating the region A1 along the inner wall 821 of the blood vessel, and then designating the boundary of the blood portion.

Then the region area calculating means 817 counts the number of the picture elements within the region A1 as shown in step st2 and stores the resulting count value S1 in a memory which is not shown. Also it counts the number of the picture elements within the region A2 as shown in step st3 and stores the resulting count value in a memory which is not shown. After step st3, the region area ratio calculating means 818 calculates the ratio of the value S1 to S2 stored in the memories as shown in step st4 to obtain a value K which is S2/S1. Then the area ratio displaying means 819 displays the value K on the CRT 814 as shown in step st5.

As many apparently widely different embodiments of this invention may be made based on this invention without departing from the spirit and scope thereof, it is to be understood that the invention is not limited to the specific embodiments thereof except as defined in the appended claims.

We claim:

1. An ultrasonic diagnosis device comprising:
    an ultrasonic probe having an insertable portion insertable into a blood vessel and incorporating an ultrasonic oscillator for transmitting and receiving an ultrasonic wave, said ultrasonic probe having an internal power source;
    a scanning means for rotatively and/or linearly scanning an emitting direction of said ultrasonic wave;
    a reception signal outputting means for outputting a reception signal corresponding to an ultrasonic echo signal which has been received by said ultrasonic oscillator after transmission of the ultrasonic wave from said ultrasonic oscillator; and
    a quantitative detecting means for determining, based upon said ultrasonic echo signal, at least one of a cross-sectional area of a blood vessel, a diameter of the blood vessel, a thickness of a blood vessel wall and pulsative changes thereof.

2. A device according to claim 1 further comprising a cross-sectional image generating means for generating a video signal corresponding to an acoustic cross-sectional image of the blood vessel from the reception signal from the reception signal output means and a monitor means displaying the acoustic cross-sectional image upon input of the video signal.

3. A device according to claim 2 wherein the cross-sectional image generating means comprises a scanning signal generating means having an input of an angle information corresponding to each direction in which the ultrasonic wave is transmitted from the ultrasonic oscillator and an input of time, which is a period after transmission of the ultrasonic wave in each direction, until detection of the ultrasonic echo signal by the ultrasonic oscillator, and said scanning signal generating means for generating a scanning signal which determined a position of display of the video signal to be displayed on the monitor means.

4. A device according to claim 2 wherein the ultrasonic probe comprises a photoelectrical element for transmitting signals with the cross-sectional image generating means over an optical fiber.

5. A device according to claim 2 further comprising an internal power source.

6. A device according to claim 1 wherein the ultrasonic probe comprises a pressure sensor for detecting pressure at the insertable portion.

7. A device according to claim 6 further comprising elasticity calculating means for calculating elasticity of the blood vessel from an output signal from the quantitative detecting means and an output signal from the pressure sensor.

8. A device according to claim 6 further comprising a pressure change quantity calculating means for calculating an amount of change in pressure inside the blood vessel wall from an output of the pressure sensor.

9. A device according to claim 1 and comprising a three-dimensional image generating mans for generating a three-dimensional image of the blood vessel wall from the reception signal.

10. A device according to claim 1 wherein the scanning means comprises a rotary drive means for driving the ultrasonic oscillator in rotary motion in an angular direction about a longitudinal axis of the ultrasonic probe wherein the emitting direction of transmission and a direction of reception of the ultrasonic wave is mechanically changed.

11. A device according to claim 10 wherein the rotary drive means comprises a motor.

12. A device according to claim 10 further comprising a translatory drive means for moving the ultrasonic oscillator in the axial direction to an ultrasonic probe.

13. A device according to claim 12 wherein the translatory drive means is a reciprocating drive means for reciprocating the ultrasonic oscillator in the axial direction.

14. A device according to claim 12 further comprising travel quantity detecting means for detecting an amount of travel of the ultrasonic oscillator in the axial direction.

15. A device according to claim 14 further displaying a three-dimensional image of the blood vessel from the reception signal depending on the amount of travel of the ultrasonic probe in the axial direction.

16. A device according to claim 1 wherein the ultrasonic oscillator comprises a plurality of ultrasonic oscillator elements arranged in an angular direction about a longitudinal axis of the ultrasonic probe and wherein the scanning means electronically changes the emitting direction of transmission and a direction of reception of the ultrasonic wave by selecting the ultrasonic element to be driven.

17. A device according to claim 10 or claim 3 further comprising angle detecting means for detecting the angular direction in which the ultrasonic wave is transmitted by the ultrasonic oscillator.

18. A device according to claim 17 wherein the quantitative detecting means comprises measuring means for measuring a period from transmission of the ultrasonic wave from the ultrasonic oscillator until reception of the ultrasonic echo signal received by the ultrasonic oscillator.

19. A device according to claim 18 wherein the quantitative detecting means comprises a cursor signal generating means for outputting a cursor to indicate a location at which the ultrasonic echo signal has been generated to a monitor means from the period measured by the measuring means and angle information detected by the angle detecting means.

20. A device according to claim 19 wherein the reception signal output means comprises gate means for eliminating the ultrasonic wave received within a certain period after transmission of the ultrasonic wave from the ultrasonic oscillator.

21. A device according to claim 20 wherein the gate means eliminates the ultrasonic echo signal reflected by a cap containing the ultrasonic oscillator.

22. A device according to claim 20 wherein the gate means eliminates the ultrasonic echo signal reflected by a balloon attached to an outside of a cap containing the ultrasonic oscillator.

23. A device according to claim 20 wherein the reception signal output means comprises determining means for determining whether a received ultrasonic echo signal exceeds a reference level.

24. A device according to claim 23 wherein the quantitative detecting means comprises a memory means for storing the period measured by the measuring means upon a first signal output through the gate means and the determining means.

25. A device according to claim 23 wherein the reception signal output means comprises a memory means for storing each period measured by the measuring means from output of first and second signals output through the gate means and the determining means.

26. A device according to claim 18 wherein the measuring means comprises a counter for counting a reference clock synchronized with a time in which the ultrasonic wave is transmitted by the ultrasonic oscillator.

27. A device according to claim 1 wherein the ultrasonic probe has a preamplifier for amplifying the ultrasonic echo signal received by the ultrasonic oscillator.

28. A device according to claim 1 wherein the quantitative detecting means outputs information about the blood vessel in real time.

29. A device according to claim 1 wherein the quantitative detecting means comprises measuring means for measuring a period after transmission of the ultrasonic wave by the ultrasonic oscillator until reception of the ultrasonic echo signal received by the ultrasonic oscillator, measurement of said period being carried out in said measuring means in plural directions about a longitudinal axis of the ultrasonic probe.

30. A device according to claim 29, wherein the quantitative detecting means comprises a distance calculating means which calculates at least either a distance up to an inner surface or an outer surface of the blood vessel wall from a position of ultrasonic wave transmission, based on the period measured by the measuring means.

31. A device according to claim 29 wherein the quantitative detecting means comprises a cross-sectional area calculating means which calculates a distance from a point of ultrasonic wave transmission to a boundary between a thrombus and blood, and to an inner surface of the wall of the blood vessel based on the period measured by the measuring means therein calculating a ratio of cross-sectional area of the thrombus to cross-sectional area of the blood vessel.

32. A device according to claim 1 further and comprising a thickness calculating means for calculating thickness of the blood vessel wall.

33. A device according to claim 32 wherein the thickness calculating means comprises an average thickness calculating means for calculating an average thickness of the blood vessel wall.

34. A device according to claim 1 wherein the quantitative detecting means comprises a cross-sectional area calculating means for calculating the cross-sectional area of the blood vessel wall.

35. A device according to claim 34 wherein the cross-sectional area calculating means comprises an average cross-sectional area calculating means for calculating an average cross-sectional area of the blood vessel wall.

36. A device according to claim 34 wherein the cross-sectional area calculating means comprises a cross-sectional area change quantity calculating means for calculating an amount of the change in a cross-sectional area of the blood vessel wall depending on time.

37. A device according to claim 1 wherein the ultrasonic probe comprises a support means at a head portion of the insertable portion for supporting a part of the insertable portion onto an inner wall of the blood vessel.

38. A device according to claim 37 wherein the support means is formed of an elastic member which may project and withdraw from an opening formed on the insertable portion.

39. A device according to claim 38 wherein the opening is a plurality of openings formed in a circumferential direction of a head portion side of the insertable portion and the elastic member is a flexible wire which may project and withdraw from each opening.

40. A device according to claim 39 wherein the flexible wire may project and withdrawn from each opening at one of the ends thereof and may be controlled based on an amount of projection from the opening by operating another end thereof which penetrates through the probe up to a base of the probe.

41. A device according to claim 38 wherein the elastic member may be controlled based on an amount of projection from the opening by operation at a probe base side.

42. A device according to claim 37 wherein the support means is a balloon which is attached to an outer circumference of the insertable portion.

43. A device according to claim 1 wherein the ultrasonic probe is provided at a head portion of the insertable portion and is contained in a cap having an acoustic window which transmits at least ultrasonic waves.

44. A device according to claim 43 wherein the acoustic window is covered by a ultrasonic transparent member which transmits ultrasonic waves.

45. A device according to claim 43 wherein within the cap, ultrasonic transmitting liquid surrounds the ultrasonic oscillator.

46. A device according to claim 1 wherein the reception signal output means comprises voltage variable amplifying means or a voltage variable band-pass filter which are voltage-controlled with regard to gain or passing band against the ultrasonic echo signal received by the ultrasonic oscillator.

47. A device according to claim 46 further comprising a control signal generating means for varying a level of voltage which controls voltage variable amplifying means or voltage variable band-pass filter, when a reference time has elapsed after the transmission of the ultrasonic wave by the ultrasonic oscillator.

48. A device according to claim 47 further comprising a reference time changing means for changing the reference time.

49. A device according to claim 48 wherein the reference time is variably set by probe information corresponding to the ultrasonic probe which is being used.

50. A device according to claim 49 further comprising a light pen which variably sets the reference time.

51. A device according to claim 1 wherein the ultrasonic probe comprises a driving circuit for driving the ultrasonic oscillator which operates on power supplied by the internal power source.

52. A device according to claim 1 wherein the quantitative detecting means calculates an average value of the information about the blood vessel in a period of pulsant change of the blood vessel.

53. A device according to claim 1 wherein the scanning means comprises a rotary driving means for driving the ultrasonic oscillator in a rotary motion and a shaft member which penetrates through the insertable portion, the shaft member is attached to an input portion of the ultrasonic oscillator on one end of the shaft member and connected to the rotary driving means on another end of the shaft member.

54. A device according to claim 1 wherein the ultrasonic oscillator comprises a plurality of oscillator elements for transmitting and receiving said ultrasonic echo signal of the ultrasonic wave, said oscillator elements are attached to a head portion side of the insertable portion in a circumferential direction to the insertable portion.

* * * * *